(12) United States Patent
Yu et al.

(10) Patent No.: US 11,999,953 B2
(45) Date of Patent: Jun. 4, 2024

(54) COMPOSITIONS AND METHODS FOR TREATING TRANSPOSON ASSOCIATED DISEASES

(71) Applicant: THE CHILDREN'S MEDICAL CENTER CORPORATION, Boston, MA (US)

(72) Inventors: Timothy Yu, Boston, MA (US); Eunjung Alice Lee, Boston, MA (US)

(73) Assignee: The Children's Medical Center Corporation, Boston, MA (US)

( * ) Notice: Subject to any disclaimer, the term of this patent is extended or adjusted under 35 U.S.C. 154(b) by 558 days.

(21) Appl. No.: 16/645,083

(22) PCT Filed: Sep. 12, 2018

(86) PCT No.: PCT/US2018/050576
§ 371 (c)(1),
(2) Date: Mar. 6, 2020

(87) PCT Pub. No.: WO2019/055460
PCT Pub. Date: Mar. 21, 2019

(65) Prior Publication Data
US 2020/0263173 A1 Aug. 20, 2020

Related U.S. Application Data

(60) Provisional application No. 62/682,031, filed on Jun. 7, 2018, provisional application No. 62/593,649, filed on Dec. 1, 2017, provisional application No. 62/558,036, filed on Sep. 13, 2017.

(51) Int. Cl.
*C12N 15/113* (2010.01)
*C12Q 1/68* (2018.01)

(52) U.S. Cl.
CPC .............. *C12N 15/113* (2013.01); *C12Q 1/68* (2013.01); *C12N 2310/31* (2013.01); *C12N 2310/321* (2013.01); *C12N 2310/33* (2013.01)

(58) Field of Classification Search
CPC .............. C12N 15/113; C12N 2310/31; C12N 2310/321; C12N 2310/33; C12N 2320/33; C12N 2320/34; A61K 31/712; A61K 31/7125
See application file for complete search history.

(56) References Cited

U.S. PATENT DOCUMENTS

| | | |
|---|---|---|
| 3,687,808 A | 8/1972 | Merigan, Jr. et al. |
| 4,426,330 A | 1/1984 | Sears |
| 4,469,863 A | 9/1984 | Ts'o et al. |
| 4,476,301 A | 10/1984 | Imbach et al. |
| 4,534,899 A | 8/1985 | Sears |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,556 A | 5/1991 | Woodle et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,108,921 A | 4/1992 | Low et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |

(Continued)

FOREIGN PATENT DOCUMENTS

| | | | |
|---|---|---|---|
| WO | 2000061595 A1 | 10/2000 | |
| WO | WO-2006000057 A1 * | 1/2006 | .............. A61P 21/00 |

OTHER PUBLICATIONS

Taniguchi-Ikeda et al (Nature 478: 127-131, 2011) (Year: 2011).*
Taniguchi-Ikeda et al (Nature 478: 127-131, 2011, Supplementary information) (Year: 2011).*
Adkin et al (In: Aartsma-Rus, A. (eds) Exon Skipping. Methods in Molecular Biology, vol. 867: 169-188. (2012) (Year: 2012).*
Aartsma-Rus (In: Aartsma-Rus, A. (eds) Exon Skipping. Methods in Molecular Biology, vol. 867: 117-129. (2012) (Year: 2012).*
Hancks et al., "Roles for retrotransposon insertions in human disease," Mobile DNA, May 6, 2016, vol. 7, No. 9, pp. 1-28.

(Continued)

*Primary Examiner* — Richard A Schnizer
(74) *Attorney, Agent, or Firm* — Melissa Hunter-Ensor; Nathan Hsu; Greenberg Traurig, LLP

(57) ABSTRACT

The present invention features antisense oligonucleotides (AONs) for the treatment of diseases and disorders associated with the deleterious effects of transposable element insertion (e.g., long interspersed nuclear element-i (LINE-1), *Arthrobacter luteus* element (Alu), short interspersed nuclear element variable number tandem repeat *Arthrobacter luteus* element (SINE-VNTR-Alu) or (SVA), or endogenous retrovirus (ERV). In one aspect, the invention provides one or more antisense oligonucleotides complementary to a transposable element present in an intronic sequence within a gene. In another aspect, the invention provides a method for treating a subject having a genetic disorder associated with the insertion of a transposable element, the method involving administering to the subject one or more antisense oligonucleotides of any aspect delineated herein.

5 Claims, 34 Drawing Sheets
Specification includes a Sequence Listing.

(56) References Cited

U.S. PATENT DOCUMENTS

| | | |
|---|---|---|
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,213,804 A | 5/1993 | Martin et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,227,170 A | 7/1993 | Sullivan |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,221 A | 11/1993 | Tagawa et al. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,354,844 A | 10/1994 | Beug et al. |
| 5,356,633 A | 10/1994 | Woodle et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,395,619 A | 3/1995 | Zalipsky et al. |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,016 A | 5/1995 | Low et al. |
| 5,416,203 A | 5/1995 | Letsinger |
| 5,417,978 A | 5/1995 | Tari et al. |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,127 A | 10/1995 | Felgner et al. |
| 5,459,255 A | 10/1995 | Cook et al. |
| 5,462,854 A | 10/1995 | Coassin et al. |
| 5,466,677 A | 11/1995 | Baxter et al. |
| 5,466,786 A | 11/1995 | Buhr et al. |
| 5,469,854 A | 11/1995 | Unger et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,295 A | 4/1996 | Kornberg et al. |
| 5,512,439 A | 4/1996 | Hornes et al. |
| 5,512,667 A | 4/1996 | Reed et al. |
| 5,514,785 A | 5/1996 | Ness et al. |
| 5,519,126 A | 5/1996 | Hecht |
| 5,519,134 A | 5/1996 | Acevedo et al. |
| 5,521,291 A | 5/1996 | Curiel et al. |
| 5,525,465 A | 6/1996 | Haralambidis et al. |
| 5,525,711 A | 6/1996 | Hawkins et al. |
| 5,527,528 A | 6/1996 | Allen et al. |
| 5,534,259 A | 7/1996 | Zalipsky et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,543,152 A | 8/1996 | Webb et al. |
| 5,543,158 A | 8/1996 | Gref et al. |
| 5,545,730 A | 8/1996 | Urdea et al. |
| 5,547,932 A | 8/1996 | Curiel et al. |
| 5,550,111 A | 8/1996 | Suhadolnik et al. |
| 5,552,538 A | 9/1996 | Urdea et al. |
| 5,552,540 A | 9/1996 | Haralambidis |
| 5,556,948 A | 9/1996 | Tagawa et al. |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,575 A | 12/1996 | Unger et al. |
| 5,580,731 A | 12/1996 | Chang et al. |
| 5,583,020 A | 12/1996 | Sullivan |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,721 A | 1/1997 | Agrawal et al. |
| 5,591,722 A | 1/1997 | Montgomery et al. |
| 5,594,121 A | 1/1997 | Froehler et al. |
| 5,595,726 A | 1/1997 | Magda et al. |
| 5,595,756 A | 1/1997 | Bally et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,646,265 A | 7/1997 | McGee |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,750,692 A | 5/1998 | Cook et al. |
| 6,582,908 B2 * | 6/2003 | Fodor .............. C12Q 3/00 506/30 |

(56) References Cited

U.S. PATENT DOCUMENTS

| | | | |
|---|---|---|---|
| 7,473,414 B2 | 1/2009 | Heber-Katz | |
| 8,680,065 B2 | 3/2014 | Xu et al. | |
| 2002/0168631 A1 | 11/2002 | Park et al. | |
| 2003/0219770 A1* | 11/2003 | Eshleman | C12Q 1/6869 435/6.14 |
| 2005/0106584 A1 | 5/2005 | Ast et al. | |
| 2011/0166204 A1 | 7/2011 | Xu et al. | |
| 2012/0028817 A1* | 2/2012 | Kelly | C12Q 1/6813 506/7 |
| 2017/0183655 A1 | 6/2017 | Grabczyk et al. | |

OTHER PUBLICATIONS

Lanikova et al., "β-Thalassemia Due to Intronic LINE-1 Insertion in the β-Globin Gene (HBB): Molecular Mechanisms Underlying Reduced Transcript Levels of the B-Globin(L1) Allele," Human Mutation, Aug. 13, 2013, vol. 34, pp. 1361-1365.

Tappino et al., "An Alu insertion in compound heterozygosity with a microduplication in GNPTAB gene underlies Mucolipidosis II," Molecular Genetics and Metabolism, Oct. 26, 2007, vol. 93, pp. 129-133.

International Search Report and Written Opinion in corresponding PCT Patent Application No. PCT/US2018/050576, dated Feb. 19, 2019 (18 pages).

Fairbrother et al., "RESCUE-ESE identifies candidate exonic splicing enhancers in vertebrate exons," Nucleic Acids Research, 2004, vol. 32, Suppl. 2, pp. W187-W190.

Finkel et al., "Treatment of infantile-onset spinal muscular atrophy with nusinersen: a phase 2, open-label, dose-escalation study," The Lancet, Published Online: Dec. 6, 2016, vol. 388, No. 10063, pp. 3017-3026.

Kabanov et al., "A new class of antivirals: antisense oligonucleotides combined with a hydrophobic substituent effectively inhibit influenza virus reproduction and synthesis of virus-specific proteins in MDCK cells," FEBS Letters, Jan. 1990, vol. 259, No. 2, pp. 327-330.

Letsinger et al., "Cholesteryl-conjugated oligonucleotides: Synthesis, properties, and activity as inhibitors of replication of human immunodeficiency virus in cell culture," Proceedings of the National Academy of Sciences of the United States of America, Sep. 1989, vol. 86, pp. 6553-6556.

Moon et al., "Target site search and effective inhibition of leukaemic cell growth by a covalently closed multiple anti-sense oligonucleotide to c-myb," Biochemical Journal, 2000, vol. 346, pp. 295-303.

Moon et al., "Potent Growth Inhibition of Leukemic Cells by Novel Ribbon-type Antisense Oligonucleotides to c-myb1," The Journal of Biological Chemistry, Feb. 18, 2000, vol. 275, No. 7, pp. 4647-4653.

Nielsen et al., "Sequence-Selective Recognition of DNA by Strand Displacement with a Thymine-Substituted Polyamide," Science, Dec. 6, 1991, vol. 254, No. 5037, pp. 1497-1500.

Oberhauser et al., "Effective incorporation of 2'-O-methyl-oligoribonuclectides into liposomes and enhanced cell association through modification with thiocholesterol," Nucleic Acids Research, 1992, vol. 20, No. 3, pp. 533-538.

Saison-Behmoaras et al., "Short modified antisense oligonucleotides directed against Ha-ras point mutation induce selective cleavage of the mRNA and inhibit T24 cells proliferation," The EMBO Journal, 1991, vol. 10, No. 5, pp. 1111-1118.

Shea et al., "Synthesis, hybridization properties and antiviral activity of lipid-oligodeoxynucleotide conjugates," Nucleic Acids Research, 1990, vol. 18, No. 13, pp. 3777-3783.

Smith et al., "An increased specificity score matrix for the prediction of SF2/ASF-specific exonic splicing enhancers," Human Molecular Genetics, 2006, vol. 15, No. 16, pp. 2490-2508.

* cited by examiner

*Normal MFSD8 gene:*

Proband *MFSD8 gene:*

Native MFSD8 splicing:

After transposon insertion:

...MFSD8 gene truncation
& loss of protein function

Exon skipping drug to block the splice acceptor restoration of normal gene splicing

- Chimeric reads with intron 6 sequence fused to polyT

- Chimeric reads with intron 6 sequence fused to tandem GGGAGA repeats

- These indicate the presence of a large insertional event:

This matches the signature of a SVA retrotransposon

Normal *CLN7/MFSD8* allele

Mila's maternal *CLN7/MFSD8* allele

Sanger sequencing primers

Normal *CLN7/MFSD8* splicing and translation

Abnormal *CLN7/MFSD8* splicing and translation after SVA insertion

Lead oligos target the splice acceptor + a downstream site

5' [MOE-A][MOE-A][5Me-MOE-U][MOE-G][5Me-MOE-U][5Me-MOE-U][MOE-A][MOE-G][5Me-MOE-U][MOE-G][5Me-MOE-C][5Me-MOE-U][5Me-MOE-U][MOE-G][5Me-MOE-U] [5Me-MOE-U][MOE-G][MOE-A] [MOE-G][MOE-G][MOE-G] [5Me-MOE-C] 3'

[5Me-MOE-U] indicates 5-Methyl-2'-Methoxyethyl-uridine
[MOE-A] indicates 2'-Methoxyethyl-adenosine
[MOE-G] indicates 2'-Methoxyethyl-guanosine
[5Me-MOE-C] indicates 5-Methyl-2'-Methoxyethyl-cytidine

*FIG. 9 (cont.)*

Genomic matches of milasen/TY777 subsequences

| Length (bp) | Number of possible subsequences | Number of off-target hits | Off-target loci (hg38) | Off-target information |
|---|---|---|---|---|
| 22 | 1 | 0 | – | – |
| 21 | 2 | 0 | – | – |
| 20 | 3 | 0 | – | – |
| 19 | 4 | 0 | – | – |
| 18 | 5 | 0 | – | – |
| 17 | 6 | 0 | – | – |
| 16 | 7 | 7 | chr2:65659662-65659677<br>chr2:31196302-31196317<br>chr5:32260228-32260243<br>chr7:11518139-11518154<br>chr8:132908567-132908582<br>chr14:44054788-44054803<br>chr21:38507523-38507508 | *AC0174391.1* intronic<br>*CAPN14* intronic<br>*MTMR12* intronic<br>*THSD7A* intronic<br>*TG* intronic<br>*RP11-305B6.3* intronic<br>*ERG* intronic |

*FIG. 12*

COMPOSITIONS AND METHODS FOR TREATING TRANSPOSON ASSOCIATED DISEASES

CROSS REFERENCE TO RELATED APPLICATIONS

This application is the U.S. national phase application, pursuant to 35 U.S.C. § 371, of PCT international application Ser. No.: PCT/US2018/050576, filed Sep. 12, 2018, designating the United States and published in English, which claims the benefit of and priority to the following U.S. Provisional Application No. 62/558,036, filed Sep. 13, 2017; 62/593,649, filed Dec. 1, 2017; and 62/682,031, filed Jun. 7, 2018, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on Aug. 28, 2020, is named 167705_014204 US_SL.txt and is 631,973 bytes in size.

BACKGROUND OF THE INVENTION

Almost half of mammalian genomes contain repeat DNA sequences known as transposable elements. Many transposable elements (TE) have the ability to mobilize and change locations in the genome. Yet, the role of transposons in human health and disease is not well defined. Barbara McClintock, who discovered transposable elements in corn, proposed two main functions tor transposable elements: (1) insertional mutagens and (2) "controlling elements" that regulate the expression of nearby genes. RNA transposons (herein called retrotransposons) move via a copy-and-paste mechanism using RNA as an intermediate. Retrotransposition-mediated events in mammals are known to produce somatic alterations in the brain, as well as cancer. Current methods for detecting and treating the deleterious effects of TE insertion are required.

SUMMARY OF THE INVENTION

As described below, the present invention features antisense oligonucleotides (AONs) for the treatment of diseases and disorders associated with the deleterious effects of transposable element insertion (e.g., long interspersed nuclear element-1 (LINE-1), *Arthrobacter luteus* element (Alu), short interspersed nuclear element variable number tandem repeat *Arthrobacter luteus* element (SINE-VNTR-Alu) or (SVA), or endogenous retrovirus (ERV).

In one aspect, the invention provides one or more antisense oligonucleotides complementary to a transposable element present in an intronic sequence within a gene.

In another aspect, the invention provides a set of antisense oligonucleotides comprising 2 or more antisense oligonucleotides of any aspect delineated herein. In various embodiments, the set comprises 2-50 antisense oligonucleotides. In particular embodiments, the set comprises 5, 10 or 15 antisense oligonucleotides.

In another aspect, the invention provides a pharmaceutical composition comprising an effective amount of an antisense oligonucleotides of any aspect delineated herein or a set of antisense oligonucleotides of any aspect delineated herein in a pharmaceutically acceptable excipient.

In another aspect, the invention provides a method for treating a subject having a genetic disorder associated with the insertion of a transposable element, the method involving administering to the subject one or more antisense oligonucleotides of any aspect delineated herein.

In another aspect, the invention provides an isolated cell that is heterozygous for a mutation associated with a genetic defect, comprising a genetic mutation and a second allele comprising a retrotransposon insertion. In other embodiments, oligonucleotide therapy is used to correct undesirable splicing in recessive (homozygous), homozygous (compound heterozygous), or dominant (heterozygous) disease. In other embodiments, the cell is a fibroblast.

In another aspect, the invention provides a method of identifying an agent that inhibits a splicing event caused by a retrotransposon insertion, the method involving contacting a cell according to any aspect delineated herein, and detecting a splice product that does not comprise a retransposon sequence or fragment thereof.

In various embodiment of any aspect delineated herein, the oligonucleotide comprises a modified backbone. In various embodiments, the modified backbone comprises a 2' methoxy ethyl modification or a 2' O-methyl modification. In various embodiments the antisense oligonucleotide binds a splice acceptor site present in the LINE-1, Alu, SVA, or ERV. In various embodiments, the antisense oligonucleotide comprises or consists of a sequence listed in Table 1. In various embodiments, the antisense oligonucleotide comprises at least one modified sugar moiety, e.g., a 2'-O-methyl group or a 2'-O-methoxyethyl group. In various embodiments, the nucleobase oligomer comprises at least one modified nucleobase. In various embodiments, the oligonucleotide comprises DNA residues, RNA residues, modified DNA or RNA residues, or combinations of any of these.

In various embodiment of any aspect delineated herein, the subject or cell is heterozygous for a mutation associated with a genetic defect. In various embodiment of any aspect delineated herein, the subject or cell comprises a first allele comprising a genetic mutation and a second allele comprising a retrotransposon insertion. In various embodiment of any aspect delineated herein, the transposable element is a retrotransposon. In various embodiments, the retrotransposon is LINE-1, Alu, SVA, or ERV.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By a "nucleobase oligomer" is meant a compound that includes a chain of at least eight nucleobases joined together by linkage groups. Included in this definition are natural and non-natural oligonucleotides, both modified and unmodified, as well as oligonucleotide mimetics such as Protein Nucleic Acids, locked nucleic acids, and arabinonucleic acids. Numerous nucleobases and linkage groups may be employed in the nucleobase oligomers of the invention, including those described in detail herein in the section entitled "Oligonucleotides and other nucleobase oligomers," infra "Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "promoter" is meant a polynucleotide sufficient to direct transcription.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

Transposable elements are known in the art. The following exemplary sequences are provided for SVA transposons.

An "SVA transposon" comprises the Sequence of any of SVA1-6 or has at least about 85% identity to such sequence.

SVA1
CTCTCCCTCTCCCTCTCCCTCTCCCTCTCCCTCTCCCTCTCCCT
CTTTCTACGGTCTCCCTCTGTTGCCGAGGCTGGACTGTACTGCCGTGATCT
CGGCTCGCTGCAACCTCCCTGCCTCGGGCTCCAGTGATTCTCCTGCCTCGG
CCTGCCGAGTGCCTGGGATTGCAGGCACGCGCCGCCACGCCTGACTGGTTT
TTGTATTTTTGGTGGAGACGGGGTTTCGCTGTGTTGACCGGGCTGGTCTCC
AGCTCCTGGCCTCGAGTGATCTGCCCGCCTCGGCCTCCCGAGGTGCTGGGA
TTGCAGACGGAGTCTCGCTCACTCAGTGCTCAATGTTGCCCAGGCTGGAGT
GCAGTGGCGTGATCTCGGCTCGCTACAACCTCCACCTCCCAGCCGCCTGCC
TTGGCCTCCCAAAGTGCTAAGATTGCAGCCTCTGCCCGGCCGCCACCCCGT
CTGGGAAGTGAGGAGCGTCTCTGCCTGGCCGCCCATCGTCTGGGATGTGAG
GAGCCCCTCTGCCCGGCCGCCCCGTCTGGGAAGTGAGGAGCGCCTCTGCCC
GGCCGCCACCCCGTCTGGGAAGTGAGGAGCGTCTCTGCCCGGCCGCCCATC
GTCTGGGATGTGAGGAGCGCCTCTGCCCGGCCGCCCCGTCTGGGATGTGAG
GAGCGCCTCTGCCCGGCCAGCCGCCCCGTCTGGGAGGTGGGGGGTCAGCC
CCCCGCCCGGCCAGCCGCCCCGTCTGGGAGGAGGTGGGGGGGTCAGCCCCC
CGCCCGGCCAGCCGCCCCGTCTGGGAGGTGAGGGGCGCCTCTGCCCGGCCG
CCCCTTCTGGGAAGTGAGGAGCCCCTCTGCCCGGCCACCGCCCCGTCTGGG
AGGTGTACCCAGCGACCATTGAGAACGGGCCATGATGACGATGGCGGTTTT
GTCGAAAAGAAAAGGGGGAAATGTGGGAAAAGAAAGAGAGATCAGATTGT
TACTGTGTCTGTGTAGAAAGAAGTAGACATAGGAGACTCCATTTTGTTCTG
TACTAAGAAAAATTCTTCTGCCTTGGGATGCTGTTAATCTATAACCTTACC
CCCAACCCCGTGCTCTCTGAAACATGTGCTGTGTCAACTCAGGGTTAAATG
GATTAAGGGCGGTGCAAGATGTGCTTTGTTAAACAGATGCTTGAAGGCAGC
ATGCTCGTTAAGAGTCATCACCACTCCCTAATCTCAAGTACCCAGGGACAC
AAACACTGCGGAAGGCCGCAGGGACCTCTGCCTAGGAAAACCAGAGACCTT

TGTTCACGTGTTTATCTGCTGACCTTCTCTCCACTATTATCCTATGACCCT
GCCACATCCCCCTCTCCGAGAAACACCCAAGAATGATCAATAAATACTAAA
AAAAAAAAAA

SVA2
CTCTCCCTCTCCCTCTCCCTCTCCCTCTCCCTCTCCCTCTCCCTGTCCCCT
CTTTCCACGGTCTCCCTCTGATGCCGAGCCGAGGCTGGACTGTACTGCCGC
CATCTCGGCTCACTGCAACCTCCCTGCCTGATTCTCCTGCCTCAGCCTGCC
GAGTGCCTGGGATTGCAGGCGCGCGCCGCCACGCCTGACTGGTTTTTGTAT
TTTTTGGTGGAGACGGGGTTTCGCCGTGTTGGCCGGGCTGGTCTCCAGCTC
CTGACCGCGAGTGATCTGCCCGCCTCGGCCTCCCGAGGTGCCGGGATTGCA
GACGGAGTCTCGCTCACTCAGTGCTCAATGTTGCCCAGGCTGGAGTGCAGT
GGCGTGATCTCGGCTCGCTACAACCTCCACCTCCCAGCCGCCTGCCTTGGC
CTCCCAAAGTGCCGAGATTGCAGCCTCTGCCCGGCCGCCACCCCGTCTGGG
AAGTGAGGAGCGTCTCTGCCTGGCCGCCCATCGTCTGGGATGTGAGGAGCC
CCTCTGCCCGGCCGCCCAGTCTGGGAAGTGAGGAGCGCCTCTTCCCGGCCG
CCATCCCGTCTGGGAAGTGAGGAGCGTCTCTGCCCGGCCGCCCATCGTCTG
GGATGTGGGGAGCGCCTCTGCCCCGCCGCCCCGTCTGGGATGTGAGGAGCG
CCTCTGCCCGGCCAGCCGCCCCGTCTGGGAGGTGGGGGGTCAGCCCCCCG
CCCGGCCAGCCGCCCCGTCCGGGAGGAGGTGGGGGGGTCAGCCCCCCGCCC
GGCCAGCCGCCCCGTCTGGGAGGTGGGGGGCGCCTCTGCCCGGCCGCCCCG
TCTGGGAAGTGAGGAGCCCCTCTGCCCGGCCGCCACCCCGTCTGGGAGGTG
TACCCAACAGCTCATTGAGAACGGGCCATGATGACGATGGCGGTTTTGTCG
AATAGAAAAGGGGGAAATGTGGGGAAAAGAAAGAGAGATCAGATTGTTACT
GTGTCTGTGTAGAAAGAAGTAGACATAGGAGACTCCATTTTGTTCTGTACT
AAGAAAAATTCTTCTGCCTTGGGATGCTGTTAATCTATAACCTTACCCCCA
ACCCCGTGCTCTCTGAAACATGTGCTGTGTCCACTCAGGGTTAAATGGATT
AAGGGCGGTGCAAGATGTGCTTTGTTAAACAGATGCTTGAAGGCAGCATGC
TCGTTAAGAGTCATCACCACTCCCTAATCTCAAGTACCCAGGGACACAAAC
ACTGCGGAAGGCCGCAGGGTCCTCTGCCTAGGAAAACCAGAGACCTTTGTT
CACATGTTTATCTGCTGACCTTCCCTCCACTATTGTCCTATGACCCTGCCA
AATCCCCTCTCCGAGAAACACCCAAGAATGATCAATAAATACTAAAAAAA
AAAAAA

SVA3
CTCTCCCTCTCCCTCTCCCTCTCCCTCTCCCTCTCCCTCTCCCTCTCCCCT
CTTTCCACGGTCTCCCTCTGATGCCGAGCCGAAGCTGGACTGTACTGCTGC
CATCTCGGCTCACTGCAACCTCCCTGCCTGATTCTCCTGCCTCAGCCTGCC
GAGTGCCTGCGATTGCAGGCGCGCGCCGCCACGCCTGACTGGTTTTCGTAT
TTTTTGGTGGAGACGGGGTTTCGCTGTGTTGGCCGGGCTGGTCTCCAGCT
CCTAACCGCGAGTGATCGCCAGCCTCGGCCTCCCGAGGTGCCGGGATTGC
AGACGGAGTCTCGTTCACTCAGTGCTCAATGTTGCCCAGGCTGGAGTGCAG
TGGCGTGATCTCGGCTCGCTACAACCTCCACCTCCCAGCCGCCTGCCTTGG

```
CCTCCCAAAGTGCCGAGATTGCAGCCTCTGCCCGGCCGCCACCCCGTCTGG
GAAGTGAGGAGCGTCTCTGCCTGGCCGCCCATCGTCTGGGATGTGAGGAGC
CCCTCTGCCTGGCTGCCCAGTCTGGGAAGTGAGGAGCGCCTCTTCCCGGCC
GCCATCCCGTCTAGGAAGTGAGGAGCGTCTCTGCCCGGCCGCCCATCGTCT
GAGATGTGGGGAGCGCCTCTGCCCCGCCGCCCCGTCTGGGATGTGAGGAGC
GCCTCTGCCCGGCCAGCCGCCCCGTCTGGGAGGTGGGGGGGTCAGCCCCCC
GCCCGGCCAGCCGCCCCGTCCGGGAGGAGGTGGGGGGGTCAGCCCCCCGCC
CGGCCAGCCGCCCCGTCCGGGAGGTGGGGGGCGCCTCTGCCCGGCCGCCCC
TTCTGGGAAGTGAGGAGCCCCTCTGCCCGGCCACCACCCCGTCTGGGAGGT
GTACCCAACAGCTCATTGAGAACGGGCCATGATGACGATGGCGGTTTTGTG
GAATAGAAAGGGGGGAAAGGTGGGGAAAAGATAGAGAAATCGGATTGTTGC
TGTGTCTGTGTAGAAAGAAGTAGACATGGGAGACTTCATTTTGTTCTGTAC
TAAGAAAAATTCTTCTGCCTTGGGATGCTGTTGATCTGTGACCTTACCCCC
AACCCTGTGCTCTCTGAAACATGTGCTGTGTCCACTCAGGGTTAAATGGAT
TAAGGGCGGTGCAAGATGTGCTTTGTTAAACAGATGCTTGAAGGCAGCATG
CTCGTTAAGAGTCATCACCACTCCCTAATCTCAAGTACCCAGGGACACAAA
CACTGCGGAAGGCCGCAGGGTCCTCTGCCTAGGAAAACCAGAGACCTTTGT
TCACTTGTTTATCTGCTGACCTTCCCTCCACTATTGTCCTATGACCCTGCC
AAATCCCCCTCTGCGAGAAACACCCAAGAATGATCAATAAAAAAAAAAAAA
AAAAAAA
SVA4
CTCTCCCTCTCCCTCTCCCTCTCCCTCTCCCTCTCCCTCTCCCTCTCCCT
CTTTCCACGGTCTCCCTCTGATGCCGAGCCGAAGCTGGACTGTACTGCTGC
CATCTCGGCTCACTGCAACCTCCCTGCCTGATTCTCCTGCCTCAGCCTGCC
GAGTGCCTGCGATTGCAGGCGCGCGCCGCCACGCCTGACTGGTTTTCGTAT
TTTTTTGGTGGAGACGGGGTTTCGCTGTGTTGGCCGGGCTGGTCTCCAGCT
CCTAACCGCGAGTGATCCGCCAGCCTCGGCCTCCCGAGGTGCCGGGATTGC
AGACGGAGTCTGGTTCACTCAGTGCTCAATGGTGCCCAGGCTGGAGTGCAG
TGGCGTGATCTCGGCTCGCTACAACCTCCACCTCCCAGCCGCCTGCCTTGG
CCTCCCAAAGTGCCGAGATTGCAGCCTCTGCCCGGCCGCCACCCCGTCTGG
GAAGTGAGGAGCGTCTCTGCCTGGCCGCCCATCGTCTGGGATGTGAGGAGC
CCCTCTGCCTGGCTGCCCAGTCTGGGAAGTGAGGAGCGTCTCTGCCCGGCC
GCCATCCCATCTAGGAAGTGAGGAGCGTCTCTGCCCGGCCGCCCATCGTCT
GAGATGTGGGGAGCGCCTCTGCCCCGCCGCCCCGTCTGGGATGTGAGGAGC
GCCTCTGCCCGGCCAGCCGCCCCGTCTGGGAGGTGGGGGGGTCAGCCCCCC
GCCCGGCCAGCCGCCCCGTCCGGGAGGAGGTGGGGGGGTCAGCCCCCCGCC
CGGCCAGCCGCCCCGTCCGGGAGGTGAGGGGCGCCTCTGCCCGGCCGCCCC
TACTGGGAAGTGAGGAGCCCCTCTGCCCGGCCACCACCCCGTCTGGGAGGT
GTACCCAACAGCTCATTGAGAACGGGCCATGATGACGATGGCGGTTTTGTG
GAATAGAAAGGGGGGAAAGGTGGGGAAAAGATTGAGAAATCGGATGGTTGC
CGTGTCTGTGTAGAAAGAGGTAGACATGGGAGACTTTTCATTTTGTTCTGT
ACTAAGAAAAATTCTTCTGCCTTGGGATCCTGTTGATCTGTGACCTTACCC
CCAACCCTGTGCTCTCTGAAACATGTGCTGTGTCCACTCAGGGTTAAATGG
ATTAAGGGCGGTGCAAGATGTGCTTTGTTAAACAGATGCTTGAAGGCAGCA
TGCTCGTTAAGAGTCATCACCACTCCCTAATCTCAAGTACCCAGGGACACA
AACACTGCGGAAGGCCGCAGGGTCCTCTGCCTAGGAAAACCAGAGACCTTT
GTTCACTTGTTTATCTGCTGACCTTCCCTCCACTATTGTCCTATGACCCTG
CCAAATCCCCCTCTGCGAGAAACACCCAAGAATGATCAATAAAAAAAAAAA
AAAAAAAA
SVA5
CTCTCCCTCTCCCTCTCCCTCTCCCTCTCCCTCTCCCTCTCCCTCTCCCT
CTCTCCACGGTCTCCCTCTGATGCCGAGCCAAAGCTGGACGGTACTGCTGC
CATCTCGGCTCACTGCAACCTCCCTGCCTGATTCTCCTGCCTCAGCCTGCC
GAGTGCCTGCGATTGCAGGCGCGCGCCGCCACGCCTGACTGGTTTTCGTTT
TTTTTTGGTGGAGACGGGGTTTCGCTGTGTTGGCCGGGCTGGTCTCCAGCT
CCTAACCGCGAGTGATCCGCCAGCCTCGGCCTCCCGAGGTGCCGGGATTGC
AGACGGAGTCTCGTTCACTCAGTGCTCAATGGTGCCCAGGCTGGAGTGCAG
TGGCGTGATCTCGGCTCGCTACAACCACCTCCCAGCCGCCTGCCTTGGCCT
CCCAAAGAGCCGGATTGCAGCCTCTGCCCGGCCGCCACCCCGTCTGGGAAG
TGAGGAGCGTCTCTGCCTGGCCGCCCATCGTCTGGGATGTGAGGAGCCCCT
CTGCCTGGCCGCCCAGTCTGGGAAGTGAGGAGCGCCTCTGCCCGGCCGCCA
TCCCGTCTGGGAAGTGAGGAGCGTCTCTGCCCGGCCGCCCATCGTCTGGGA
TGTGGGGAGCACCTCTGCCCCGCCGCCCCGTCTGGGATGTGAGGAGCGCCT
CTGCCCGGCCAGCCGCCCCGTCCGGGAGGTGGGGGGGTCAGCCCCCCGCCC
GGCCAGCCGCCCCGTCCGGGAGGAGGTGGGGGGGTCAGCCCCCCGCCCGGC
CAGCCGCCCCGTCCGGGAGGTGAGGGGCGCCTCTGCCCGGCCGCCCCTACT
GGGAAGTGAGGAGCCCCTCTGCCCGGCCACCGCCCCGTCTGGGAGGTGTGC
CCAGCGGCTCATTGGGATGGGCCATGATGACAATGGCGGTTTTGTGGAAT
AGAAAGGCGGGAAGGGTGGGAAAAAATTGAGAAATCGGATGGTTGCCGGG
TCTGTGTGGATAGAAGTAGACATGGGAGACTTTTCATTTTGTTCTGTACTA
AGAAAAATTCTTCTGCCTTGGGATCCTGTTGATCTGTGACCTTATCCCCAA
CCCTGTGCTCTCTGAAACATGTGCTGTGTCCACTCAGGGTTAAATGGATTA
AGGGCGGTGCAAGATGTGCTTTGTTAAACAGATGCTTGAAGGCAGCATGCT
CGTTAAGAGTCATCACCACTCCCTAATCTTAAGTACCCAGGGACACAAACA
CTGCGGAAGGCCGCAGGGTCCTCTGCCTAGGAAAACCAGAGACCTTTGTTC
ACTTGTTTATCTGCTGACCTTCCCTCCACTATTGTCCTATGACCCTGCCAA
ATCCCCCTCTGCGAGAAACACCCAAGAATGATCAATAAAAAAAAAAAAAAA
AAAAA
SVA6
CTCTCCCTCTCCCTCTCCCTCTCCCTCTCCCTCTCCCTCTCCCTCTCCCT
CTTTCCACGGTCTCCCTCTCATGCGGAGCCGAAGCTGGACTGTACTGCTGC
CATCTCGGCTCACTGCAACCTCCCTGCCTGATTCTCCTGCCTCAGCCTGCC
GAGTGCCTGCGATTGCAGGCACGCGCCGCCACGCCTGACTGGTTTTGGTGG
```

-continued

```
AGACGGGGTTTCGCTGTGTTGGCCGGGCCGGTCTCCAGCCCCTAACCGCGA
GTGATCCGCCAGCCTCGGCCTCCCGAGGTGCCGGGATTGCAGACGGAGTCT
CGTTCACTCAGTGCTCAATGGTGCCCAGGCTGGAGTGCAGTGGCGTGATCT
CGGCTCGCTACAACCTACACCTCCCAGCCGCCTGCCTTGGCCTCCCAAAGT
GCCGAGATTGCAGCCTCTGCCCGGCCGCCACCCCGTCTGGGAAGTGAGGAG
CGTCTCTGCCTGGCCGCCCATCGTCTGGGATGTGAGGAGCCCCTCTGCCCG
GCCGCCCAGTCTGGGAAGTGAGGAGCGCCTCCGCCCGGCCGCCATCCCGTC
TGGGAAGTGAGGAGCGTCTCTGCCCGGCCGCCCATCGTCTGAGATGTGGGG
AGCGCCTCTGCCCCGCCGCCCCGTCTGGGATGTGAGGAGCGCCTCTGCCCG
GCCAGCCGCCCCGTCTGGGAGGTGGGGGGGTCAGCCCCCCGCCCGGCCAGC
CGCCCCGTCCGGGAGGAGGTGGGGGGGTCAGCCCCCCGCCCGGCCAGCCGC
CCCGTCCGGGAGGTGAGGGGCGCCTCTGCCCGGCCGCCCCTACTGGGAAGT
GAGGAGCCCCTCTGCCCGGCCACCACCCCGTCTGGGAGGTGTGCCCAACAG
CTCATTGAGAACGGGCCAGGATGACAATGGCGGCTTTGTGGAATAGAAAGG
CGGGAAAGGTGGGGAAAAGATTGAGAAATCGGATGGTTGCCGTGTCTGTGT
AGAAAGAAGTAGACATGGGAGACTTTTCATTTTGTTCTGTACTAAGAAAAA
TTCTTCTGCCTTGGGATCCTGTTGATCTGTGACCTTACCCCCAACCCTGTG
CTCTCTGAAACATGTGCTGTGTCCACTCAGGGTTAAATGGATTAAGGGCGG
TGCAAGATGTGCTTTGTTAAACAGATGCTTGAAGGCAGCATGCTCGTTAAG
AGTCATCACCACTCCCTAATCTCAAGTAATCAGGGACACAAACACTGCGGA
AGGCCGCAGGGTCCTCTGCCTAGGAAAACCAGAGACCTTTGTTCACTTGTT
TATCTGCTGACCTTCCCTCCACTATTGTCCCATGACCCTGCCAAATCCCCC
TCTGTGAGAAACACCCAAGAATTATCAATAAAAAAAATTAAAAAAAAA
```

By "antisense oligonucleotide" is meant a nucleobase oligomer that is complementary to a target sequence. The antisense oligonucleotide may contain modified bases, a modified backbone, or any other modification described herein or known in the art. Table 1 provides a list of antisense oligonucleotide (also termed an "AON") directed against an SVA. Such AONs are useful for targeting an SVA present in a human genome.

TABLE 1

Library of Antisense Oligonucleotides Targeting SVA

| | | |
|---|---|---|
| GGGAGGTGGGGGCG | GTGATCTGCCCGCCT | CACCCCGTCTGGGAG |
| CTGACCTTCCCTCCA | GCAAGATGTGCTTTG | AGATAGAGAAATCGG |
| GTCCTCTGCCTAGGA | GGCGTGATCTCGGCT | AGAGAAATCGGATTG |
| GGAAGTGAGGAGCCC | CCTGATTCTCCTGCC | TCCCTCCACTATTGT |
| TACTAAAAAAAAAAA | GCCAGGATGACAATG | AATTGAGAAATCGGA |
| GGGATGCTGTTAATC | ATTGCAGGCGCGCGC | CCCATGACCCTGCCA |
| CACGCGCCGCCACGC | TGCGGAGCCGAAGCT | TGCAAGATGTGCTTT |
| TCTCCAGCTCCTGAC | CAACCTCCCTGCCTG | TACCCAGCGACCATT |
| CGTCCGGGAGGTGGG | TGCTGGGATTGCAGA | GTTGCTGTGTCTGTG |

TABLE 1-continued

Library of Antisense Oligonucleotides Targeting SVA

| | | |
|---|---|---|
| CTGTGTTGGCCGGGC | CAACCTCCCTGCCTC | AGGGACCTCTGCCTA |
| TCTCTGCCTGGCCGC | ACAGCTCATTGAGAA | AGGTGCTGGGATTGC |
| GATTGCAGGCGCGCG | CGCCATCCCATCTAG | TCTGGGAGGTGGGGG |
| TGGGGAAAAGATAGA | TTCATTTGTTCTGT | CTGGGAGGTGTGCCC |
| TGCCCAGGCTGGAGT | AGCCCCTCTGCCTGG | GTTCACATGTTTATC |
| ATGACAATGGCGGTT | TCTCCGAGAAACACC | CAAAGTGCCGAGATT |
| GGTTTTCGTTTTTTT | GGCCGCAGGGTCCTC | TCTGAGATGTGGGGA |
| GGCGCCTCTGCCCGG | CGCCCCTTCTGGGAA | TGGGATTGCAGGCAC |
| AACGGGCCAGGATGA | CTCCCCTCTTTCTAC | CTGCCGTGATCTCGG |
| GCGCCTCTGCCCGGC | CAATAAATACTAAAA | AATGGCGGTTTTGTG |
| TCCGGGAGGTGAGGG | ATGGCGGTTTTGTGG | TGACCCTGCCAAATC |
| CTAAAAAAAAAAAAA | ATTGCAGGCACGCGC | TGATCAATAAATACT |
| CCGTGTTGGCCGGGC | TCACGTGTTTATCTG | AGTGCCGAGATTGCA |
| AATAAAAAAAATTAA | AAGAGGTAGACATGG | AGGCCGCAGGGACCT |
| GCCAGCCTCGGCCTC | TTAAGTACCCAGGGA | CCTCTGCCTAGGAAA |
| GGCCACCACCCCGTC | CGGGCTCCAGTGATT | GCCCCTCTGCCCGGC |
| ATGATGACAATGGCG | GGGATGTGGGGAGCG | TCTGGGAGGTGAGGG |
| CTAATCTTAAGTACC | GGGATGTGGGGAGCA | TCATTTTGTTCTGTA |
| ATGCCGAGCCGAGGC | AGACTTCATTTTGTT | CGCCTCGGCCTCCCG |
| CTCGCTACAACCTCC | GTATTTTTTGGTGG | TAAGGGCGGTGCAAG |
| TGATGCCGAGCCAAA | ATCGTCTGGGATGTG | CCAAGAATGATCAAT |
| CACGCCTGACTGGTT | GCGCCTCTTCCCGGC | GACCGGGCTGGTCTC |
| GGAAAAGATTGAGAA | ACAAACACTGCGGAA | GCTGTTAATCTATAA |
| CTGCCTTGGCCTCCC | CCCATCGTCTGAGAT | CTTCTGGGAAGTGAG |
| GCTGACCTTCTCTCC | GAGACTTCATTTGT | AGAAAGGCGGGAAAG |
| GCCCAGGCTGGAGTG | TTAAGAGTCATCACC | AGTCTCGCTCACTCA |
| GTTTCGCTGTGTTGA | GGGCGCCTCTGCCCG | GTCTAGGAAGTGAGG |
| CTCCATTTTGTTCTG | CTCACTGCAACCTCC | TGGGATTGCAGACGG |
| GTTTCGCTGTGTTGG | ATCGTCTGAGATGTG | AGAGTCATCACCACT |
| CTCTCCACTATTATC | CCGGCCGCCCAGTCT | GATGCTGTTGATCTG |
| GTCTGTGTGGATAGA | TGAGATGTGGGGAGC | CCCCGCCGCCCCGTC |
| TTTCGTATTTTTTTG | GCTGCCATCTCGGCT | GGGCCATGATGACGA |
| CTTTGTTCACTTGTT | AGTGGCGTGATCTCG | AAGCTGGACTGTACT |
| ACAACCTACACCTCC | CGCCTGCCTTGGCCT | GCAGACGGAGTCTCG |
| GTGATTCTCCTGCCT | GCTGTGTCCACTCAG | TCTGCCCGGCCGCCA |
| GGTTAAATGGATTAA | CTCTTCCCGGCCGCC | TCTGCCCGGCCGCCC |
| CTGCCAAATCCCCCT | GCCGCCACGCCTGAC | GGATGTGAGGAGCCC |
| CCTAACCGCGAGTGA | TTTTTTTGGTGGAGA | GGGAAGTGAGGAGCG |
| CAACTCAGGGTTAAA | CTCCCTGTCCCCTCT | GGGAAGTGAGGAGCC |

TABLE 1-continued

Library of Antisense Oligonucleotides Targeting SVA

| | | |
|---|---|---|
| AAAGTGCCGAGATTG | TTACCCCCAACCCTG | TCCACCTCCCAGCCG |
| AGAATGATCAATAAA | TGTGGATAGAAGTAG | GTGGGGAAAAGATAG |
| TGACCTTATCCCCAA | CTACAACCACCTCCC | CTAAGATTGCAGCCT |
| TCTGCTGACCTTCTC | GTTTATCTGCTGACC | TGAAGGCAGCATGCT |
| AAAGGCGGGAAAGGT | GGGGATGGGCCATGA | GCTGGACTGTACTGC |
| GGTCTGTGTGGATAG | GACTTCATTTTGTTC | CACTGCGGAAGGCCG |
| ACGGTCTCCCTCTCA | TGGCGGTTTTGTGGA | GAGGAGCGCCTCTTC |
| GTGATCTCGGCTCGC | CCGCCCAGTCTGGGA | TCGAAAAGAAAAGGG |
| GTAGAAAGAGGTAGA | CTCCCAGCCGCCTGC | TTTGTTAAACAGATG |
| TCTGCCTGGCTGCCC | GCTCGCTACAACCAC | CTGACTGGTTTTGGT |
| CGATTGCAGGCGCGC | CACCCCGTCTGGGAA | TTGCAGGCACGCGCC |
| ATTGAGAAATCGGAT | GGGAGCGCCTCTGCC | TCTGTTGCCGAGGCT |
| CGCCTCTGCCCCGCC | GTGGAATAGAAAGGC | AGAGAGATCAGATTG |
| ACCCAGCGACCATTG | TCTCGGCTCACTGCA | CTCGGCCTCCCGAGG |
| AGCGTCTCTGCCCGG | GTGGAATAGAAAGGG | TGGCGTGATCTCGGC |
| CCTAATCTTAAGTAC | GGGAGGAGGTGGGG | GCCTCCGCCCGGCCG |
| AAAGATTGAGAAATC | TTTGTATTTTGGTG | TCTCCCTCTCCCTCT |
| CGAGTGATCCGCCAG | GGTGCCCAGGCTGGA | TCAGGGTTAAATGGA |
| CCATCTAGGAAGTGA | TATTTTTTGGTGGA | CTGTGAGAAACACCC |
| GAAAGAGGTAGACAT | CCGCCTCGGCCTCCC | CCGAGTGCCTGCGAT |
| TTGGCCGGGCCGGTC | TGCCGGGTCTGTGTG | CCCTCCACTATTGTC |
| GGAGACGGGGTTTCG | GAATAGAAAGGGGGG | CCTCTCCCCTCTTTC |
| CCGCGAGTGATCCGC | TCAAGTACCCAGGGA | CAATGGCGGCTTTGT |
| TAGAAAGGGGGGAAA | GGTAGACATGGGAGA | CGCCTCTGCCCGGCC |
| GCCTCTTCCCGGCCG | ACATGTGCTGTGTCC | GAAACATGTGCTGTG |
| AAAGATAGAGAAATC | ACATGTGCTGTGTCA | CCCCCAACCCTGTGC |
| GCCGGTCTCCAGCCC | CGGAGTCTGGTTCAC | GAGTCTCGCTCACTC |
| CGGTTTTGTCGAAAA | CGTATTTTTTGGTG | TGGTGGAGACGGGGT |
| CTTTGTTAAACAGAT | ACCCCCAACCCCGTG | GGTCTCCCTCTGTTG |
| CAGCTCCTAACCGCG | CCTGCCTGATTCTCC | AAACACTGCGGAAGG |
| TTCACTTGTTTATCT | CGTCTGGGAGGTGTG | GGCCGCCATCCCGTC |
| CTCGCTACAACCACC | CGTCTGGGAGGTGTA | CAGACGGAGTCTCGT |
| CCTCCCAGCCGCCTG | TCTGCGAGAAACACC | GCTCATTGGGGATGG |
| TCCCTAATCTCAAGT | TTGAGAACGGGCCAT | CATCACCACTCCCTA |
| CTGCCTGATTCTCCT | CCCCCTCTGCGAGAA | TCTCCCTCTCCCCTC |
| TGCCTGCGATTGCAG | CATTGGGGATGGCC | CAGACGGAGTCTCGC |
| GCTCACTCAGTGCTC | GCGGGAAGGGTGGGG | AAGGGTGGGAAAAA |
| TCTCGGCTCGCTACA | GTACCCAGGGACACA | TTCTGGGAAGTGAGG |
| GCCGCCATCTCGGCT | GCGCCTCTGCCCCGC | CCTGCCACATCCCCC |
| GCTCCTAACCGCGAG | TTTCGCCGTGTTGGC | CTGCCCAGTCTGGGA |
| TAGGAAAACCAGAGA | TGTACTGCCGTGATC | ACCTTACCCCCAACC |
| CTCGCTCACTCAGTG | ACCTCCCTGCCTCGG | CGCCATCCCGTCTGG |
| CCTCTTTCTACGGTC | ATTTTTTGGTGGAGA | CTCTGCCCGGCCGCC |
| TCGCTGCAACCTCCC | CTATGACCCTGCCAC | AGGAGGTGGGGGGT |
| AGCACCTCTGCCCCG | CTTGTTTATCTGCTG | CTCCCGAGGTGCCGG |
| AAGTGAGGAGCGTCT | CTATGACCCTGCCAA | CGAAGCTGGACTGTA |
| AGGGGGAAATGTGGG | TAAAAAAAAAAAAAA | GTTGGCCGGGCTGGT |
| GCCTTGGGATCCTGT | CGCTACAACCTACAC | TAGAAAGGGGGAAA |
| CATCTAGGAAGTGAG | GTCCACTCAGGGTTA | GGCTGGAGTGCAGTG |
| ATCTGTGACCTTATC | GCAGGGTCCTCTGCC | CCCTGCCTCGGGCTC |
| GGGGGGGTCAGCCCC | CCCCTCTTTCCACGG | GTCTGGGATGTGGGG |
| GTGTTTATCTGCTGA | GTCTGGGAGGTGAGG | CTGTGTCAACTCAGG |
| GGAAAACCAGAGACC | TGGGGATGGGCCATG | GCCGTGTTGGCCGGG |
| GCATGCTCGTTAAGA | GGTGTACCCAGCGAC | CACTATTATCCTATG |
| AAAAGATTGAGAAAT | GCTGACCTTCCCTCC | CCCCTCTCCGAGAAA |
| AAGTGAGGAGCGCCT | CCGCGAGTGATCTGC | CGGCTCGCTACAACC |
| ACCTTCTCTCCACTA | CGGCCGCCCCTTCTG | GTCTGGGATGTGAGG |
| AGACTTTTCATTTTG | GATTGAGAAATCGGA | GACATGGGAGACTTT |
| CTCGGCTCGCTACAA | AGTGCCTGGGATTGC | CCCCTCTTTCTACGG |
| CTCCAGCCCCTAACC | CTGAGATGTGGGGAG | GAAGGCCGCAGGGAC |
| AGGTAGACATGGGAG | AGAAGTAGACATGGG | AGGATGACAATGGCG |
| TCCCGAGGTGCTGGG | CGCCCATCGTCTGGG | GACATGGGAGACTTC |
| CCTCGAGTGATCTGC | TGCCCGGCCGCCCAG | CCACCACCCCGTCTG |
| GGTTCACTCAGTGCT | TCAATAAAAAAAAA | GGGAGGTGTGCCCAA |
| CAGCCTCGGCCTCCC | GTCGAATAGAAAGG | GCCCGCCTCGGCCTC |
| AAGGCCGCAGGGTCC | CTCCCTCTCCCCTCT | GGGAGGTGTGCCCAG |
| GTACTAAGAAAAATT | TGCCCGGCCGCCCAT | ATCTGTGACCTTACC |
| AAGATGTGCTTTGTT | TTGAGAACGGGCCAG | TATAACCTTACCCCC |
| AATCCCCTCTGCGA | AGCTGGACGGTACTG | CATGCTCGTTAAGAG |
| TGACCCTGCCACATC | TGTATTTTTGGTGGA | GCGTCTCTGCCTGGC |
| GCCTCTGCCCCGCCG | AAGAATGATCAATAA | GGGTCTGTGTGGATA |
| TGGGATGTGAGGAGC | CTAATCTCAAGTAAT | CGTCCGGGAGGTGAG |
| TTCCACGGTCTCCCT | GATCCTGTTGATCTG | ACGGTCTCCCTCTGT |
| CTGCCTAGGAAAACC | TCGGCTCGCTGCAAC | ATGGTGCCCAGGCTG |
| GGCCGGTCTCCAGCC | CGCCATCTCGGCTCA | TGGGAGGTGTACCCA |
| CCTTATCCCCAACCC | AAGAAGTAGACATAG | TCTGCCCGGCCAGCC |
| CGGCTCACTGCAACC | CTCCAGCTCCTGGCC | CCCTGTCCCCTCTTT |

TABLE 1-continued

Library of Antisense Oligonucleotides Targeting SVA

| | | |
|---|---|---|
| TCTGCCTGGCCGCCC | AAAAGGGGGAAATGT | TGACCTTACCCCCAA |
| TCGTTTTTTTTTGGT | ACTGCGGAAGGCCGC | ACGGTCTCCCTCTGA |
| CAATGGCGGTTTTGT | CCGTGATCTCGGCTC | CCTTTGTTCACGTGT |
| CGAGAAACACCCAAG | TGTGTCCACTCAGGG | TGTACTGCTGCCATC |
| GTGTTGACCGGGCTG | CGTGTTTATCTGCTG | TGGGATTGCAGGCGC |
| AGACGGAGTCTCGCT | ATTTTTGGTGGAGAC | CCCCTCTGTGAGAAA |
| CCCTGCCAAATCCCC | AGACCTTTGTTCACA | TTTGGTGGAGACGGG |
| CTCCTGACCGCGAGT | AGACCTTTGTTCACG | AACCTCCCTGCCTCG |
| AGGGGGGAAAGGTGG | GGATTGCAGACGGAG | CCTGACTGGTTTTGG |
| CCCGGCCGCCCCTAC | CCCAACCCCGTGCTC | CCACGGTCTCCCTCT |
| TCAGTGCTCAATGTT | AGCTCCTGGCCTCGA | GCGGCTCATTGGGGA |
| GCCGAGGCTGGACTG | TAGAAAGAAGTAGAC | ACTTCATTTTGTTCT |
| TGGCCTCCCAAAGTG | CTCCAGTGATTCTCC | CCTCCCTGCCTCGGG |
| CTCGAGTGATCTGCC | CTGCCCGGCCACCGC | GGGATTGCAGGCACG |
| TCGTTCACTCAGTGC | ATCTCAAGTAATCAG | TGTCCTATGACCCTG |
| CTCCCCTCTCTCCAC | GATGGCGGTTTTGTC | GCCCAGTCTGGGAAG |
| CCAGCGACCATTGAG | GATGGCGGTTTTGTG | CGTCTGGGAGGTGGG |
| CCAGGATGACAATGG | AAGTACCCAGGGACA | TCTTAAGTACCCAGG |
| CTGCTGCCATCTCGG | TCCTGGCCTCGAGTG | AGAAAGAGGTAGACA |
| TCCCATCTAGGAAGT | CGTTAAGAGTCATCA | TGTTGACCGGGCTGG |
| CCATGATGACGATGG | ACAATGGCGGCTTTG | CAGCCGCCTGCCTTG |
| GCAGGGACCTCTGCC | GGATGCTGTTGATCT | ATAAATACTAAAAAA |
| CCCGGCCGCCCCGTC | GTGTAGAAAGAGGTA | CCAACCCCGTGCTCT |
| ATCTTAAGTACCCAG | AAGATTGAGAAATCG | GATCTGCCCGCCTCG |
| CAGCGACCATTGAGA | GTGCTGGGATTGCAG | TTGTTCACGTGTTTA |
| CCGAGTGCCTGGGAT | CTCCACTATTATCCT | TGCGGAAGGCCGCAG |
| AAAAGAAAGAGAGAT | GACCGCGAGTGATCT | GGCGGTTTTGTCGAA |
| AGGCGGGAAAGGTGG | GGCCATGATGACGAT | TCAGATTGTTACTGT |
| CTGTTGCCGAGGCTG | CCCCGCCCGGCCAGC | TGCCCGGCCAGCCGC |
| TGGGAGGAGGTGGGG | CGGTCTCCAGCCCCT | ACTGGTTTTGGTGGA |
| GTCTCCCTCTCATGC | CGTCCGGGAGGAGGT | TGCCTTGGCCTCCCA |
| CCTAATCTCAAGTAC | TACAACCTACACCTC | GAATGATCAATAAAA |
| CCAGTCTGGGAAGTG | GGGAGACTTCATTTT | CAGAGACCTTTGTTC |
| CCTAATCTCAAGTAA | CCGGGAGGTGGGGGG | GAAAGAGAGATCAGA |
| TCCGGGAGGAGGTGG | GGTTTTGTGGAATAG | GAATGATCAATAAAT |
| CGGGTCTGTGTGGAT | GTTTTTTTTTGGTGG | AATTATCAATAAAAA |
| CAACCTCCACCTCCC | CGGGCTGGTCTCCAG | CCGGGATTGCAGACG |
| GGCTTTGTGGAATAG | TCCACTATTGTCCTA | GGTTGCCGTGTCTGT |
| CTGGGATGTGGGGAG | ATTGAGAACGGGCCA | AGACGGAGTCTCGTT |
| CTGGTCTCCAGCTCC | CTTCTCTCCACTATT | TGCTTGAAGGCAGCA |
| TGGGAAGTGAGGAGC | GTGATCCGCCAGCCT | ATAGAAAAGGGGGAA |
| CCCTCTGTTGCCGAG | GCTGGACGGTACTGC | AAAGAGGTAGACATG |
| GTGACCTTACCCCCA | CCCGTCCGGGAGGAG | GTTCACTTGTTTATC |
| CCCAAAGTGCCGAGA | TCTGGGATGTGGGGA | GTGTGCCCAGCGGCT |
| GGATTGCAGCCTCTG | AGAGACCTTTGTTCA | TCGCCGTGTTGGCCG |
| GTGGGGAAAAGATTG | CCCTCTGCCCGGCCG | TCCTGCCTCGGCCTG |
| GTGCAGTGGCGTGAT | GACCTTTGTTCACTT | CGTTCACTCAGTGCT |
| TAAGAAAAATTCTTC | CCCTCTGCCCGGCCA | GGGTCAGCCCCCCGC |
| TCTGGGAAGTGAGGA | TGCCCCGCCGCCCCG | TTGTATTTTTGGTG |
| AGTGCTCAATGGTGC | CCGGCCGCCCCGTCT | TGCCGAGTGCCTGGG |
| GTGCTTTGTTAAACA | GATTGTTACTGTGTC | TTGGGGATGGGCCAT |
| ATCCCATCTAGGAAG | TGGGATGTGGGGAGC | AAAAAATTAAAAAAA |
| CTGCCCCGCCGCCCC | ACCTCACCTCCCAG | TTTTGTGGAATAGAA |
| GCCTCGGCCTGCCGA | TGGTTTTCGTTTTTT | GGGGGTCAGCCCCC |
| CCTGCCAAATCCCCC | CCGGCCACCGCCCCG | CCTGCCTCGGCCTGC |
| CTCCCTAATCTCAAG | AATGATCAATAAAAA | ATGCCGAGCCAAAGC |
| CCCAAAGTGCTAAGA | ACCCCGTGCTCTCTG | CCTGACCGCGAGTGA |
| GCCCCGCCGCCCCGT | GAGTCTCGTTCACTC | CTATAACCTTACCCC |
| ATGGGAGACTTCATT | CACGTGTTTATCTGC | AATCCCCTCTCCGA |
| GTGCCCAGGCTGGAG | CAGGCACGCGCCGCC | CCTCCCGAGGTGCCG |
| GCCCCGTCTGGGAAG | TAGACATGGGAGACT | CAAAGCTGGACGGTA |
| AGCGCCTCCGCCCGG | TTAATCTATAACCTT | GGGAGCACCTCTGCC |
| ATCCGCCAGCCTCGG | TCTCCACTATTATCC | CCACGCCTGACTGGT |
| CATGGGAGACTTTTC | GTGTACCCAACAGCT | TGGACTGTACTGCCG |
| GGGTTTCGCCGTGTT | CCAGCTCCTGGCCTC | TACAACCACCTCCCA |
| CCTACTGGGAAGTGA | CCGTCCGGGAGGTGG | GTTTTGTCGAAAAGA |
| ATGTGGGGAAAAGAA | CCGTCCGGGAGGTGA | TCTGTGTAGAAAGAG |
| ATGGGCCATGATGAC | CCATCTCGGCTCACT | ATAGAGAAATCGGAT |
| GCCGCCACCCCGTCT | CCCCCCGCCCGGCCA | TCTGTGTAGAAAGAA |
| GGCACGCGCCGCCAC | TTGTCCTATGACCCT | GAGCGCCTCTGCCCG |
| TGTGAGGAGCGCCTC | CGGTCTCCCTCTGAT | ACCTTTGTTCACTTG |
| ACCGCGAGTGATCCG | ATTCTCCTGCCTCGG | GAGCGCCTCTGCCCC |
| GCTGCAACCTCCCTG | GATCTGTGACCTTAC | ATCTCGGCTCGCTAC |
| CCCAAGAATTATCAA | TGCCCGGCCACCGCC | AAAGGCGGGAAGGGT |
| GCCAAATCCCCTCT | ACTAAGAAAAATTCT | GATGTGGGGAGCACC |
| TTCGCTGTGTTGGCC | AAGTGCTAAGATTGC | GGGGTCAGCCCCCCG |
| CTGTGACCTTATCCC | GAGCGTCTCTGCCCG | TATGACCCTGCCACA |

TABLE 1-continued

Library of Antisense Oligonucleotides Targeting SVA

| | | |
|---|---|---|
| GCAACCTCCCTGCCT | GATCTGTGACCTTAT | GCCTCCCAAAGAGCC |
| CGAGGTGCTGGGATT | TGGTTCACTCAGTGC | AGCCTCTGCCCGGCC |
| CGCGAGTGATCCGCC | GACCCTGCCAAATCC | CCAGGGACACAAACA |
| GAAAAGAAAAGGGGG | GATTGCAGCCTCTGC | CCCGGCCGCCATCCC |
| ATTGTTGCTGTGTCT | GACCTCTGCCTAGGA | GAGGAGCGCCTCTGC |
| ACCGCCCCGTCTGGG | CATGATGACGATGGC | TCTCCCTGTCCCCTC |
| TGATCCGCCAGCCTC | GGGATTGCAGACGGA | CCCGTCTGGGATGTG |
| TGATTCTCCTGCCTC | CGGGAGGAGGTGGGG | TCAGCCCCCGCCCG |
| CAGCTCCTGACCGCG | ACCCCGTCTGGGAGG | GGGGAAATGTGGGGA |
| GTGCTCAATGTTGCC | CTCCCTCTCCCTCTC | CCCCTCTGCCCGGCC |
| GAGGAGGTGGGGGGG | CTCTCCACGGTCTCC | ATCTGCTGACCTTCC |
| GCTCCTGACCGCGAG | GGAGTCTCGCTCACT | GGGGAAAGGTGGGGA |
| TGCTCAATGTTGCCC | GGCCTCGAGTGATCT | TGCTCAATGGTGCCC |
| GTGCCCAGCGGCTCA | CCTCTGCCTGGCTGC | TACCCCCAACCCTGT |
| CCTCCCTGCCTGATT | TGCCCGGCCGCCCCT | ATCTGCTGACCTTCT |
| GCCGAGTGCCTGCGA | ATGCCGAGCCGAAGC | TTTGTCGAAAAGAAA |
| TCTGTGACCTTACCC | AAATCCCCTCTGTG | TTCTACGGTCTCCCT |
| ACCTCCCAGCCGCCT | CCTTTGTTCACTTGT | AGATGCTTGAAGGCA |
| AAAATTCTTCTGCCT | TTGTTTATCTGCTGA | CTGGCTGCCCAGTCT |
| AGTCTGGTTCACTCA | ACTGTACTGCCGCCA | CCTCCCAAAGTGCCG |
| TTTGTATTTTTGGT | AAAAAAAAAAAAAA | CTCTGAAACATGTGC |
| ATTGTCCTATGACCC | GCCGCCATCCCATCT | CCAAAGTGCTAAGAT |
| AATCTCAAGTACCCA | TGCCCGGCCGCCCCG | CGGGAGGTGGGGGC |
| TTGCTGTGTCTGTGT | GACCTTTGTTCACGT | ACGGGGTTTCGCCGT |
| CCGCCTGCCTTGGCC | GCCACATCCCCCTCT | GCTCACTGCAACCTC |
| CCGAGGTGCCGGGAT | GTTTTCGTTTTTTTT | GATGCCGAGCCAAAG |
| AAGAGAGATCAGATT | GTCTCTGCCCGGCCG | GTTGCCGTGTCTGTG |
| GCCCGGCCACCACCC | TGGTCTCCAGCTCCT | CCTAGGAAAACCAGA |
| GGGTGGGGAAAAAAT | CAGACGGAGTCTGGT | TGGCGGTTTTGTCGA |
| TCCACGGTCTCCCTC | CCAAAGAGCCGGATT | TCTCCCTCTCTCCA |
| GTCTCCAGCCCCTAA | TGGCTGCCCAGTCTG | CGCGAGTGATCTGCC |
| GCCTGGGATTGCAGG | GAGATCAGATTGTTA | TGTGCTGTGTCAACT |
| CGGGAGGTGAGGGGC | GGGAAATGTGGGGAA | TGTTCACATGTTTAT |
| CCTCCCAAAGAGCCG | CCTCCCAAAGTGCTA | TCTCCCTCTCATGCG |
| TGGACGGTACTGCTG | CCATCGTCTGAGATG | GAGGAGCGCCTCCGC |
| CCCCCTCTGTGAGAA | GGCGCCCATCGTCT | GGGAGGTGGGGGGT |
| GAGGTGCTGGGATTG | GGAGTGCAGTGGCGT | GTGTGGATAGAAGTA |
| GAGTCATCACCACTC | CCCTAACCGCGAGTG | AATAGAAAGGGGGA |
| AAACCAGAGACCTTT | GGTTTTGTCGAAAAG | AAGGCAGCATGCTCG |
| CGGGATTGCAGACGG | TAATCTATAACCTTA | ACCCTGCCACATCCC |
| CCGAAGCTGGACTGT | TACACCTCCCAGCCG | AAGAATTATCAATAA |
| TGACTGGTTTTTGTA | TTGCAGCCTCTGCCC | CCACCTCCCAGCCGC |
| TTTTTTGGTGGAGAC | AGATTGAGAAATCGG | TTGTTCACATGTTTA |
| GGATGGTTGCCGGGT | ATTGTTACTGTGTCT | AGCCCCTCTGCCCGG |
| CGGCCGCCATCCCGT | TTTGTTCACTTGTTT | ACTCCATTTTGTTCT |
| GGAAGTGAGGAGCGC | CTCGCTACAACCTAC | GTTCACTCAGTGCTC |
| CGAGTGCCTGGGATT | ACTGGTTTTCGTTTT | GTCCCTCTTTCCAC |
| TGGCCGCCCATCGTC | CTGCCCGGCCACCAC | AAGGGGGAAATGTGG |
| GAGATGTGGGGAGCG | GCTCCAGTGATTCTC | CCGGGCTGGTCTCCA |
| CCTCTTCCCGGCCGC | CTAAGAAAAATTCTT | CGCCGCCACGCCTGA |
| GCGTGATCTCGGCTC | CCCCCTCTCCGAGAA | CGTCTGGGAGGTGAG |
| GTGCTCAATGGTGCC | CCTCTCTCCACGGTC | TGGTTTTTGTATTTT |
| TGGAATAGAAAGGCG | AATAGAAAGGGGGA | AGTGCAGTGGCGTGA |
| AAAGTGCTAAGATTG | TCTTTCCACGGTCTC | GAGAAACACCCAAGA |
| TTCCCTCCACTATTG | CGTGTCTGTGTAGAA | ACTGGTTTTCGTATT |
| CCTTGGGATCCTGTT | TCCAGCTCCTAACCG | AAGATAGAGAAATCG |
| CGGGGTTTCGCCGTG | TCCTAACCGCGAGTG | CCTGCGATTGCAGGC |
| CCAAGAATTATCAAT | TGACCTTCCCTCCAC | AAGTGCCGAGATTGC |
| CCCAACAGCTCATTG | CAGGGACCTCTGCCT | TGCTGACCTTCCCTC |
| TTTATCTGCTGACCT | TGTTAAACAGATGCT | ATTTTGTTCTGTACT |
| TGCTGTTAATCTATA | CCGTCTGGGAGGTGA | ATGATCAATAAATAC |
| GTGGGAAAAAATTG | AATGATCAATAAATA | CTGCCGCCATCTCGG |
| AGGGGCGCCTCTGCC | CGCCAGCCTCGGCCT | GTCTGGGAGGTGTAC |
| ATAAAAAAATTAAA | TGGTGCCCAGGCTGG | AGGTGTACCCAGCGA |
| CGGGCCAGGATGACA | TGCCTGGCCGCCCAT | TTTTGGTGGAGACGG |
| GAGCCCCTCTGCCCG | AGGAAAACCAGAGAC | TTTTTGTATTTTTGG |
| TCTCCTGCCTCAGCC | CTCGGCTCGCTGCAA | AATCGGATTGTTGCT |
| GCCGCAGGGACCTCT | GAGGTGTGCCCAACA | TTGCCGTGTCTGTGT |
| GTAGACATGGGAGAC | ACGCGCCGCCACGCC | TCTGCCCCGCCGCCC |
| CTCCAGCTCCTGACC | CCGTCTGGGAGGTGT | TCCCAAAGAGCCGGA |
| TGGGATCCTGTTGAT | CTCCTGGCCTCGAGT | CCTACACCTCCCAGC |
| GGATGGTTGCCGTGT | GAGTCTGGTTCACTC | ACGATGGCGGTTTTG |
| CTGGTTTTTGTATTT | CGTCTCTGCCCGCC | CCCGCCTCGGCCTCC |
| AGTGAGGAGCGTCTC | TTCTCCTGCCTCAGC | GGATGTGAGGAGCGC |
| GTCTGGGAGGTGGGG | CCCTGTGCTCTCTGA | CCGGGCCGGTCTCCA |
| AACCCCGTGCTCTCT | CCTCCCGAGGTGCTG | GGCTGCCCAGTCTGG |
| CGTCTGGGAAGTGAG | GTCCCATGACCCTGC | CTGTGTCCACTCAGG |

TABLE 1-continued

| Library of Antisense Oligonucleotides Targeting SVA | | |
|---|---|---|
| TGCCTCAGCCTGCCG | AGAAAGAGAGATCAG | AGTCATCACCACTCC |
| CTTATCCCCAACCCT | CGAGCCGAGGCTGGA | CTGGTTTTGGTGGAG |
| AGGAGCGTCTCTGCC | ATAGAAAGGCGGGAA | GGTGTGCCCAGCGGC |
| TATTGTCCTATGACC | AGCCGCCCCGTCCGG | CGAGCCGAAGCTGGA |
| TCCCCAACCCTGTGC | CGGATTGCAGCCTCT | GGGCTCCAGTGATTC |
| GACTCCATTTTGTTC | TTATCCCCAACCCTG | TCCACTATTATCCTA |
| CACTATTGTCCTATG | AATCTATAACCTTAC | GAAGCTGGACTGTAC |
| GAAGTGAGGAGCGCC | CTACAACCTCCACCT | GGCCGCCCAGTCTGG |
| CGCAGGGACCTCTGC | GTGGGGAGCACCTCT | TGGAGACGGGGTTTC |
| CTTGAAGGCAGCATG | AAATCCCCCTCTGCG | TCACTTGTTTATCTG |
| TTGGTGGAGACGGGG | TGCAGGCGCGCGCCG | CCCTGCCACATCCCC |
| CCCAAAGAGCCGGAT | GATCTCGGCTCGCTG | TCTCCTGCCTCGGCC |
| GCCTGATTCTCCTGC | CAGCCTGCCGAGTGC | TAGGAGACTCCATTT |
| TTTTCATTTTGTTCT | AGATTGCAGCCTCTG | GACGGAGTCTGGTTC |
| GTTACTGTGTCTGTG | TGCCCAGCGGCTCAT | TTGGCCGGGCTGGTC |
| TGACCGCGAGTGATC | AGGTGAGGGGCGCCT | GAAAACCAGAGACCT |
| CTCGTTCACTCAGTG | GATCTCGGCTCGCTA | GATGTGAGGAGCCCC |
| CCGCCATCCCGTCTG | TGCCCGCCTCGGCCT | TAGAAGTAGACATGG |
| TCTCCAGCCCCTAAC | GGGCGGTGCAAGATG | CCCTCTCCCTGTCCC |
| CTCTCCGAGAAACAC | CCCGTCTAGGAAGTG | TGGGATGCTGTTAAT |
| GGATAGAAGTAGACA | AGACATAGGAGACTC | CCCGAGGTGCCGGGA |
| CGGATTGTTGCTGTG | TAATCTTAAGTACCC | CATCCCGTCTGGGAA |
| TGTGCTGTGTCCACT | ACCTCCCTGCCTGAT | TCAATGGTGCCCAGG |
| AGGTGGGGAAAAGAT | TCCGCCAGCCTCGGC | CCGGCCGCCCCTTCT |
| CATGTGCTGTGTCAA | TCCCGTCTGGGAAGT | GACAATGGCGGTTTT |
| TCCACTCAGGGTTAA | GAGGTGCCGGGATTG | ACCATTGAGAACGGG |
| GTGGCGTGATCTCGG | CCTCTGCGAGAAACA | AAAAGAAAAGGGGGA |
| CCCAGCCGCCTGCCT | TGGTTTTCGTATTTT | CAACAGCTCATTGAG |
| TGACCGGGCTGGTCT | CCCCTAACCGCGAGT | GAGAACGGGCCAGGA |
| GAGCCCCTCTGCCTG | AGATGTGCTTTGTTA | CTGACCGCGAGTGAT |
| GGGCCGGTCTCCAGC | AAAAAATTGAGAAAT | ATCAGGGACACAAAC |
| GGCTGGTCTCCAGCT | ATGCGGAGCCGAAGC | CGCCCCTACTGGGAA |
| CCCTACTGGGAAGTG | GCTGTGTTGACCGGG | TGCAGACGGAGTCTC |
| GAGGTGTACCCAACA | TTTCGCTGTGTTGAC | AGGGCGGTGCAAGAT |
| GGATGTGGGGAGCGC | GCTGGGATTGCAGAC | TGTTCACGTGTTTAT |
| CCTTTGTTCACATGT | GATGCCGAGCCGAGG | TGCAGACGGAGTCTG |
| ATGTTGCCCAGGCTG | CGTGATCTCGGCTCG | GAAAAGGGGGAAATG |
| CTTTGTTCACATGTT | TGTGACCTTATCCCC | GCCGCCCATCGTCTG |

TABLE 1-continued

| Library of Antisense Oligonucleotides Targeting SVA | | |
|---|---|---|
| AAAGCTGGACGGTAC | AATGTTGCCCAGGCT | ATGTGCTTTGTTAAA |
| GATGGGCCATGATGA | CTTTCCACGGTCTCC | CTGTGTAGAAAGAAG |
| CTAACCGCGAGTGAT | AGTGCCTGCGATTGC | CGTGTTGGCCGGGCT |
| GCTTTGTTAAACAGA | CCGGTCTCCAGCCCC | GTGTGCCCAACAGCT |
| CCGGCCGCCATCCCA | AGAACGGGCCAGGAT | CAGCCGCCCCGTCCG |
| CCCCAACCCTGTGCT | AGGCTGGAGTGCAGT | TGCCGAGGCTGGACT |
| GTCTCCAGCTCCTGA | GCCGAGCCGAAGCTG | CTAGGAAGTGAGGAG |
| AGCCAAAGCTGGACG | GTGTAGAAAGAAGTA | AAACAGATGCTTGAA |
| GTCTCCAGCTCCTGG | TTTCATTTTGTTCTG | AGTACCCAGGGACAC |
| TGCGATTGCAGGCGC | AGAGCCGGATTGCAG | TCTCCCTCTCCCTGT |
| GAAAAGATAGAGAAA | GGGATGGGCCATGAT | TGTTGGCCGGGCCGG |
| GGTTGCCGGGTCTGT | GCGGCTTTGTGGAAT | GCAGTGGCGTGATCT |
| GCTGGTCTCCAGCTC | TGAGGAGCCCCTCTG | AGCCGGATTGCAGCC |
| GCAGCCTCTGCCCGG | AAATCGGATTGTTGC | GGCCGCAGGGACCTC |
| TTGCAGGCGCGCGCC | TTATCAATAAAAAAA | AAAGAAAAGGGGGAA |
| CCACATCCCCCTCTC | ACACCCAAGAATTAT | ACGGGCCAGGATGAC |
| GGGATGTGAGGAGCG | CACCTCCCAGCCGCC | AGCCTGCCGAGTGCC |
| CTCCGCCCGGCCGCC | GGCCTCCCAAAGTGC | AACACTGCGGAAGGC |
| GGGATGTGAGGAGCC | TGTGCCCAACAGCTC | TGTTTATCTGCTGAC |
| AGACTCCATTTTGTT | GCCCGGCCGCCCCGT | TGTGTAGAAAGAGGT |
| ATCGGATTGTTGCTG | CTCAAGTACCCAGGG | TGCAGTGGCGTGATC |
| GAGGTGGGGGGGTCA | CAGGGTCCTCTGCCT | CGCAGGGTCCTCTGC |
| CCTCTGCCCCGCCGC | CATCCCATCTAGGAA | CACTGCAACCTCCCT |
| CCTCTGTGAGAAACA | TTGGCCTCCCAAAGT | TGTGCTTTGTTAAAC |
| GACCTTTGTTCACAT | TGATGACGATGGCGG | TATGACCCTGCCAAA |
| CTGCCATCTCGGCTC | GGTGCCGGGATTGCA | CTCTGCCCGGCCAGC |
| TGCTGACCTTCTCTC | ATGCTGTTGATCTGT | CCACTATTGTCCCAT |
| CTCTCCCTGTCCCCT | CAATGGTGCCCAGGC | CCACTATTATCCTAT |
| GCCGCCCAGTCTGGG | GGGATTGCAGGCGCG | ATGACAATGGCGGCT |
| CTGCGGAAGGCCGCA | TCCAGCCCCTAACCG | CTGTACTAAGAAAAA |
| CCCGGCCGCCCATCG | TTGGCCTCCCAAAGA | TGTGAGGAGCCCCTC |
| AAAAATTCTTCTGCC | CGGTGCAAGATGTGC | TTCGCCGTGTTGGCC |
| GCCGAGTGCCTGGGA | GCTGTGTCAACTCAG | ATAGAAGTAGACATG |
| CTGCTGACCTTCCCT | CCGCCCGGCCGCCAT | TAATCTCAAGTAATC |
| ACGCCTGACTGGTTT | CCTCTTTCCACGGTC | AAAGAGAGATCAGAT |
| ACCCAACAGCTCATT | GTTTTGTGGAATAGA | TCATCACCACTCCCT |
| GGATTGTTGCTGTGT | AAATCGGATGGTTGC | TGCTGTTGATCTGTG |
| CCCTGCCTGATTCTC | GCTCGCTGCAACCTC | CATCCCCCTCTCCGA |
| TGCCGTGTCTGTGTA | GCTCGTTAAGAGTCA | GAGGAGCCCCTCTGC |

TABLE 1-continued

Library of Antisense Oligonucleotides Targeting SVA

| | | |
|---|---|---|
| GGAAAGGTGGGAAA | ACCCAAGAATTATCA | CTGTACTGCCGCCAT |
| GTGGGGAAAAGAAAG | AGGCTGGACTGTACT | GGTGGAGACGGGGTT |
| TGGGAGACTTCATTT | GGCCACCGCCCCGTC | GTTTTCGTATTTTTT |
| TCTGGGAGGTGTGCC | CGGATGGTTGCCGTG | ACCTCTGCCCCGCCG |
| GGACACAAACACTGC | TACCCAGGGACACAA | ACTGTACTGCTGCCA |
| TGCCTGGCCGCCCAG | GACCTTCCCTCCACT | TGTACCCAACAGCTC |
| ACGGAGTCTCGCTCA | AACCCTGTGCTCTCT | GATGGTTGCCGTGTC |
| GTCTCGCTCACTCAG | CTGCCACATCCCCCT | CAGTGGCGTGATCTC |
| TCAAGTAATCAGGGA | GTTGCCCAGGCTGGA | GTGTCCACTCAGGGT |
| GCGGTTTTGTCGAAT | GTTCTGTACTAAGAA | TAGAAAGAGGTAGAC |
| GCCAAAGCTGGACGG | TTGTCGAAAAGAAAA | CTCGGGCTCCAGTGA |
| CACTCCCTAATCTTA | TCCCCCTCTGCGAGA | GCCCAGCGGCTCATT |
| ACCACTCCCTAATCT | CCTGCCTCAGCCTGC | CAGTGATTCTCCTGC |
| GCGGTTTTGTCGAAA | TTACTGTGTCTGTGT | GCCTCTGCCCGGCCA |
| TTGTGGAATAGAAAG | TGGGAGGTGAGGGGC | TGTGTCAACTCAGGG |
| CCCGTGCTCTCTGAA | CTTCTGCCTTGGGAT | TGTGTCTGTGTAGAA |
| TAGGAAGTGAGGAGC | GACCTTACCCCCAAC | TTGTCCCATGACCCT |
| AAAAATTGAGAAATC | TTCTCCTGCCTCGGC | AAACACCCAAGAATT |
| GCGGAGCCGAAGCTG | CCGCAGGGTCCTCTG | AAGGGGGGAAAGGTG |
| CTCTCATGCGGAGCC | AGGTGCCGGGATTGC | TTTTGTATTTTTGGT |
| GGTGAGGGGCGCCTC | CCCGGCCACCACCCC | TTATCTGCTGACCTT |
| AGGCCGCAGGGTCCT | CATGGGAGACTTCAT | AAGAGCCGGATTGCA |
| GCCACGCCTGACTGG | TGCCTGGCTGCCCAG | AAGTGAGGAGCCCCT |
| CGGCCGCCATCCCAT | TATTATCCTATGACC | CCTGGCCTCGAGTGA |
| TCTCCAGCTCCTGGC | CCTGCCTCGGGCTCC | ACTGCAACCTCCCTG |
| TCCGAGAAACACCCA | GGGGGAAAGGTGGGG | GCCCGGCCACCGCCC |
| CACTCAGGGTTAAAT | CTCCCTGCCTCGGGC | AACTCAGGGTTAAAT |
| CGGCCACCGCCCCGT | CAGCCCCTAACCGCG | CTGGCCGCCCATCGT |
| GTAGACATAGGAGAC | ACCTACACCTCCCAG | CAGGCTGGAGTGCAG |
| AGTGCTAAGATTGCA | AAGGTGGGAAAAGA | TGCCACATCCCCCTC |
| TTCTGCCTTGGGATG | TCCCCTCTCTCCACG | GGCCGGGCCGGTCTC |
| TCCCCTCTTTCCACG | GATGTGGGAGCGCC | CTGACTGGTTTTGT |
| GGGGAAAAGAAAGAG | GACCCTGCCACATCC | AGGGTTAAATGGATT |
| AGATTGTTACTGTGT | AGCGGCTCATTGGGG | TGCCGAGTGCCTGCG |
| TCGCTACAACCTACA | ATCAATAAAAAAAAT | AGTCTGGGAAGTGAG |
| CTCCCAAAGTGCTAA | GCCTTGGCCTCCCAA | TTGTTACTGTGTCTG |
| CCCAGCGACCATTGA | TTAAGGGCGGTGCAA | CGCTGTGTTGACCGG |
| CCTCGGCCTGCCGAG | ATGGCGGCTTTGTGG | ACGTGTTTATCTGCT |

TABLE 1-continued

Library of Antisense Oligonucleotides Targeting SVA

| | | |
|---|---|---|
| CGAGATTGCAGCCTC | AAGGGCGGTGCAAGA | AACATGTCTGTGTC |
| AATACTAAAAAAAAA | GTGCCGAGATTGCAG | GCCATGATGACGATG |
| GCTCCTGGCCTCGAG | GCCTGCCTTGGCCTC | AACGGGCCATGATGA |
| TCGTCTGAGATGTGG | GCCGCCCCGTCCGGG | TGTGCTCTCTGAAAC |
| ATCAATAAATACTAA | CCAAATCCCCCTCTC | AGGAGCGCCTCTTCC |
| GAAGTGAGGAGCGTC | ACCTTTGTTCACATG | CTCTGCCTGGCCGCC |
| GGATTGCAGGCACGC | CCAAATCCCCCTCTG | TCGGATGGTTGCCGG |
| AAATTCTTCTGCCTT | TATCCTATGACCCTG | GGCCGCCACCCCGTC |
| CGCTACAACCACCTC | CTGTGTTGACCGGGC | CTCCTGCCTCAGCCT |
| GGCGGGAAAGGTGGG | GTTTTGTCGAATAGA | GCTCAATGGTGCCCA |
| TCTCTGCCCGGCCGC | GGTCTCCCTCTCATG | AATGTGGGGAAAAGA |
| ATGGCGGTTTTGTCG | GCTAAGATTGCAGCC | CGGATGGTTGCCGGG |
| CAAGAATGATCAATA | TTAAATGGATTAAGG | TTCTGTACTAAGAAA |
| CTGTGACCTTACCCC | TCTGGTTCACTCAGT | AAAGGGGGGAAAGGT |
| TGCAGCCTCTGCCCG | TGCCCGGCCGCCATC | TCTGTACTAAGAAAA |
| AACCTTACCCCCAAC | CGCCCGGCCAGCCGC | CGCCTCTTCCCGGCC |
| TGGAATAGAAAGGGG | CCCTTCTGGGAAGTG | CCACCGCCCCGTCTG |
| AAGTAATCAGGGACA | TCCAGCTCCTGACCG | TGATCTGCCCGCCTC |
| AACCACCTCCCAGCC | TGGGGAGCGCCTCTG | AGTAGACATGGGAGA |
| GTGTCAACTCAGGGT | TCGAGTGATCTGCCC | CATGTGCTGTGTCCA |
| GTGACCTTATCCCCA | GTCCGGGAGGTGAGG | CAACCACCTCCCAGC |
| GGGTTTCGCTGTGTT | GCGATTGCAGGCGCG | CTCTCCCTCTCCCTG |
| CTCCGAGAAACACCC | TTAAACAGATGCTTG | CCGAGCCGAGGCTGG |
| GCCTTGGGATGCTGT | TGTTGCCCAGGCTGG | ACAACCTCCACCTCC |
| GACAATGGCGGCTTT | TCCCGTCTAGGAAGT | CAGGGACACAAACAC |
| TAACCGCGAGTGATC | GGTCTCCCTCTGATG | TCCTGTTGATCTGTG |
| AGACGGGGTTTCGCC | CTGGGATTGCAGGCA | CCCCTCTGCCTGGCC |
| GACTGTACTGCTGCC | CCAAAGCTGGACGGT | GGGAAAAGATAGAGA |
| GGTTTTGTCGAATAG | TGACTGGTTTTCGTT | TCACCACTCCCTAAT |
| TCCTCTGCCTAGGAA | AATCCCCCTCTGTGA | CTGACTGGTTTTCGT |
| GTCTGGGAGGAGGTG | TTTTTTTTGGTGGAG | CCGCCCCTACTGGGA |
| GTCTGGGAGGTGTGC | TGTTAATCTATAACC | CCTATGACCCTGCCA |
| CTCCCTCTGATGCCG | ACCCAGGGACACAAA | AGCCGAGGCTGGACT |
| AGACGGGGTTTCGCT | CGGCCTGCCGAGTGC | CCCCCAACCCCGTGC |
| ACATGTTTATCTGCT | TATTTTTGGTGGAG | CGTCTGGGATGTGAG |
| GAATAGAAAGGGGG | GCCCCTACTGGGAAG | CCTGCCGAGTGCCTG |
| TGGGATGCTGTTGAT | CGTCTGAGATGTGGG | ATCACCACTCCCTAA |
| TGGCCGGGCTGGTCT | TGACTGGTTTTCGTA | AGGCGCGCGCCGCCA |
| TCAATAAAAAAAATT | GTGCCTGGGATTGCA | AGCGCCTCTGCCCCG |

TABLE 1-continued

Library of Antisense Oligonucleotides Targeting SVA

| | | |
|---|---|---|
| GAAATGTGGGGAAAA | TACCCAACAGCTCAT | TTTGTCGAATAGAAA |
| GCTACAACCTCCACC | CGAAAAGAAAAGGGG | GGTGTACCCAACAGC |
| CGCCTGACTGGTTTT | GGCTGGACTGTACTG | TTCACTCAGTGCTCA |
| CTGGGAAGTGAGGAG | CCAACAGCTCATTGA | GACTGGTTTTGGTGG |
| GATCCGCCAGCCTCG | GGGATCCTGTTGATC | GGGACACAAACACTG |
| GTACCCAGCGACCAT | AAAGGGGAAATGTG | TCGAATAGAAAAGGG |
| TCTTCCCGGCCGCCA | CTGTACTGCCGTGAT | GAAATCGGATGGTTG |
| GCGCGCGCCGCCACG | AGGTGTACCCAACAG | GGCCAGCCGCCCCGT |
| CGGCTTTGTGGAATA | CCCGTCCGGGAGGTG | CTGGAGTGCAGTGGC |
| GTCTCCCTCTGTTGC | TCTCGGCTCGCTGCA | AGAAAAATTCTTCTG |
| CTCCCCTCTTTCCAC | AATCTTAAGTACCCA | CACTATTGTCCCATG |
| TCCCAGCCGCCTGCC | CCTCGGCCTCCCGAG | CCGGCCACCACCCCG |
| GCTCTCTGAAACATG | AGACCTTTGTTCACT | CCGCCATCCCATCTA |
| GGGAAAAGATTGAGA | ATGATCAATAAAAAA | TCTGTGAGAAACACC |
| CGCGCGCCGCCACGC | GCCATCCCGTCTAGG | CAATGTTGCCCAGGC |
| CCCTCTGATGCCGAG | ATTTTTTTGGTGGAG | GTCTGTGTAGAAAGA |
| TTGGGATGCTGTTAA | AGAAAAGGGGGAAAT | TGACAATGGCGGCTT |
| TGCCCAGTCTGGGAA | TTTTCGTTTTTTTTT | CCCTCTGCCTGGCCG |
| CACCCAAGAATGATC | ATGTGGGGAGCGCCT | TCCCTGTCCCTCTT |
| CTCCAGCTCCTAACC | TCTCAAGTAATCAGG | CGAGGCTGGACTGTA |
| GGCGGGAAGGGTGGG | GATCAATAAATACTA | TGACAATGGCGGTTT |
| CTGATTCTCCTGCCT | TCTGCTGACCTTCCC | AAAAAAATTAAAAAA |
| AGGCGGGAAGGGTGG | ACTGCCGTGATCTCG | TCTGGGATGTGAGGA |
| CCCCGCCCGGCCAG | AGCTCATTGAGAACG | GGGAAGGGTGGGAA |
| CCTGGCCGCCCAGTC | ATGTGAGGAGCGCCT | AAAAGATAGAGAAAT |
| GTCTGGGAAGTGAGG | TACTGTGTCTGTGTA | TGTACTAAGAAAAAT |
| GTGTACCCAGCGACC | GGGAGGTGTACCCAA | TGCTGTGTCCACTCA |
| GGAAAAGAAAGAGAG | GGGGGGAAAGGTGGG | AAGAGTCATCACCAC |
| CTGCCTGGCCGCCCA | GCCTCGAGTGATCTG | CTCTCCCTCTCTCC |
| TCTGCCCGGCCACCG | TCTTTCTACGGTCTC | ATGTTTATCTGCTGA |
| CGGAGTCTCGCTCAC | GCCCCGTCCGGGAGG | CAAACACTGCGGAAG |
| GCTGTTGATCTGTGA | TCGGCTCGCTACAAC | CATGTTTATCTGCTG |
| TCTGCCCGGCCACCA | GACCTTATCCCCAAC | TGCAGGCACGCGCCG |
| GGGGAGCACCTCTGC | CTGATGCCGAGCCGA | CCGAGAAACACCCAA |
| TGCCGAGCCGAGGCT | TGTGTTGGCCGGGCC | AGGTGTGCCCAGCGG |
| TCCCTCTCCCTCTCC | ACCGGGCTGGTCTCC | CCGTGTCTGTGTAGA |
| AGGCAGCATGCTCGT | CTACGGTCCCTCT | TGTCGAATAGAAAAG |
| GAGTGATCTGCCCGC | GCCATCTCGGCTCAC | CGGGGTTTCGCTGTG |
| GCCCGGCCAGCCGCC | CTACACCTCCCAGCC | GAGTGCCTGCGATTG |
| CGGTACTGCTGCCAT | TTTTTGTATTTTTTG | TACAACCTCCACCTC |
| TCAGCCTGCCGAGTG | TGTGTTGGCCGGGCT | CCTTCCCTCCACTAT |
| CCCTCTTTCTACGGT | CTCTGCCTAGGAAAA | TGGGGAAAAGATTGA |
| TGCCTTGGGATCCTG | GGACGGTACTGCTGC | TCCCTCTGTTGCCGA |
| GAGGGGCGCCTCTGC | CGGGAAGGGTGGGA | GCAGGCACGCGCCGC |
| TCCGCCCGGCCGCCA | CGCCCGGCCGCCATC | TAACCTTACCCCCAA |
| ACCTTCCCTCCACTA | TGCTGTGTCTGTGTA | CCGCCCGGCCAGCCG |
| CTGGGATTGCAGGCG | ATCAATAAAAAAAAA | CTCCCAAAGTGCCGA |
| GTTAATCTATAACCT | GGTCTCCAGCTCCTA | GCCCAACAGCTCATT |
| TGTGGGGAGCACCTC | GCTCATTGAGAACGG | GCCATCCCGTCTGGG |
| GCTGTGTTGGCCGGG | GGTCTCCAGCTCCTG | CCTTCTCTCCACTAT |
| CCCCTTCTGGGAAGT | TCTAGGAAGTGAGGA | CTGCCTCAGCCTGCC |
| CCAGCCCCTAACCGC | GTTAAATGGATTAAG | TCATTGGGGATGGGC |
| AGATGTGGGGAGCGC | GGGGAAAAGATTGAG | CCGCCCCGTCCGGGA |
| TCTCGTTCACTCAGT | CCCTCTCTCCACGGT | AAGGCGGGAAGGTG |
| CTGGACGGTACTGCT | GGAGCGCCTCCGCCC | CGTTTTTTTTTGGTG |
| GGGGGTCAGCCCCCC | AGCCGAAGCTGGACT | CCCCAACCCCGTGCT |
| GAAAGGCGGGAAGGG | CGCCCGTCTGGGAA | GTCTCGTTCACTCAG |
| ATAAAAAAAAAAAAA | AGCGCCTCTGCCCGG | TGGGGAGCACCTCTG |
| GGTTTTGGTGGAGAC | CCAGCCGCCCCGTCC | CTGACCTTCTCTCCA |
| TGCCGAGCCGAAGCT | TGATCAATAAAAAAA | GGCCGCCCCTTCTGG |
| AGAGATCAGATTGTT | CAACCCTGTGCTCTC | GACTGGTTTTCGTTT |
| GAAGTAGACATAGGA | AAGGCGGGAAGGGTG | ATGACGATGGCGGTT |
| GAAGGGTGGGGAAAA | GTACTGCTGCCATCT | AGTGCTCAATGTTGC |
| CAGCGGCTCATTGGG | TGTTGCCGAGGCTGG | TGGATTAAGGGCGGT |
| GGAAGGGTGGGGAAA | CCAGCCGCCCCGTCT | CTGCCTGGCTGCCCA |
| CCCCGTCTGGGAGGA | TGAAACATGTGCTGT | TTTGTGGAATAGAAA |
| CACATCCCCCTCTCC | GAGATTGCAGCCTCT | GTGGGGGGTCAGCC |
| GCCTCCCAAAGTGCT | CAAATCCCCCTCTCC | CTTGGGATGCTGTTG |
| GAGAAATCGGATGGT | GGCGCGCGCCGCCAC | CTTGGGATGCTGTTA |
| GCCCCCCGCCCGGCC | AAGTAGACATGGGAG | AGATCAGATTGTTAC |
| CGACCATTGAGAACG | TCCTATGACCCTGCC | GCCTGGCTGCCCAGT |
| TCCCAAAGTGCCGAG | ATGCTTGAAGGCAGC | TCGGGCTCCAGTGAT |
| CCCCGTCTGGGAGGT | TCCCCCTCTGTGAGA | CTTTGTGGAATAGAA |
| CACCCAAGAATTATC | ATTGCAGACGGAGTC | TAAATGGATTAAGGG |
| GCCTCCCAAAGTGCC | CCTTACCCCCAACCC | TCGGCTCACTGCAAC |
| TCCCTAATCTTAAGT | CTGGACTGTACTGCC | CTCATGCGGAGCCGA |
| CGGGAAAGGTGGGA | GGACCTCTGCCTAGG | GCTACAACCACCTCC |

TABLE 1-continued

Library of Antisense Oligonucleotides Targeting SVA

| | | |
|---|---|---|
| TTCTGCCTTGGGATC | CGCCCCGTCTGGGAG | CTGCCTCGGCCTGCC |
| AGCCCCCCGCCCGGC | CACTTGTTTATCTGC | CGGCCAGCCGCCCCG |
| CCAGGCTGGAGTGCA | CTGCAACCTCCCTGC | TTGATCTGTGACCTT |
| AGAAATCGGATGGTT | TGCGATTGCAGGCAC | AGAAATCGGATTGTT |
| AAAATTGAGAAATCG | CTCTGTTGCCGAGGC | AACACCCAAGAATTA |
| TCTGCCTTGGGATCC | AAGGCCGCAGGGACC | CGCCATCCCGTCTAG |
| GCCTGGCCGCCCATC | TGCCTCGGCCTGCCG | GATGCTTGAAGGCAG |
| GATTAAGGGCGGTGC | GCTCAATGTTGCCCA | GGCTCGCTGCAACCT |
| GCCGCCCCTTCTGGG | CCTCTCCCTCTCCCC | GATAGAGAAATCGGA |
| CAGCCCCCCGCCCGG | GGGAGGTGAGGGGCG | TCCGGGAGGTGGGGG |
| GCGCCGCCACGCCTG | GAGGTGGGGGGCGCC | GAGACGGGGTTTCGC |
| CTGCCCGGCCGCCCA | CAGCCGCCCCGTCTG | TGCCTTGGGATGCTG |
| CCCCTCTGCCTGGCT | ATGTGCTGTGTCCAC | GAGCGCCTCCGCCCG |
| CTGCCCGGCCGCCCC | CCTCTCCCTCTCCCT | CTGGGAGGTGAGGGG |
| CAGGCGCGCGCCGCC | TTCTTCTGCCTTGGG | TGTAGAAAGAGGTAG |
| GCTACAACCTACACC | GGAGACTTTTCATTT | ATCCCCCTCTGCGAG |
| GGTCAGCCCCCCGCC | GGTTTCGCCGTGTTG | GCCATGATGACAATG |
| TGATCTGTGACCTTA | GCCTCGGGCTCCAGT | AATCGGATGGTTGCC |
| TAAGTACCCAGGGAC | AGCTCCTGACCGCGA | TAAAAAAAATTAAAA |
| GTTGACCGGGCTGGT | CTGCGATTGCAGGCA | CCTCTGATGCCGAGC |
| TGGCCGCCCAGTCTG | CTGCGATTGCAGGCG | TTTGTTCACGTGTTT |
| GCGGAAGGCCGCAGG | GCCTGCCGAGTGCCT | GCGCCTCCGCCCGGC |
| TACTGGGAAGTGAGG | TTCCCGGCCGCCATC | CCCGGCCAGCCGCCC |
| TTCGTATTTTTTTGG | CTGGACTGTACTGCT | TCCCCCTCTCCGAGA |
| GGGAAAGGTGGGGAA | CAGATTGTTACTGTG | AAGTAGACATAGGAG |
| CGAGTGCCTGCGATT | TAAATACTAAAAAAA | GACGGAGTCTCGTTC |
| ACCTCTGCCTAGGAA | AGGAGCGCCTCCGCC | TGCCGGGATTGCAGA |
| CGCCACGCCTGACTG | CGCCCCGTCTGGGAT | GGTGCTGGGATTGCA |
| CCTTGGCCTCCCAAA | GGAAATGTGGGGAAA | CTCAGTGCTCAATGT |
| TCAATAAATACTAAA | CTCCACCTCCCAGCC | GTCGAAAAGAAAAGG |
| AAAATTAAAAAAAAA | GTACTGCCGCCATCT | TGGGGAAAAGAAAGA |
| CTCAGTGCTCAATGG | TCTTCTGCCTTGGGA | TGGGGAAAAAATTGA |
| CGTCTCTGCCTGGCC | GTGAGGAGCCCCTCT | TTTTTGGTGGAGACG |
| ACTGCCGCCATCTCG | GAGCACCTCTGCCCC | AATAAAAAAAAAAAA |
| TTGTTGCTGTGTCTG | TTATCCTATGACCCT | AGCATGCTCGTTAAG |
| TCGGATTGTTGCTGT | CTTAAGTACCCAGGG | CGGCCGCCCCTACTG |
| CCTGTTGATCTGTGA | GATGTGAGGAGCGCC | AGAATTATCAATAAA |
| CTTCCCGGCCGCCAT | CCCAGTCTGGGAAGT | TAAACAGATGCTTGA |
| ATAGGAGACTCCATT | GATCAGATTGTTACT | CTGGGATGTGAGGAG |
| GCCACCCCGTCTGGG | CCGCCAGCCTCGGCC | CTTGGCCTCCCAAAG |
| TGTGGAATAGAAAGG | TGTCCCCTCTTTCCA | GACGATGGCGGTTTT |
| CCGCAGGGACCTCTG | ACTTGTTTATCTGCT | TTGTCGAATAGAAAA |
| CGCCTCCGCCCGGCC | CTCTCTGAAACATGT | GCCCGGCCGCCCATC |
| CCCTAATCTCAAGTA | GACGGTACTGCTGCC | CGGAAGGCCGCAGGG |
| AGACATGGGAGACTT | GCACGCGCCGCCACG | CCATGACCCTGCCAA |
| ATCTCAAGTACCCAG | GGAGCGCCTCTTCCC | ACTATTGTCCTATGA |
| ACACTGCGGAAGGCC | CATTTTGTTCTGTAC | CTCTGCCTGGCTGCC |
| TTGCCGGGTCTGTGT | GGAGGTGTGCCCAGC | GTGCAAGATGTGCTT |
| TCGCTGTGTTGACCG | AACCGCGAGTGATCC | GATTGTTGCTGTGTC |
| CCCAGGGACACAAAC | GTACTGCCGTGATCT | CCTCTGCCCGGCCAC |
| CTGCCTTGGGATCCT | CAAGATGTGCTTTGT | CTACAACCTACACCT |
| GGGCCATGATGACAA | CCTCAGCCTGCCGAG | ATCGGATGGTTGCCG |
| TGCCTGGGATTGCAG | TGCAACCTCCCTGCC | CTCTGCCCGGCCACC |
| CTGTGTCTGTGTAGA | CCTCGGGCTCCAGTG | TCTGAAACATGTGCT |
| TCCATTTTGTTCTGT | CCCTCTGCGAGAAAC | CCATCCCATCTAGGA |
| ATGGTTGCCGGGTCT | CAGTGCTCAATGTTG | CCCGGCCGCCCAGTC |
| CGGGAGGTGGGGGGG | GGAGCGTCTCTGCCT | CTGCCCGCCTCGGCC |
| AAATGTGGGGAAAAG | GCCGTGATCTCGGCT | CCGGCCGCCATCCCG |
| CTCGGCCTGCCGAGT | CCTCTGCCCGGCCGC | TCTGGGAGGAGGTGG |
| TGCCATCTCGGCTCA | CATGCGGAGCCGAAG | GCCACCGCCCCGTCT |
| CCAAAGTGCCGAGAT | CTTCATTTTGTTCTG | CTTGGGATCCTGTTG |
| CCGCCCCTTCTGGGA | GAGGTGTGCCCAGCG | TGAGGAGCGTCTCTG |
| GGAAAAGATAGAGAA | GGAGCGTCTCTGCCC | CGCGCCGCCACGCCT |
| GGTGGGGAAAAGATA | TCTATAACCTTACCC | GAAGGCAGCATGCTC |
| TGCTGTGTCAACTCA | GGGTCCTCTGCCTAG | CCGCCATCTCGGCTC |
| CTTTTCATTTTGTTC | ACATGGGAGACTTTT | CAGGGTTAAATGGAT |
| GACATAGGAGACTCC | CTTTCTACGGTCTCC | GGAGGAGGTGGGGGG |
| CCCGTCTGGGAGGTG | ACCCCCAACCCTGTG | CTATTATCCTATGAC |
| GGGAAAAAATTGAGA | TGATGACAATGGCGG | CGCTGTGTTGGCCGG |
| GACTGTACTGCCGCC | TGGGAGGTGGGGGGC | GCTCGCTACAACCTC |
| CCCCGTGCTCTCTGA | CCTCCGCCCGGCCGC | GCTCGCTACAACCTA |
| GATTCTCCTGCCTCG | TGACGATGGCGGTTT | TAGAGAAATCGGATT |
| CCGGCCGCCACCCCG | TCTCCCTCTGTTGCC | TCTGCCCGCCTCGGC |
| GGTGGGGAAAAGATT | CGGCCGCCACCCCGT | AACAGCTCATTGAGA |
| GCCGAAGCTGGACTG | AAAAAAAATTAAAAA | CCGTCTGGGATGTGA |
| ACAGATGCTTGAAGG | AAATGGATTAAGGGC | CTGCCGAGTGCCTGG |
| GGTTTTTGTATTTTT | CATTGAGAACGGGCC | GGTGGGGGGCGCCTC |

TABLE 1-continued

Library of Antisense Oligonucleotides Targeting SVA

| | | |
|---|---|---|
| ATTAAGGGCGGTGCA | GGATGTGGGGAGCAC | CTCTCCCCTCTTTCT |
| GGAGTCTGGTTCACT | TGTGGGAAAAGAAA | GAACGGGCCATGATG |
| GTATTTTTTGGTGGA | CGTCTGGGAGGAGGT | GGAAGGCCGCAGGGT |
| CCGGGAGGAGGTGGG | CATCGTCTGAGATGT | ATCTGCCCGCCTCGG |
| TGGAGTGCAGTGGCG | CGGCCACCACCCCGT | ACATCCCCTCTCCG |
| AAATACTAAAAAAAA | CCCTCTCCGAGAAAC | CTCTCCCCTCTTTCC |
| ATCCCCAACCCTGTG | CCCGGCCACCGCCCC | AGCCGCCCCGTCTGG |
| CCGTCCGGGAGGAGG | GTACCCAACAGCTCA | CAAAGTGCTAAGATT |
| GCCCGGCCGCCCAGT | GGAGTCTCGTTCACT | GGAAGGCCGCAGGGA |
| AGAACGGGCCATGAT | ACACCCAAGAATGAT | CACGGTCTCCCTCTC |
| AGCGCCTCTTCCCGG | TCGTCTGGGATGTGG | ACCTTATCCCCAACC |
| CTTTGTTCACGTGTT | GCGAGAAACACCCAA | GGTGCAAGATGTGCT |
| GGAAAAAATTGAGAA | TCGTCTGGGATGTGA | ACCTTTGTTCACGTG |
| TGTACTGCCGCCATC | TCTCCCTCTGATGCC | TGTCCACTCAGGGTT |
| AGCCGCCTGCCTTGG | GGAAGTGAGGAGCGT | GCCGCAGGGTCCTCT |
| AAAGAAAGAGAGATC | CTCAATGTTGCCCAG | CCGGCCGCCCCTACT |
| GCGTCTCTGCCCGGC | CCTGGCCGCCCATCG | TGGGAGGTGTGCCCA |
| TGGATAGAAGTAGAC | GAAAAAATTGAGAAA | GCGCGCCGCCACGCC |
| ATGTGGGGAGCACCT | ATGGGAGACTTTTCA | CCTGGCTGCCCAGTC |
| GACACAAACACTGCG | AGCCCTAACCGCGA | CTGGGAGGAGGTGGG |
| TCCAGCTCCTGGCCT | CATCCCGTCTAGGAA | ATCTAGGAAGTGAGG |
| GGATGACAATGGCGG | TGTTACTGTGTCTGT | GTGCCCAACAGCTCA |
| AATTCTTCTGCCTTG | CGAGTGATCTGCCCG | ACTCAGTGCTCAATG |
| GATCAATAAAAAAAA | GGCCGCCCCGTCTGG | ATGTGCTGTGTCAAC |
| CTAATCTCAAGTACC | CTCCCGAGGTGCTGG | CCGCCCCGTCTGGGA |
| ACAACCACCTCCCAG | GTGTTGGCCGGGCCG | GTCTGGTTCACTCAG |
| GCCCCTAACCGCGAG | CCCAGGCTGGAGTGC | TGTGTAGAAAGAAGT |
| GACTGGTTTTCGTAT | GACCATTGAGAACGG | TTTTTTTTTGGTGGA |
| CGGGCCATGATGACA | TCTCATGCGGAGCCG | AAAGAAGTAGACATA |
| CTCCTGCCTCGGCCT | CACCACCCCGTCTGG | CCATCCCGTCTAGGA |
| CGGGCCATGATGACG | GTGAGGAGCGTCTCT | AAAGAAGTAGACATG |
| CCCTCTCATGCGGAG | AACCAGAGACCTTTG | GCCCGGCCGCCCCTA |
| TAGAAAGGCGGGAAA | CCCCTACTGGGAAGT | GAGAAATCGGATTGT |
| TAGAAAGGCGGGAAG | ACTATTATCCTATGA | CCCTCTCCCTCTTT |
| ATCTCGGCTCACTGC | AGTGAGGAGCGCCTC | GATGTGCTTTGTTAA |
| TCCCGGCCGCCATCC | TTGTTCTGTACTAAG | ATCAGATTGTTACTG |
| GGAGGTGGGGGGGTC | AAATCCCCTCTCCG | GTGAGGGGCGCCTCT |
| GTTGCCGAGGCTGGA | GCTTTGTGGAATAGA | GAAAGAAGTAGACAT |
| CTCGTTAAGAGTCAT | CAGATGCTTGAAGGC | CTGCCTCGGGCTCCA |
| TCTGATGCCGAGCCA | GCTGTGTCTGTGTAG | TATTTTTGGTGGAGA |
| ATGATGACGATGGCG | CTATTGTCCCATGAC | CCGCCCATCGTCTGG |
| TCTGATGCCGAGCCG | TCACTCAGTGCTCAA | CATCTCGGCTCACTG |
| CCTTCTGGGAAGTGA | TGGGGGCGCCTCTG | GACTGGTTTTTGTAT |
| ACTCAGGGTTAAATG | CCGGCCAGCCGCCCC | AAAGGTGGGGAAAAG |
| ATTCTTCTGCCTTGG | CTGGCCGCCCAGTCT | GATGACAATGGCGGC |
| TGCGAGAAACACCCA | AAGAAGTAGACATGG | CTGGGAGGTGTACCC |
| GCCTCCCGAGGTGCT | AAATTAAAAAAAAA | GGAATAGAAAGGGGG |
| TCACATGTTTATCTG | CTGCCCGGCCGCCAC | GAAAAATTCTTCTGC |
| GGATTAAGGGCGGTG | GGAGCCGAAGCTGGA | GATGACAATGGCGGT |
| CCACTCAGGGTTAAA | CCTCTGCCTGGCCGC | CTGCGAGAAACACCC |
| TTGTTAAACAGATGC | GGTCTCCAGCCCCTA | CCTCTCCCCTCTCTC |
| GCCTCCCGAGGTGCC | CTGCCCGGCCGCCAT | ACTTTTCATTTTGTT |
| ATCCCGTCTGGGAAG | AACAGATGCTTGAAG | CTCAGCCTGCCGAGT |
| GGAGGTGTACCCAAC | ATTGTCCCATGACCC | CTCACTCAGTGCTCA |
| TTTCTACGGTCTCCC | GTCCTATGACCCTGC | GCAGACGGAGTCTGG |
| CTGTGTAGAAAGAGG | GAGGCTGGACTGTAC | CTCTGCCCCGCCGCC |
| ACTCCCTAATCTTAA | TCCCTCTCATGCGGA | CACATGTTTATCTGC |
| AACCTCCACCTCCCA | GGGCCAGGATGACAA | GTTTTGGTGGAGACG |
| TTTTGTTCTGTACTA | TTTTGTATTTTTTGG | CTCATTGGGGATGGG |
| TCGGATGGTTGCCGT | GAAAAGATTGAGAAA | ATCCCCCTCTGTGAG |
| CAGCCTCTGCCCGGC | CTCTCCCTCTCCCTC | GCCCGGCCGCCATCC |
| GCCAGCCGCCCCGTC | CGTCTGGGATGTGGG | TGTATTTTTGGTGG |
| GTCAACTCAGGGTTA | GTATTTTGGTGGAG | GGCAGCATGCTCGTT |
| AAGAAAGGGGGAAA | TGCCTCGGGCTCCAG | CCAGCGGCTCATTGG |
| CCCTAATCTTAAGTA | GGCCGGGCTGGTCTC | GGGGGAAATGTGGGG |
| AGTAGACATAGGAGA | AACCTACACCTCCCA | AGGTGGGGGCGCCT |
| GCCGGGCCGGTCTCC | CTCTTTCTACGGTCT | TCGGCCTGCCGAGTG |
| CGGTCTCCCTCTGTT | CCATCCCGTCTGGGA | CGGGCCGGTCTCCAG |
| TACTAAGAAAAATTC | GGGACCTCTGCCTAG | AAGAAAGAGAGATCA |
| GGTTTTCGTATTTTT | CCCATCGTCTGGGAT | CTAGGAAAACCAGAG |
| AGGAAGTGAGGAGCG | CTGATGCCGAGCCAA | CGCCGCCCCGTCTGG |
| CAGTCTGGGAAGTGA | AGTGATCCGCCAGCC | CCCTCTGCCTGGCTG |
| ACATGGGAGACTTCA | TCTCTCCACTATTAT | GGGGCGCCTCTGCCC |
| CACCACTCCCTAATC | GCCATCCCATCTAGG | TGTTCACTTGTTTAT |
| TCGCTACAACCACCT | TTTCGCTGTGTTGGC | CTTCCCTCCACTATT |
| GTCATCACCACTCCC | CCGCCGCCCCGTCTG | ACTAAAAAAAAAAA |
| TGGACTGTACTGCTG | GTTTTTGTATTTTTG | AATGGATTAAGGGCG |

TABLE 1-continued

Library of Antisense Oligonucleotides Targeting SVA

| | | |
|---|---|---|
| GGCCTCCCAAAGAGC | TGTAGAAAGAAGTAG | CTCCCTGCCTGATTC |
| TTCGCTGTGTTGACC | CCGCCACGCCTGACT | GATGCTGTTAATCTA |
| TCGTTAAGAGTCATC | TGCCCAACAGCTCAT | GAAAGGCGGGAAAGG |
| GAAAAGAAAGAGAGA | GATGCCGAGCCGAAG | ACCCCGTCTGGGAAG |
| GGATGGGCCATGATG | TAAGATTGCAGCCTC | CTGGCCTCGAGTGAT |
| CCGAGCCAAAGCTGG | TCGCTACAACCTCCA | CGCCGTGTTGGCCGG |
| CCTCTCCCTGTCCCC | GTTTTTGTATTTTTT | CCCAGCGGCTCATTG |
| TTTGTTCACATGTTT | ATCCTGTTGATCTGT | GTGCTAAGATTGCAG |
| GGCCGCCCCTACTGG | GCCGAGATTGCAGCC | AGGGACACAAACACT |
| CTGCCGAGTGCCTGC | TCAGTGCTCAATGGT | ATGCTCGTTAAGAGT |
| GGCCAGGATGACAAT | ACCCTGCCAAATCCC | AGGTGTGCCCAACAG |
| ACGGGGTTTCGCTGT | TCCACTATTGTCCCA | TTTTGTCGAAAAGAA |
| CATGACCCTGCCAAA | GGACTGTACTGCTGC | CGGCCGCCCAGTCTG |
| GTGAGAAACACCCAA | TGTGTGGATAGAAGT | CTCTGATGCCGAGCC |
| CCTGTGCTCTCTGAA | TCTGGGAGGTGTACC | CCTTGGGATGCTGTT |
| AGTAATCAGGGACAC | TCATTGAGAACGGGC | CTCCCTAATCTTAAG |
| CCAACCCTGTGCTCT | GATGACGATGGCGGT | ATCCCCCTCTCCGAG |
| TGAGAAATCGGATGG | CCTGGGATTGCAGGC | GCCTGGCCGCCCAGT |
| CCACTCCCTAATCTT | ACGGAGTCTCGTTCA | TTGAGAAATCGGATG |
| TGCTTTGTTAAACAG | GCAGGCGCGCGCCGC | AGAAAGAAGTAGACA |
| TCAATGTTGCCCAGG | GAGCGCCTCTTCCCG | GCCCGGCCGCCACCC |
| CCCCTCTCTCCACGG | CCTCTGCCCGGCCAG | CCCGAGGTGCTGGGA |
| CCTCTCATGCGGAGC | CCAGCCGCCTGCCTT | GGGGGGCGCCTCTGC |
| TGGCCTCGAGTGATC | GGAGGTGTGCCCAAC | GTGGATAGAAGTAGA |
| CAACCCCGTGCTCTC | AAGAAAAATTCTTCT | CCGGCCGCCCATCGT |
| CCACTCCCTAATCTC | TACCCCCAACCCCGT | TCTCAAGTACCCAGG |
| AATAAATACTAAAAA | TTGCAGACGGAGTCT | TTTCGTTTTTTTTTG |
| CGTGCTCTCTGAAAC | GACCTTCTCTCCACT | GTTTCGCCGTGTTGG |
| GCCCCGTCTGGGAGG | ACCACCTCCCAGCCG | CGGCTCGCTGCAACC |
| ATGACCCTGCCAAAT | TCTCCCCTCTTTCCA | CCGTGCTCTCTGAAA |
| TGAGGAGCGCCTCTG | CGTCTAGGAAGTGAG | GCCTGACTGGTTTTG |
| GAGGTGAGGGGCGCC | GCGGTTTTGTGGAAT | GCCTGACTGGTTTTC |
| AATCAGGGACACAAA | CCTGACTGGTTTTCG | GTTAAACAGATGCTT |
| TGAGGAGCGCCTCTT | CCCCGTCTGGGAAGT | GGAGACTCCATTTTG |
| CTGGGATTGCAGACG | TACTGCCGTGATCTC | GCCGGGCTGGTCTCC |
| GCCCATCGTCTGAGA | CGAATAGAAAAGGGG | GCCTGACTGGTTTTT |
| TGCCTAGGAAAACCA | GGGAGACTTTTCATT | AGAAAGGGGGGAAAG |
| CCCATCTAGGAAGTG | TGCCCGGCCGCCACC | GGATGCTGTTAATCT |

TABLE 1-continued

Library of Antisense Oligonucleotides Targeting SVA

| | | |
|---|---|---|
| GAAGGCCGCAGGGTC | ATGGATTAAGGGCGG | TCCAGTGATTCTCCT |
| GGATTGCAGGCGCGC | TACGGTCTCCCTCTG | GAAGTAGACATGGGA |
| CAATAAAAAAAAAAA | CCCGCCCGGCCAGCC | TTCGTTTTTTTTTGG |
| GCTGGAGTGCAGTGG | GGAGACTTCATTTTG | CCCCGTCTGGGATGT |
| GCCCGGCCGCCCCTT | TCTACGGTCTCCCTC | TACTGCTGCCATCTC |
| GGCTCATTGGGGATG | ATTCTCCTGCCTCAG | AGGTGGGGGGGTCAG |
| TGCCGCCATCTCGGC | CGGCCGCCCATCGTC | GATTGCAGACGGAGT |
| AGAGGTAGACATGGG | AGCTGGACTGTACTG | CAGGATGACAATGGC |
| GGCGGCTTTGTGGAA | CCACTATTGTCCTAT | ACTATTGTCCCATGA |
| CAGCTCCTGGCCTCG | ATGCTGTTAATCTAT | AGCTCCTAACCGCGA |
| TCGTATTTTTTTGGT | GCCTCAGCCTGCCGA | CGATTGCAGGCACGC |
| GTGCCTGCGATTGCA | GGGGTTTCGCTGTGT | TCCCTCTCCCCTCTC |
| GAAATCGGATTGTTG | ACCACCCCGTCTGGG | CCATTGAGAACGGGC |
| AATGGCGGCTTTGTG | TCTGCCTAGGAAAAC | GTTCACGTGTTTATC |
| GAAAGGGGGGAAAGG | CGGTTTTGTGGAATA | TCCCTCTCCCCTCTT |
| GCCGAGCCGAGGCTG | GACGGAGTCTCGCTC | GACTGTACTGCCGTG |
| CACTCCCTAATCTCA | CCGCCATCCCGTCTA | ATCCTATGACCCTGC |
| TTGCCGAGGCTGGAC | GAGCCGGATTGCAGC | TTGGGATCCTGTTGA |
| TGTCGAAAAGAAAAG | GCGGTGCAAGATGTG | TCGGCCTCCCGAGGT |
| CGCTGCAACCTCCCT | CATAGGAGACTCCAT | TGTCAACTCAGGGTT |
| GCCTGCGATTGCAGG | CCTCCACCTCCCAGC | CTTACCCCCAACCCT |
| GATAGAAGTAGACAT | AAAGAGCCGGATTGC | TGCTCGTTAAGAGTC |
| CCTGCCTTGGCCTCC | GAACGGGCCAGGATG | AGGGTGGGGAAAAAA |
| TCTCCAGCTCCTAAC | GGTGGGGGGGTCAGC | CTCAATGGTGCCCAG |
| GGCTCACTGCAACCT | GCCCCGTCTGGGATG | TTTCCACGGTCTCCC |
| ATAGAAAGGGGGGAA | CGAGGTGCCGGGATT | GCCGTGTCTGTGTAG |
| GGCCGCCATCCCATC | TCTGTGTGGATAGAA | GGATCCTGTTGATCT |
| TAATCAGGGACACAA | CTCGCTGCAACCTCC | TCCCTGCCTGATTCT |
| CGCTCACTCAGTGCT | GATTCTCCTGCCTCA | CTCCCTCTGTTGCCG |
| AGAAGTAGACATAGG | CTATTGTCCTATGAC | AGGAGCGCCTCTGCC |
| AATGGTGCCCAGGCT | CTCCACGGTCTCCCT | AGAAAGGCGGGAAGG |
| CCCAAGAATGATCAA | GCAGCATGCTCGTTA | GCCGCCCCGTCTGGG |
| TGTGAGAAACACCCA | TCCCTCTCCCTGTCC | CCGTCTGGGAGGTGG |
| CACTCAGTGCTCAAT | CTGTGCTCTCTGAAA | CCGTCTGGGAAGTGA |
| GTGCTGTGTCCACTC | CCGAGCCGAAGCTGG | GACGGGGTTTCGCTG |
| CCCTCTTTCCACGGT | ACTGTACTGCCGTGA | CAGTGCTCAATGGTG |
| TGCTGCCATCTCGGC | GAGTGCAGTGGCGTG | TCCTGACCGCGAGTG |
| GGGGTTTCGCCGTGT | TGAGAACGGGCCATG | CCTCCACTATTGTCC |
| CGGTTTTGTCGAATA | AGTGAGGAGCCCCTC | TGTCTGTGTAGAAAG |

TABLE 1-continued

Library of Antisense Oligonucleotides Targeting SVA

| | | |
|---|---|---|
| TGATGCCGAGCCGAG | CGGCTCATTGGGGAT | CTGTGTGGATAGAAG |
| TGATGCCGAGCCGAA | TGGTTTTGGTGGAGA | GGAGGTGGGGGCGC |
| CTCAAGTAATCAGGG | CAAATCCCCTCTGC | GCGATTGCAGGCACG |
| AAGCTGGACGGTACT | A

TABLE 1-continued
Library of Antisense Oligonucleotides Targeting SVA

| | | |
|---|---|---|
| CCAGCCTCGGCCTCC | CCCGGCCGCCACCCC | AGACGGAGTCTGGTT |
| ATTGGGGATGGGCCA | AATCTCAAGTAATCA | ACCCTGTGCTCTCTG |
| GTTGGCCGGGCCGGT | GGCTCGCTACAACCT | TGGGAGACTTTTCAT |
| GTGCTCTCTGAAACA | AGGCACGCGCCGCCA | TCTCTGAAACATGTG |
| GATTGCAGGCACGCG | CTGTACTGCTGCCAT | GGTACTGCTGCCATC |
| TCGCTGTGTTGGCCG | GGCGGTGCAAGATGT | AAACATGTGCTGTGT |
| ACGGGCCATGATGAC | CTACTGGGAAGTGAG | GGAGCCCCTCTGCCC |
| TATCAATAAAAAAAA | GGGTTAAATGGATTA | AAATTGAGAAATCGG |
| CCATGATGACAATGG | CTCGGCTCACTGCAA | ACACCTCCCAGCCGC |
| TACTGCCGCCATCTC | TTTTCGTATTTTTTT | TGGTTGCCGTGTCTG |
| CGCCCAGTCTGGGAA | TTGTTCACTTGTTTA | CGAGCCAAAGCTGGA |
| TATCTGCTGACCTTC | CACCGCCCCGTCTGG | CGGAGCCGAAGCTGG |
| GCCCCTTCTGGGAAG | TGCCGAGCCAAAGCT | GCCCCTCTGCCTGGC |
| CTCATTGAGAACGGG | TCGCTCACTCAGTGC | GCCGGGATTGCAGAC |
| TATTGTCCCATGACC | CAATAAAAAAATTA | GTCTCCCTCTGATGC |
| GCCGGGTCTGTGTGG | TCCCCTCTTTCTACG | GTAATCAGGGACACA |
| AGTGATCTGCCCGCC | ATGACCCTGCCACAT | GTGGGGAGCGCCTCT |
| GATGGTTGCCGGGTC | CCGCCACCCCGTCTG | GCGAGTGATCTGCCC |
| TTACCCCCAACCCCG | GGGCTGGTCTCCAGC | CCGTCTAGGAAGTGA |
| CGCCCCGTCCGGGAG | TGCCAAATCCCCCTC | GTTGCCGGGTCTGTG |
| CCACCCCGTCTGGGA | ACTCCCTAATCTCAA | GAGAACGGGCCATGA |
| TGGGAGGTGGGGGGG | CGCCCATCGTCTGAG | GTTGATCTGTGACCT |
| GTCTCCAGCTCCTAA | | |
| AAGATTGCAGCCTCT | | |
| GTGCCGGGATTGCAG | | |
| ATAACCTTACCCCCA | | |
| GTTAAGAGTCATCAC | | |
| GAAGTGAGGAGCCCC | | |
| GTGTCTGTGTAGAAA | | |
| GGGGAGCGCCTCTGC | | |
| TTGACCGGGCTGGTC | | |
| GGTGGGGAAAAAATT | | |
| GTCCGGGAGGTGGGG | | |
| GGGGGCGCCTCTGCC | | |
| CGCTACAACCTCCAC | | |
| GGGGAAAAGATAGAG | | |
| AACACCCAAGAATGA | | |
| CTGTTAATCTATAAC | | |
| TGTGTTGACCGGGCT | | |
| ACCGCGAGTGATCTG | | |
| TGGGGGGGTCAGCCC | | |
| TCCCAAAGTGCTAAG | | |
| CTCAGGGTTAAATGG | | |
| TGGCCGGGCCGGTCT | | |
| TCCTGCCTCAGCCTG | | |
| GTCTCTGCCTGGCCG | | |
| TCACTGCAACCTCCC | | |
| GGAGCCCCTCTGCCT | | |

AONS targeting an ALU present in a mammalian genome can be generated using no more than routine methods.

By "agent" is meant a peptide, nucleic acid molecule, or small compound. In one embodiment, the agent is an inhibitory nucleic acid molecule, such as an antisense oligonucleotide.

By "ameliorate" is meant decrease, suppress, attenuate, diminish, arrest, or stabilize the development or progression of a disease. In one embodiment, the disease affects the central nervous system and is associated with the insertion of a transposable element into a mammalian genome.

By "alteration" is meant a change (increase or decrease) in the sequence, expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include Batten disease or any genetic disorder associated with a heterozygous mutation in a first allele of a gene and the insertion of a transposable element affecting a second allele of the gene.

By "effective amount" is meant the amount of an agent of the invention required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein. In one embodiment, an antisense RNA comprises at least about 5, 10, 11, 12, 13, 14, 15, 16, 17, 18, 19, 20, 21, 22, 23, 24, 25, 26, 27, 28, 29, 30, 35 or more nucleobases complementary to a target sequence. In one embodiment, the oligonucleotide comprises 18-22 nucleobases.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

"Anti-sense oligonucleotide set" means a number of oligonucleotides that may be used, for example, in a therapeutic composition. A set of anti-sense oligonucleotide set would comprise at least 2, 3, 4, 5, 6, 7, 8, 9, 10, 11, 12, 13, 14, 15, 16, 18, 20, 30, 40, 50, 60, 80, 100, 200, 250, 300, 400, 500, 600, 700, 800, 900, 1000, 1500, 2000, or more AONs.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 10, 15 or 16 amino acids, at least about 20 amino acids, more preferably at least about 25 amino acids, and even more about 35 amino acids, about 50 amino acids, or about 100 amino acids. For nucleic acids, the length of the reference nucleic acid sequence will generally be at least about 5, 10, 15, 20, or 50 nucleotides, at least about 60 nucleotides, more preferably at least about 75 nucleotides, and even more preferably about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a polynucleotide that recognizes and binds a complementary sequence of the invention, but which does not substantially recognize and bind other molecules in a sample, for example, a biological sample, which naturally includes other polynucleotide sequences. An antisense oligonucleotide may specifically bind its perfect complement or a sequence to which it is not perfectly complementary. In one embodiment, the antisense oligonucleotide specifically binds a polynucleotide that comprises 1, 2, 3, 4, 5 or more bases that are not perfectly complementary to the anti-sense oligonucleotide.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 5I discloses SEQ ID NOS: 2604-2606, 2611, 2604, 2607, 2606, 2608, 2607 and 2609, respectively, in order of appearance.

FIG. 6A shows the location and chemistry of antisense oligonucleotides that were designed to block the splice acceptor site or exonic splice enhancer (ESE) elements. The ESE elements were predicted by RESCUE-ESE and ESE-finder.

FIG. 6B is a graph showing fold change in the ratio of the normal exon6-exon7 splicing to the abnormal exon6-i6 splicing in response to antisense oligonucleotide transfection, measured by multiplex RT-PCR followed by gel electrophoresis band quantitation. Asterisks indicate statistically significant (P<0.05) difference from the no transfection ("Cell") control.

FIG. 6C shows an example gel image used to obtain the results for panel B. "Ratio" indicates the ratio of the normal exon6-exon7 splicing to the abnormal exon6-i6 splicing, measured by gel band quantitation.

FIG. 8A shows the ratio of the normal exon6-exon7 splicing to the abnormal exon6-i6 splicing in response to antisense oligonucleotide transfection into the subject-derived fibroblast, measured by multiplex qRT-PCR. FIG. 8B is the same as FIG. 8A, but for the subject-derived lymphoblasts.

FIG. 12 is a table that provides a genomic alignment analysis showing that milasen/TY777 has less predicted off-targets than nusinersen. All possible subsequences of a given length were taken from the milasen/TY777 sequence and aligned to the reference human genome by using BLAST. The number and identity of the off-target matches are shown.

FIG. 13 includes lysosomal function assays showing that the subject-derived fibroblasts have abnormal lysosomal function and milasen/TY777 effectively restores the dysfunction.

DETAILED DESCRIPTION OF THE INVENTION

Figure 1:
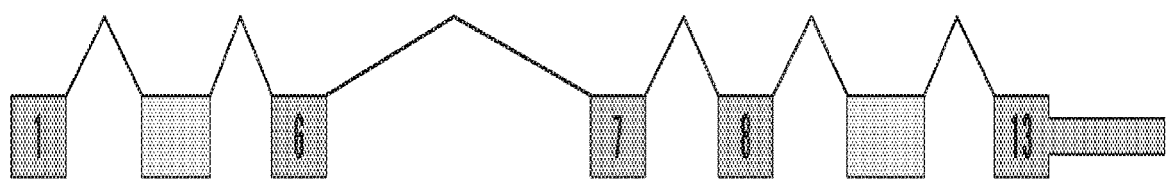
FIG. 1 is a schematic diagram showing the normal intron exon structure of the MFSD8 gene, and the position of the SVA insertion in the proband's MFSD8 gene. MFSD8 is also referred to as CLN7.
Figure 1:
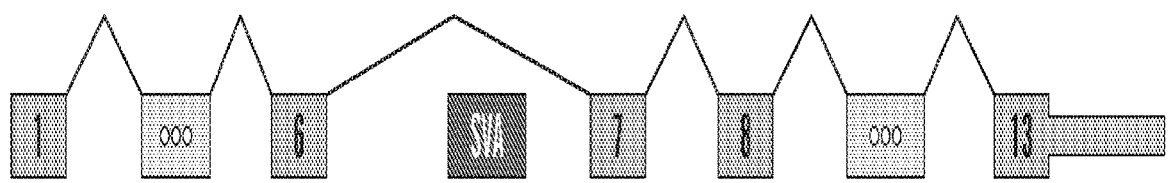

The invention features antisense oligonucleotides and methods of using such antisense oligonucleotide to correct the deleterious effects of transposable element insertion in a mammalian genome.

The invention is based, at least in part, on the discovery of a case of neuronal ceroid lipofuscinosis (NLS) secondary to a cryptic, mobile DNA element (retrotransposon) insertion. Retrotransposon insertions are missed by current clinical sequencing approaches (Sanger, panel, or whole exome sequencing), but can be detected by whole genome sequencing in concert with specialized algorithms that have been developed. Detecting these mutations is of critical importance because they cause disease by serving as "poison exons"—inducing mis-splicing of the normal gene product into the retrotransposon itself, leading to a truncated gene product. The invention provides exon skipping oligonucleotides that can block incorporation of retrotransposon-induced poison exons, thus restoring normal gene function. These oligonucleotides will be used to treat virtually any disease associated with retrotransposon insertion.

Batten Disease Case Study

The impetus for developing oligonucleotides for the treatment of diseases associated with retrotransposon insertion was the identification of a child displaying symptoms of a progressive neurological decline, including worsening gait, language and behavioral regression, and severe loss of vision. Brain and spine MRI identified progressive cerebellar atrophy. Other clinical features include fingerprint inclusions in endothelial cells and sweat ducts. These findings are pathologically consistent with Neuronal Ceroid Lipofuscinosis ("NCL") also termed Batten Disease, which is a rare, recessive disorder resulting in the progressive degeneration of the brain and retina. This degeneration results from the accumulation of ceroid lipofuscin in lysosomes. Symptoms of the disorder include blindness, seizures, and motor and cognitive decline.

Sequence analysis on a biological sample obtained from the child identified the presence of a heterozygous mutation in MFSD8, designated 1102G.C, which is predicted to result in an amino acid substitution (Asp368His). This variant is located at the last nucleotide of an exon and is predicted to result in defective splicing. This variation was associated in the homozygous condition with the presence of NCL. Because Batten disease is recessive, the presence of only a single mutation in an affected individual is entirely unexpected. It begs the question of where the second allele is? Whole genome sequencing was carried out on DNA obtained from the proband. This sequence was compared with sequences obtained from her parents and a sibling. Results of the whole genome sequencing identified the presence of a retrotransposon insertion into the proband's second allele of MFSD8, which introduced a cryptic exon including a stop codon that resulted in truncation of the NIFSD8 protein.

The invention provides one or more antisense oligonucleotides (e.g., a set of antisense oligonucleotides) targeting a deleterious splice acceptor site associated with a retrotransposon insertion, and methods of using the antisense oligonucleotides for the treatment of diseases or disorders associated with a retrotransposon insertion.

Retrotransposons

Retrotransposons make use of an RNA-mediated transposition process. Retroelements are subdivided into two major groups: those containing long-terminal repeats, LTR retroelements, and all others, lumped into the category of non-LTR retroelements. Non-LTR retrotransposons include autonomous and non-autonomous members. The autonomous long interspersed element-1 (LINE-1 or L1), and its non-autonomous partners, SVA and Alu are the only elements currently identified as having retrotranspositional activity in the human genome Human L1 is about 6 kb in length and encodes two open reading frames, ORF1 and ORF2 that are both required for L1 retrotransposition. SINE-VNTR-Alus (SVA) are non-autonomous retrotransposons that are associated with disease in humans. SVAs are evolutionarily young and presumably mobilized by the LINE-1 reverse transcriptase in trans. SVAs are currently active and may impact the host through a variety of mechanisms including insertional mutagenesis, exon shuffling, alternative splicing, and the generation of differentially methylated regions (DMR). Each domain of SVA is derived from either a retrotransposon or a repeat sequence. A canonical SVA is on average ~2 kilobases (kb), but SVA insertions may range in size from 700-4000 basepairs (bp). SVA disease insertions are associated with exon-skipping, deletion of genomic DNA, and reduced or absent mRNA expression.

The present invention provides methods of treating disease and/or disorders or symptoms thereof associated with the insertion of a retrotransposon (e.g., SVA or Alu), which comprise administering a therapeutically effective amount of a pharmaceutical composition comprising an antisense oligonucleotide targeting a retrotransponson (e.g., SVA or Alu) herein to a subject (e.g., a mammal such as a human). Thus, one embodiment is a method of treating a subject suffering from or susceptible to a disease or disorder or symptom thereof associated with the insertion of a TE. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of an antisense oligonucleotide described herein, or a composition comprising such antisense oligonucleotides. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the antisense oligonucleotides herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which TEs may be implicated.

In one embodiment, the invention provides a method of monitoring treatment progress. The method includes the step of determining a level of diagnostic marker (Marker) (e.g., a protein whose expression or activity is disrupted by a TE) in a subject suffering from or susceptible to a disorder or symptoms thereof associated with TE insertion, in which the subject has been administered a therapeutic amount of an antisense oligonucleotide herein sufficient to treat the disease or symptoms thereof. The level, length or activity of the Marker determined in the method can be compared to the level, length or activity of the Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Oligonucleotides and Other Nucleobase Oligomers

In one embodiment, an oligonucleotide or nucleobase oligomer of the invention comprises 2'-modified oligonucleotides where some or all internucleotide linkages are modified to phosphorothioates or phosphodiester (PO). The presence of methylphosphonate modifications increases the affinity of the oligonucleotide for its target RNA and thus reduces the IC50. This modification also increases the nuclease resistance of the modified oligonucleotide. It is understood that the methods and reagents of the present invention may be used in conjunction with any technologies that may be developed, including covalently-closed multiple antisense (CMAS) oligonucleotides (Moon et al., Biochem J. 346:295-303, 2000; PCT Publication No. WO 00/61595), ribbon-type antisense (RiAS) oligonucleotides (Moon et al., J. Biol. Chem. 275:4647-4653, 2000; PCT Publication No. WO 00/61595), and large circular antisense oligonucleotides (U.S. Patent Application Publication No. US 2002/0168631 A1).

As is known in the art, a nucleoside is a nucleobase-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure; open linear structures are generally preferred. Within the oligonucleotide structure, the phosphate groups are commonly referred to as forming the backbone of the oligonucleotide. The normal linkage or backbone of RNA and DNA is a 3' to 5' phosphodiester linkage.

Specific examples of preferred nucleobase oligomers useful in this invention include oligonucleotides containing modified backbones or non-natural internucleoside linkages. As defined in this specification, nucleobase oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers.

Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriest-ers, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other nucleobase oligomers, both the sugar and the internucleoside linkage, i.e., the backbone, are replaced with novel groups. The nucleobase units are maintained for hybridization with a TE. One such nucleobase oligomer, is referred to as a Peptide Nucleic Acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are described, for example, in "Peptide Nucleic Acids: Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In particular embodiments of the invention, the nucleobase oligomers have phosphorothioate backbones and nucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$—. In other embodiments, the oligonucleotides have morpholino backbone structures described in U.S. Pat. No. 5,034,506.

Nucleobase oligomers may also contain one or more substituted sugar moieties. Nucleobase oligomers comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$NH$_2$, O($CH_2$)$_n$$CH_3$, O($CH_2$)$_n$ON$H_2$, and O($CH_2$)$_n$ON[($CH_2$)$_n$$CH_3$)]2, where n and m are from 1 to about 10. Other preferred nucleobase oligomers include one of the following at the 2' position: C1 to C10 lower alkyl, substituted lower alkyl, alkaryl, aralkyl, O-alkaryl, or O-aralkyl, SH, SCH$_3$, OCN, Cl, Br, CN, CF$_3$, OCF$_3$, SOCH$_3$, SO$_2$CH$_3$, ONO$_2$, NO$_2$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleobase oligomer, or a group for improving the pharmacodynamic properties of an nucleobase oligomer, and other substituents having similar properties. Preferred modifications are 2'-O-methyl and 2'-methoxyethoxy (2'-O—$CH_2CH_2OCH_3$, also known as 2'-O-(2-methoxyethyl) or 2'-MOE). Another desirable modification is 2'-dimethylaminooxyethoxy (i.e., O($CH_2$)$_2$ON($CH_3$)$_2$), also known as 2'-DMAOE. Other modifications include, 2'-aminopropoxy (2'-O$CH_2CH_2CH_2NH_2$) and 2'-fluoro (2'-F). Similar modifications may also be made at other positions on an oligonucleotide or other nucleobase oligomer, particularly the 3' position of the sugar on the 3' terminal nucleotide or in 2'-5' linked oligonucleotides and the 5' position of 5' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleobase oligomers may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo (e.g., 5-bromo), 5-trifluoromethyl and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of an antisense oligonucleotide of the invention. These include 5-substituted pyrimidines, 6-azapyrimidines, and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are desirable base substitutions, even more particularly when combined with 2'-O-methoxyethyl or 2'-O-methyl sugar modifications. Representative United States patents that teach the preparation of certain of the above noted modified nucleobases as well as other modified nucleobases include U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

Another modification of a nucleobase oligomer of the invention involves chemically linking to the nucleobase oligomer one or more moieties or conjugates that enhance the activity, cellular distribution, or cellular uptake of the oligonucleotide. Such moieties include but are not limited to lipid moieties such as a cholesterol moiety (Letsinger et al., Proc. Natl. Acad. Sci. USA, 86:6553-6556, 1989), cholic acid (Manoharan et al., Bioorg. Med. Chem. Let, 4:1053-1060, 1994), a thioether, e.g., hexyl-S-tritylthiol (Manoharan et al., Ann. N.Y. Acad. Sci., 660:306-309, 1992; Manoharan et al., Bioorg. Med. Chem. Let., 3:2765-2770, 1993), a thiocholesterol (Oberhauser et al., Nucl. Acids Res., 20:533-538: 1992), an aliphatic chain, e.g., dodecandiol or undecyl residues (Saison-Behmoaras et al., EMBO J., 10:1111-1118, 1991; Kabanov et al., FEBS Lett., 259:327-330, 1990; Svinarchuk et al., Biochimie, 75:49-54, 1993), a phospholipid, e.g., di-hexadecyl-rac-glycerol or triethylammonium 1,2-di-0-hexadecyl-rac-glycero-3-H-phosphonate (Manoharan et al., Tetrahedron Lett., 36:3651-3654, 1995; Shea et al., Nucl. Acids Res., 18:3777-3783, 1990), a polyamine or a polyethylene glycol chain (Manoharan et al., Nucleosides & Nucleotides, 14:969-973, 1995), or adamantane acetic acid (Manoharan et al., Tetrahedron Lett., 36:3651-3654, 1995), a palmityl moiety (Mishra et al., Biochim. Biophys. Acta, 1264:229-237, 1995), or an octadecylamine or hexylamino-carbonyl-oxycholesterol moiety (Crooke et al., J. Pharmacol. Exp. Ther., 277:923-937, 1996. Representative United States patents that teach the preparation of such nucleobase oligomer conjugates include U.S. Pat. Nos. 4,587,044; 4,605,735; 4,667,025; 4,762,779; 4,789,737; 4,824,941; 4,828,979; 4,835,263; 4,876,335; 4,904,582; 4,948,882; 4,958,013; 5,082,830; 5,109,124; 5,112,963; 5,118,802; 5,138,045; 5,214,136; 5,218,105; 5,245,022; 5,254,469; 5,258,506; 5,262,536; 5,272,250; 5,292,873; 5,317,098; 5,371,241; 5,391,723; 5,414,077; 5,416,203; 5,451,463; 5,486,603; 5,510,475; 5,512,439; 5,512,667; 5,514,785; 5,525,465; 5,541,313; 5,545,730; 5,552,538; 5,565,552; 5,567,810; 5,574,142; 5,578,717; 5,578,718; 5,580,731; 5,585,481; 5,587,371; 5,591,584; 5,595,726; 5,597,696; 5,599,923; 5,599,928; 5,608,046; and 5,688,941, each of which is herein incorporated by reference.

The present invention also includes nucleobase oligomers that are chimeric compounds. "Chimeric" nucleobase oligomers are nucleobase oligomers, particularly oligonucleotides, that contain two or more chemically distinct regions, each made up of at least one monomer unit, i.e., a nucleotide in the case of an oligonucleotide. These nucleobase oligomers typically contain at least one region where the nucleobase oligomer is modified to confer, upon the nucleobase oligomer, increased resistance to nuclease degradation, increased cellular uptake, and/or increased binding affinity for the target nucleic acid. An additional region of the nucleobase oligomer may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of nucleobase oligomer inhibition of gene expression. Consequently, comparable results can often be obtained with shorter nucleobase oligomers when chimeric nucleobase oligomers are used, compared to phosphorothioate deoxyoligonucleotides hybridizing to the same target region.

Chimeric nucleobase oligomers of the invention may be formed as composite structures of two or more nucleobase oligomers as described above. Such nucleobase oligomers, when oligonucleotides, have also been referred to in the art as hybrids or gapmers. Representative United States patents that teach the preparation of such hybrid structures include U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The nucleobase oligomers used in accordance with this invention may be conveniently and routinely made through the well-known technique of solid phase synthesis. Equipment for such synthesis is sold by several vendors including, for example, Applied Biosystems (Foster City, Calif). Any other means for such synthesis known in the art may additionally or alternatively be employed. It is well known to use similar techniques to prepare oligonucleotides such as the phosphorothioates and alkylated derivatives.

The nucleobase oligomers of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The nucleobase oligomers of the invention encompass any pharmaceutically acceptable salts, esters, or salts of such esters, or any other compound that, upon administration to an animal, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "pharmaceutically acceptable salts" refers to salts that retain the desired biological activity of the parent compound and do not impart undesired toxicological effects thereto. Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., J. Pharma Sci., 66:1-19, 1977). The base addition salts of acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides and other nucleobase oligomers, suitable pharmaceutically acceptable salts include (i) salts formed with cations such as sodium, potassium, ammonium, magnesium, calcium, polyamines such as spermine and spermidine, etc.; (ii) acid addition salts formed with inorganic acids, for example hydrochloric acid, hydrobromic acid, sulfuric acid, phosphoric acid, nitric acid and the like; (iii) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (iv) salts formed from elemental anions such as chlorine, bromine, and iodine.

The present invention also includes pharmaceutical compositions and formulations that include the nucleobase oligomers of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral, or parenteral. Parenteral administration includes intravenous, intraarterial, subcutaneous, intraperitoneal, or intramuscular injection or infusion; or intracranial, e.g., intrathecal or intraventricular, administration.

Test Compounds and Extracts

In one aspect, the invention provides methods of screening for agents that have the ability to inhibit splicing with a retrotransposon. Thus, in various embodiments, a test compound will be an antisense oligonucleotide that targets a retrotransposon splice site or a retrotransposon splice enhancer site. Additionally, other compounds may be screened for the desired activity.

In general, small molecule compounds are known in the art or are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. For example, a library of 8,000 novel small molecules is available, which was created using combinatorial methods of Diversity-Oriented Synthesis (DOS) (corner et al, Proc Natl Acad Sci USA 108, 6751 (Apr. 26, 2011; Lowe et al, J Org Chem 77, 7187 (Sep. 7, 2012); Marcaurelle et al, J Am Chem Soc 132, 16962 (Dec. 1, 2010))— to investigate chemical compounds not represented in traditional pharmaceutical libraries (Schreiber, S. L. (2000). Science 287, 1964-1969; Schreiber et al, Nat Biotechnol 28, 904 (September, 2010), each of which is herein incorporated by reference in their entirety). Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int.*

Ed. Engl. 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Libraries of compounds may be presented in solution (e.g., Houghten, Biotechniques 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:63786382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is identified as containing a compound of interest, further fractionation of the positive lead extract is necessary to isolate chemical constituents responsible for the observed effect. Thus, the goal of the extraction, fractionation, and purification process is the careful characterization and identification of a chemical entity within the crude extract that achieves a desired biological effect. Methods of fractionation and purification of such heterogenous extracts are known in the art.

Small molecules of the invention preferably have a molecular weight below 2,000 daltons, more preferably between 300 and 1,000 daltons, and most preferably between 400 and 700 daltons. It is preferred that these small molecules are organic molecules.

Therapy

Therapy may be provided wherever therapy associated with a genetic disorder is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of genetic disorder being treated, the age and condition of the patient, the type of the patient's disease, and how the patient's body responds to the treatment.

An antisense oligonucleotide or antisense nucleobase oligomer of the invention may be administered within a pharmaceutically-acceptable diluent, carrier, or excipient, in unit dosage form. Conventional pharmaceutical practice may be employed to provide suitable formulations or compositions to administer the compounds to patients suffering from a disease that is associated with insertion of a transposable element. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for TE antisense oligonucleotides include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a disease or condition. The preferred dosage of a nucleobase oligomer of the invention is likely to depend on such variables as the type and extent of the disorder, the overall health status of the particular patient, the formulation of the compound excipients, and its route of administration.

For any of the methods of application described above, a nucleobase oligomer of the invention is desirably administered intravenously or is applied to the site of the needed intervention (e.g., by injection).

Kits

The invention provides kits for the treatment or prevention of a genetic disease associated with insertion of a transposable element. In one embodiment, the kit includes a pharmaceutical pack comprising an effective amount of an antisense oligonucleotide that targets a splice acceptor site associated with insertion of a transposable element or which targets a sequence associated with the transposable element (e.g., SVA sequence). Preferably, the compositions are present in unit dosage form. In some embodiments, the kit comprises a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired compositions of the invention or combinations thereof are provided together with instructions for administering them to a subject having a genetic disorder associated with insertion of a transposable element. The instructions will generally include information about the use of the compounds for the treatment or prevention of the genetic disorder. In other embodiments, the instructions include at least one of the following: description of the oligonucleotide(s); dosage schedule and administration for treatment of a genetic disorder or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology"

(Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Antisense Oligonucleotides for the Treatment of Genetic Disease

A child presented with a severe rapidly progressing neurodegenerative disease affecting the brain and retina, whose symptoms were consistent with Batten Disease, which is a rare recessive genetic disorder. Sequence analysis of a biological sample from the child identified the presence of a heterozygous mutation, heterozygous mutation in MFSD8, designated 1102G.C, which is predicted to results in an amino acid substitution (Asp368His). This variant is located at the last nucleotide of an exon and is predicted to result in defective splicing. It had previously been reported in the homozygous state in one patient affected with NCL. It was also reported in the heterozygous state with another missense variant in a patient with macular dystrophy.

Figure 2:
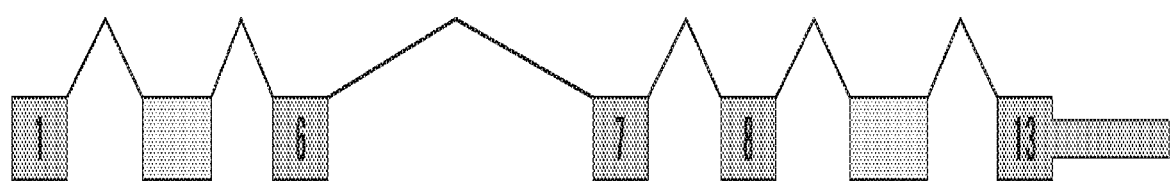
FIG. 2 is a schematic diagram showing the splicing of native MFSD8 and the MFSD8 gene truncation resulting from the introduction of a stop codon in a cryptic exon associated with insertion of the SVA transposon.
Figure 2:
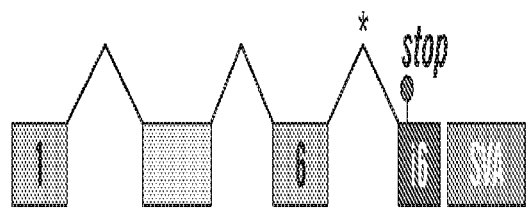

The presence of a single heterozygous mutation in an affected patient was unexpected given that Batten disease is a recessive genetic disorder. This begs the question of where the second allele is? Whole genome sequencing of the affected child, parents and a sibling identified the insertion of a retrotransposon in the affected child's genome present at a position on the chromosome corresponding to an intron of MFSD8/CLN7 (FIG. 1, FIG. 2). Whole genome sequencing (WGS) was carried out using the following oligonucleotides. Point mutations detected via WGS were confirmed by PCR amplification and Sanger sequencing. The SVA transposon insertion was confirmed by PCR amplification and a series of primer walking experiments. Primer sequences are provided in the table below.

TABLE 1

| Primer name | Sequence |
| --- | --- |
| TY701-MFSD8-intron6-F1 | CGGTAGGTGCAATATTTTAGTCC |
| TY702-MFSD8-intron6-R1 | ACTGCTGGATAAAGCACTCTAAA |
| TY703-MFSD8-intron6-F2 | GCCTGAAAAGCTTCGATGAC |
| TY704-MFSD8-intron6-R2 | TGGCAAAAACTCAATTGGAA |
| TY706-MFSD8-intron6-SVAC2-R12 | CACCGCCCTTAATCCATTT |
| TY708-MFSD8-intron6-SVAC2-F11 | AAGGCAGCATGCTCGTTAAG |
| TY711-MFSD8-intron6-Ghr20-R13 | TCAACATCCATTCTTGACCA |
| TY712-MFSD8-intron6-Chr20-F13 | CAATTTTGGTCAAGAATGGATG |
| TY719-MFSD8-intron6-5'-F5 | TTCCAATAATAAGCCCTCAACAA |
| TY720-MRSD8-intron6-5'-F6 | CCAGTCTACCCTCAGTATCTAGCA |
| TY721-MFSD8-intron6-5'-F7 | CATGAGGACATGGTTTGAGTCT |
| TY725-MFSD8-Tra-SVAR-R-31 | GCCTCCACACCACTGAGC |
| TY727-708 MUTATION-F | AGGGCAGCATGCTCGTTGAG |
| TY728-MFSD8-intron6-Chr20-R | ACCAGTTTAATAAAAGAAACAAGAATG |
| TY729-MFSD8-Exon6-F1 | TGCTGGTGCTACTTCCCTTC |
| TY730-MFSD8-Exon5-F2 | AACAAGTTCCATGGCAAACA |
| TY731-MFSD8-Exon7-R1 | TCACATCCCATGTCACACCT |
| TY732-MFSD8-trans-SVAE-R | TATCCACACAGACCCAGCAA |
| TY 735-Seq-Transpo-727-R | GGAGGGAAGGTCAGCAGATA |
| TY 736-Seq-Transpo-732-F | GGCGGTTTTGTGGAATAGAA |

Figure 5A:
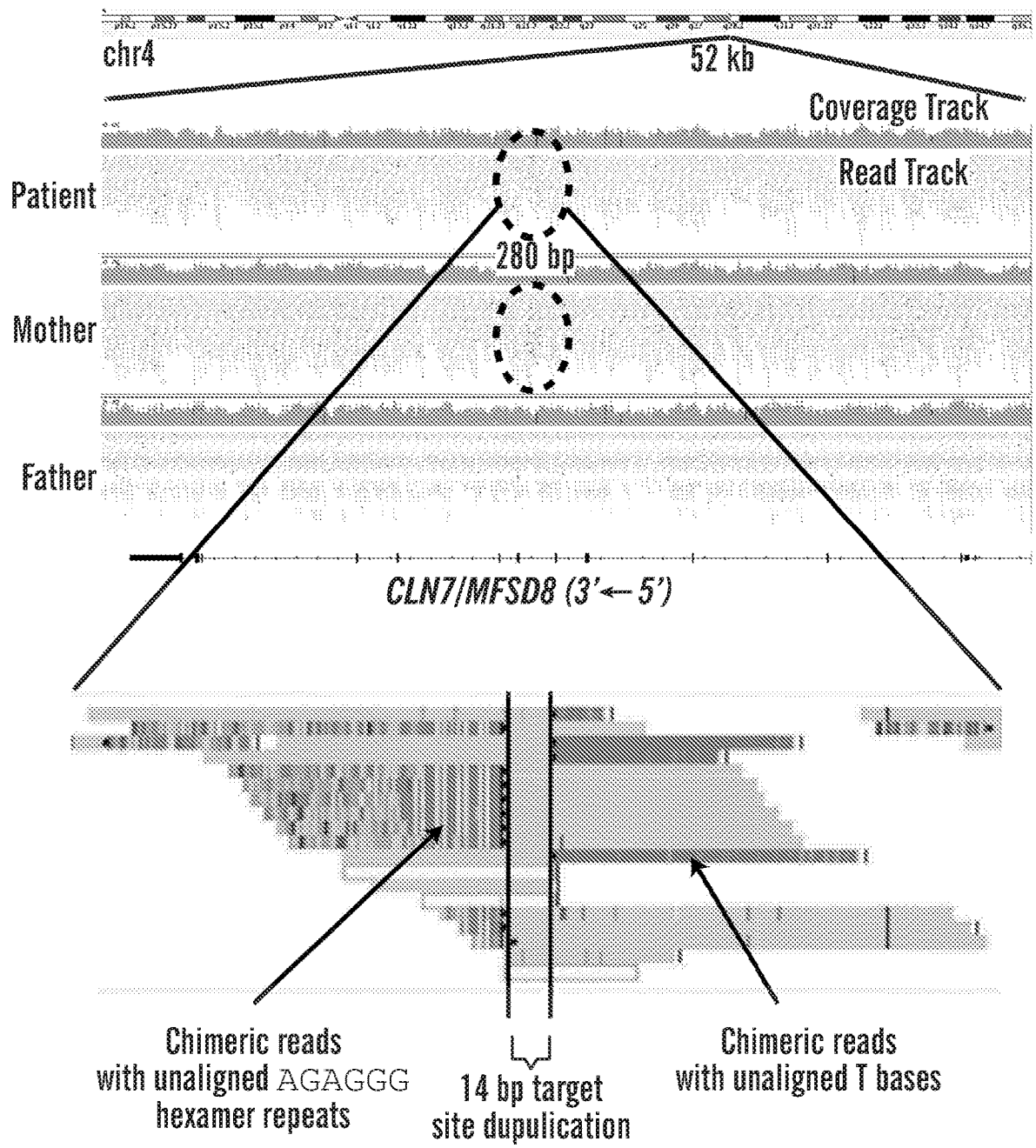
FIG. 5A is a schematic diagram showing a comparative examination of WGS read alignments reveals a cluster of chimeric reads in the subject and mother, which is characteristic of retrotransposon insertion. Integrative Genomics Viewer (IGV) image showing WGS read alignments in the ~52 kb region of chromosome 4 with CLN7/MSD8 gene (top panel). Blow-up image of the ~280 bp region (bottom panel), where two groups of chimeric reads were found: one group with a stretch of T bases on one end, another group with hexameric repeats on the other end. The two groups of chimeric reads shared a common 14 bp region that aligns well to the reference genome; this region corresponds to the duplicated retrotransposon target/entry site, often called "target site duplication."
Figure 5B:
FIG. 5B is a schematic of chimeric sequence reads showing CLN7 intron 6 fused to polyT sequences.
Figure 5C:
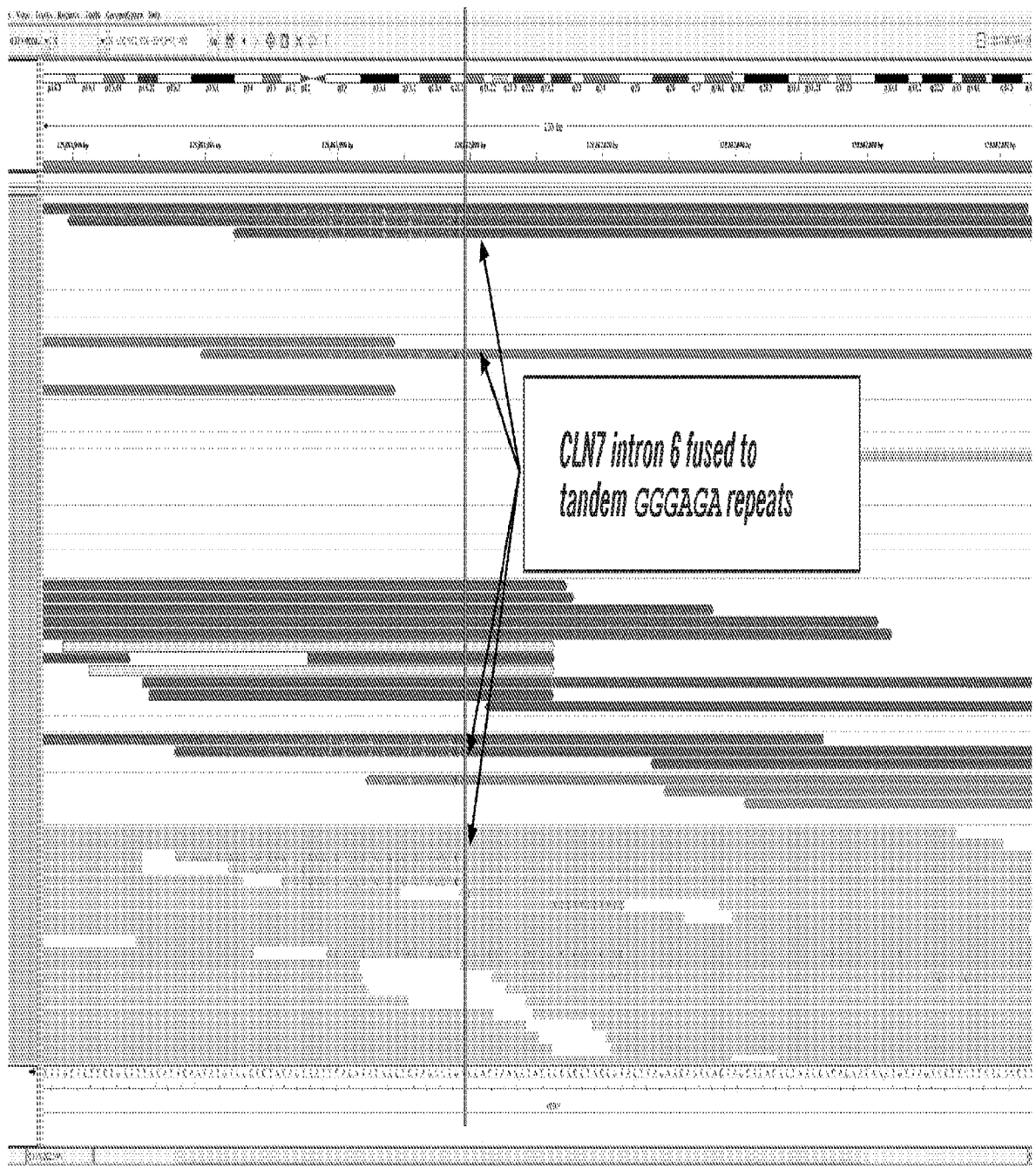
FIG. 5C is a schematic of chimeric sequence reads showing CLN7 intron 6 fused to tandem GGGAGA repeats.
Figure 5D:
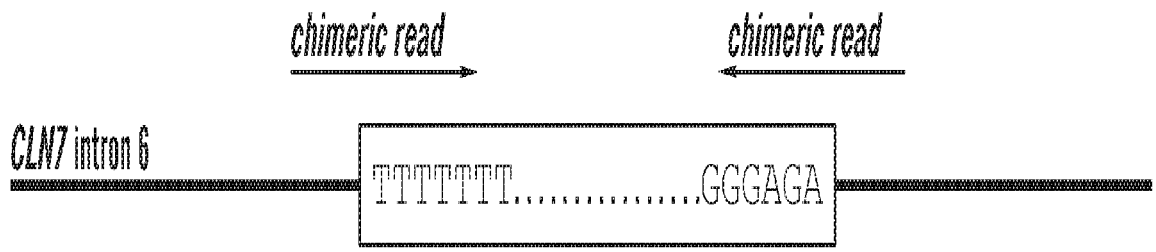
FIG. 5D is a schematic depicting identification of the insertion of the SVA transposon in CLN7 intron 6 of the patient.
Figure 5E:
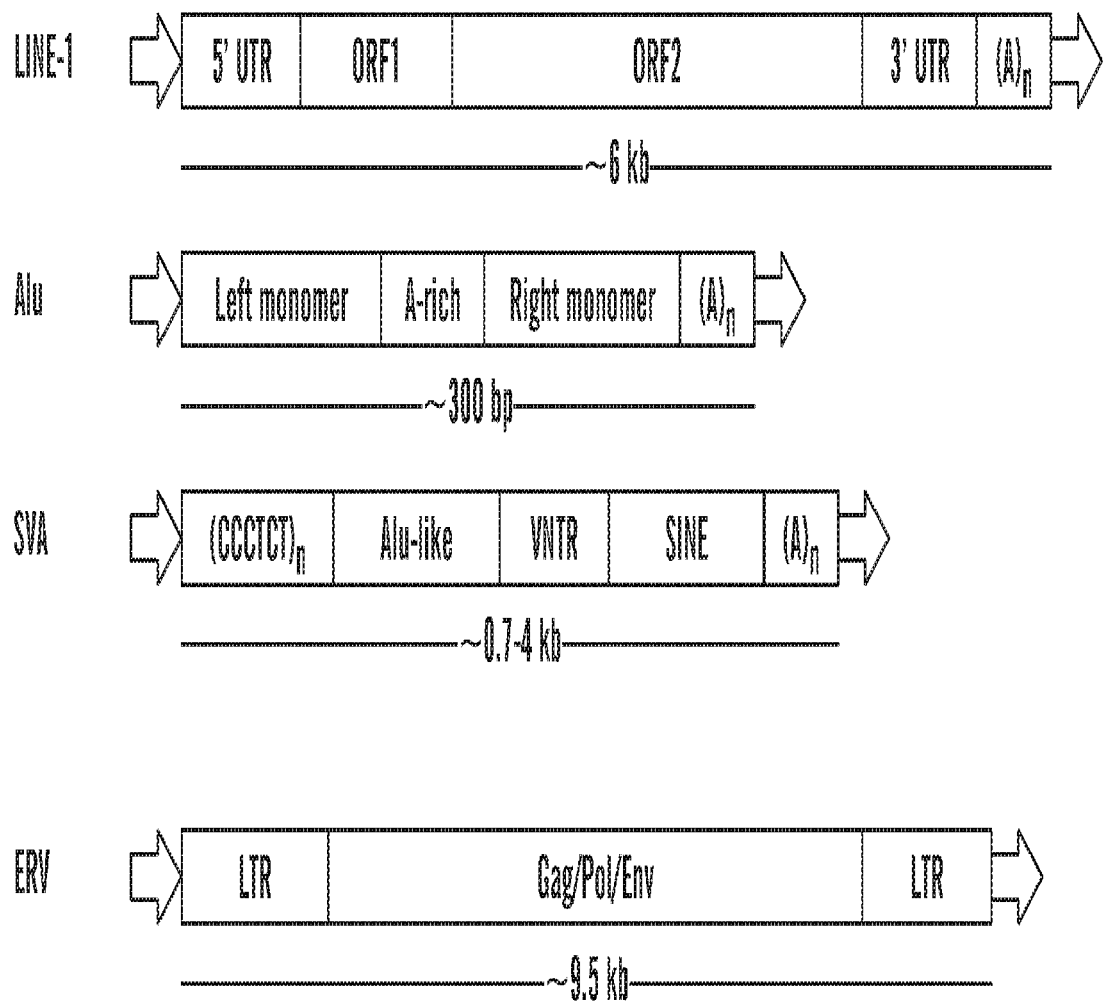
FIG. 5E provides schematic diagrams of transposons.
Figure 5F:
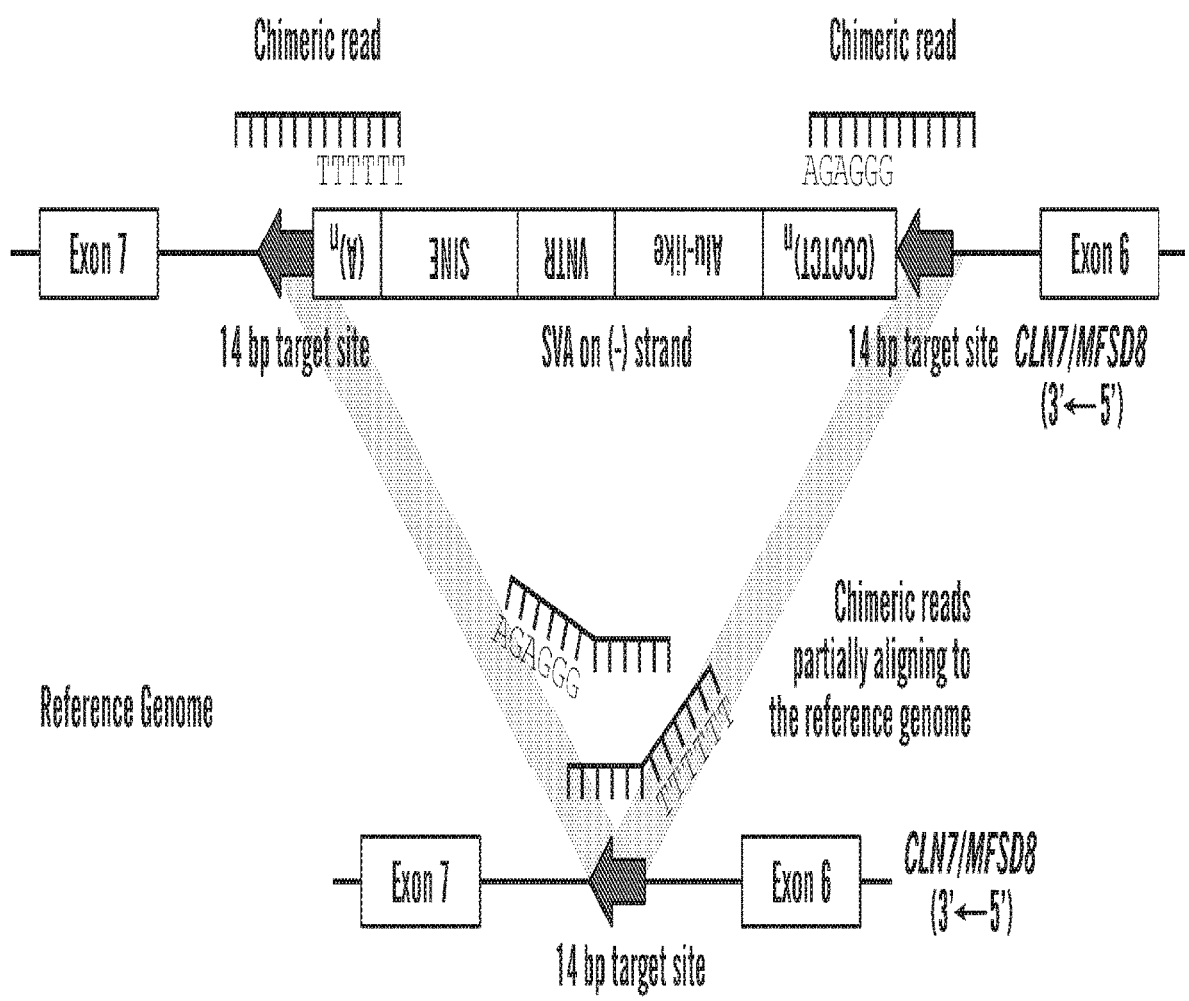
FIG. 5F provides a schematic illustrating how chimeric reads derived from the subject would align on the reference genome. As the SVA transposon is inserted in the minus strand of the subject's genome (i.e. the sense strand of CLN7/MSD8), WGS reads from the boundaries of the insertion will only partially align to the reference genome with the "soft-clipped" overhang of either polyT or hexameric repeat sequences.

WGS unexpectedly revealed a maternally inherited retrotransposon insertion into intron 6 of the subject's CLN7/MFSD8 gene. When WGS reads from the subject were aligned to the reference genome and visualized in Integrative Genomics Viewer (IGV), the insertion manifested as a cluster of "chimeric reads" that aligned only partially to the reference genome, because they spanned the boundaries of the reference sequence and the foreign sequence (FIG. 5A, top). The chimeric read cluster was detected in the subject and her mother, but not her father, indicating maternal inheritance of the insertion. Inspection of the chimeric read alignments showed that they either had unmapped (a.k.a. "soft-clipped") polyT sequences on one end or unmapped hexameric repeat sequences (AGAGGG) on the other end, indicating that the insertion contained these motifs at the boundaries (FIG. 5A, bottom). In addition, the chimeric read breakpoints flanked a 14 bp sequence that aligns well to all chimeric reads, suggesting that this 14 bp endogenous sequence was duplicated and is present in both boundaries of the insertion. These features (polyT stretch, hexameric repeats, and retrotransposon target site duplication) were consistent with the insertion of SVA family retrotransposon into the minus strand of the reference genome, the sense strand of CLN7/MFSD8 (FIGS. 5E and 5F).

Figure 5G:
FIG. 5G is a diagram showing the results of Sanger sequencing and CLIA-based genome analyses, which confirm the SVA retrotransposon insertion in the subject and mother's genome. The insertion was not observed in the father and brother's genomes. The location, length, and context of the SVA insertion in the subject and mother's CLN7/MFSD8 allele are displayed in the sense direction (minus strand of the reference genome). Also shown are the locations of Sanger sequencing primers used to sequence and assemble the full retrotransposon consensus sequence.
Figure 5G:
Figure 5G:
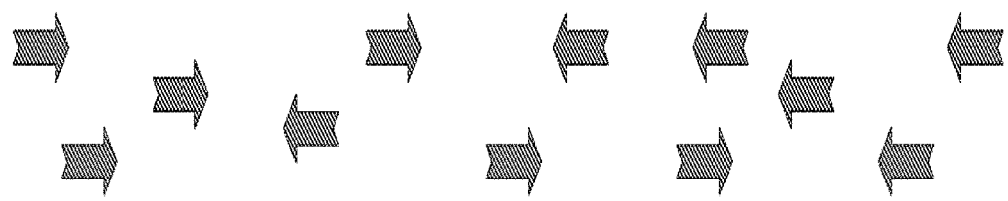
Figure 5H:
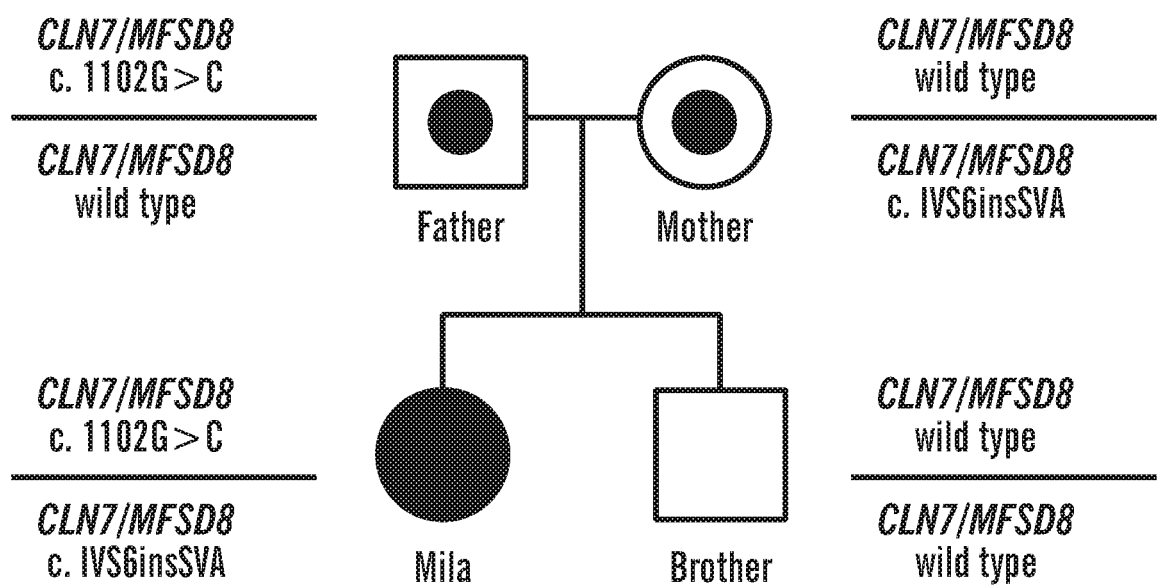
FIG. 5H is a diagram showing the CLN7/MFSD8 mutation status of the four members of the subject's family, which was confirmed by CLIA-based genome analysis.

PCR amplification and Sanger sequencing using a primer walking approach was employed to sequence across the breakpoints, revealing a ~2 kb insertion in both the subject and in her mother (FIG. 5G). RepeatMasker analysis confirmed that the sequenced insertion was indeed a SVA retrotransposon. The presence of this SVA was also confirmed on a CLIA basis both in the subject and in her mother by Claritas Genomics. CLIA analysis also confirmed absence of the SVA insertion in the subject's father, and also demonstrated that the subject's brother bore neither the SVA insertion nor the paternal missense mutation (CLN7/MFSD8 c.1102G>C) (FIG. 5G, 5H). The segregation pattern of the SVA insertion is therefore consistent with it being the pathogenic cause (in combination with c.1102G>C) of neurodegeneration in the subject. SVA retrotransposons are the youngest and most active family of retrotransposons in the human genome. They are specific to hominids, and are present in ~2700 copies per genome (representing ~0.2% of the human genome). There have been thirteen documented cases of SVA insertions causing Mendelian disease in human by interrupting a human disease-associated gene. the subject's SVA insertion into CLN7/MFSD8 has never been reported.

Figure 5I:
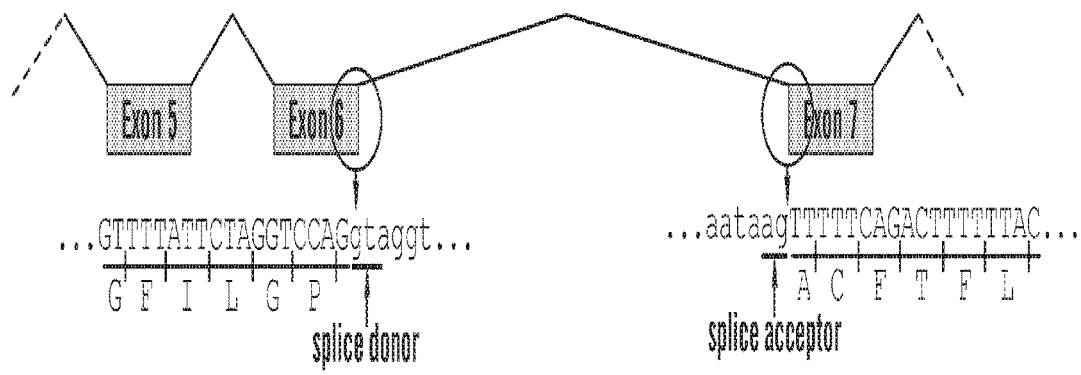
FIG. 5I depicts results of RNA-seq and RT-PCR analyses, which showed that the SVA retrotransposon insertion causes exon trapping and resulting premature translational termination. Exon trapping and premature translational termination of CLN7/MFSD8 by the SVA retrotransposon insertion, was revealed by the blood RNA-seq analysis of the subject's four family members.
Figure 5I:
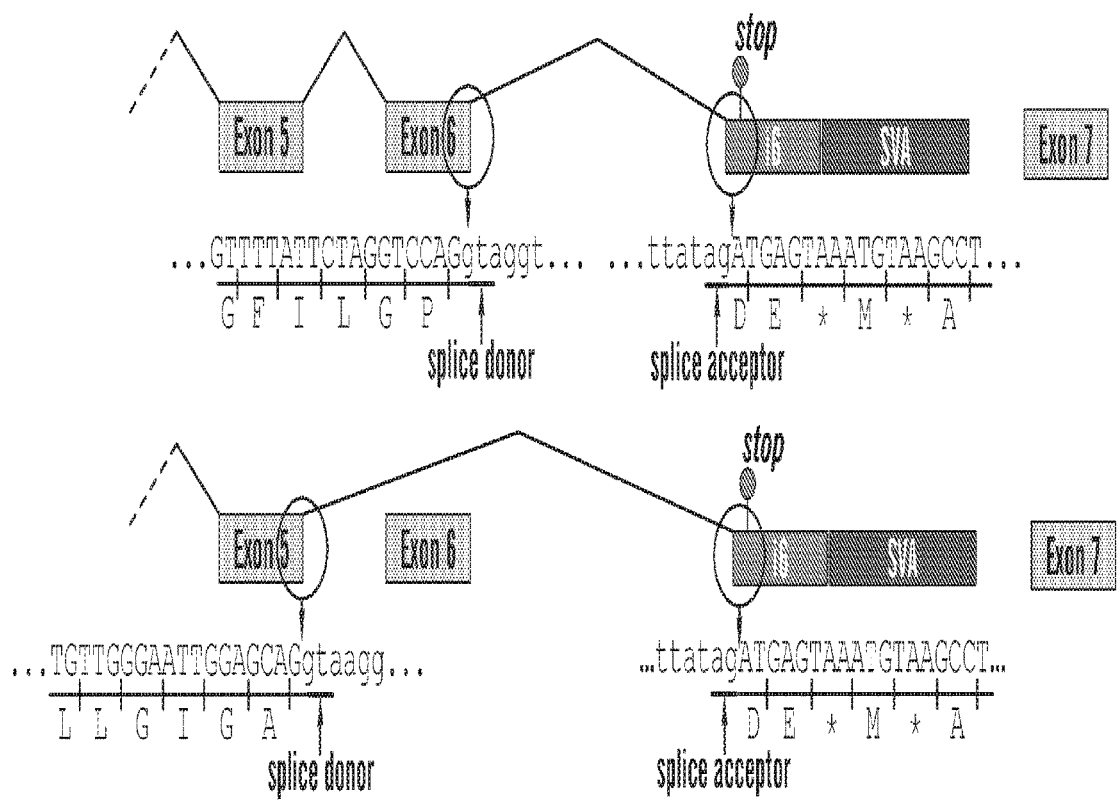
Figure 5J:
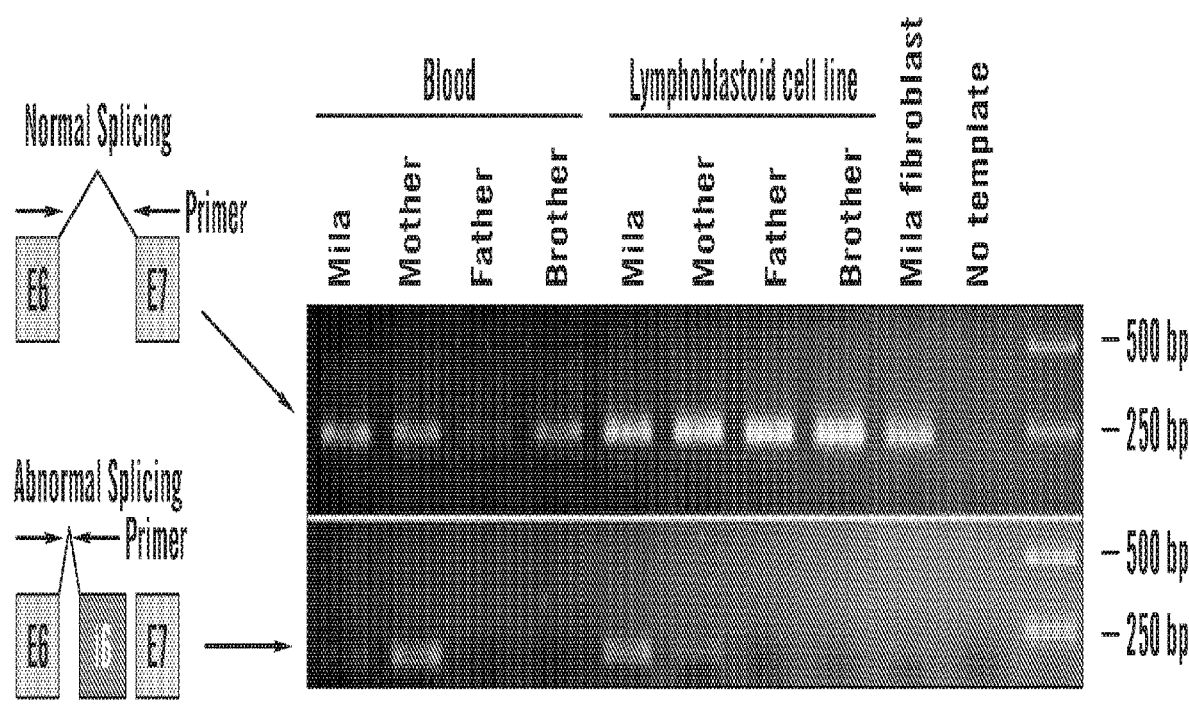
FIG. 5J shows RT-PCR confirmation of the exon trapping by SVA retrotransposon in the subject and mother.

SVA retrotransposons are known to encode strong splice enhancer sequences that modulate patterns of splicing of nearby genes, sometimes resulting in exon trapping (Hancks et al, Genome Research 2009). To understand whether this may be occurring with the subject's SVA retrotransposon, splicing patterns were examined using RNA-seq analysis. Splice junction analysis of >126 million read pairs, using polyA+ RNA isolated from the subject's whole blood, revealed that SVA retrotransposon insertion into intron 6 activates a cryptic splice site ("i6.SA") 133 basepairs upstream of the insertion site (FIG. 5I). Splicing from exon 6 into i6.SA was detected in RNA isolated from the subject as well as from her mother, but neither her father nor her brother (who do not carry the SVA insertion). These results were confirmed with RT-PCR from patient fibroblasts and from whole blood and lymphoblasts from all four family members (FIG. 5J). Abnormal splicing into i6. SA results in an immediate stop codon and truncation of the CLN7/MFSD8 protein product (p.184PhefsX3).

The retrotransposon insertion was discovered by chimeric reads with intron 6 sequences fused to polyT and tandem GGGAGA repeats, respectively (FIGS. 5A-5D). This retrotransposon insertion generated a stop codon in the intron following exon six, resulting in MFSD8 gene truncation and loss of protein function (FIG. 2). In essence, the transposon insertion was acting as an exon trap. Exon trapping is a molecular biology technique used to identify the presence of exons in a fragment of DNA. In exon trapping a genomic fragment of unknown intron/exon structure is inserted into the intron of a splicing vector consisting of a known exon-intron-exon sequence of DNA. If the fragment does not contain exons (i.e., consists solely of intron DNA), it will be spliced out together with the vector's original intron. On the other hand, if exons are contained, the exons will be part of the mature mRNA after transcription (with all intron material removed). The presence of 'trapped exons' can be detected by an increase in size of the mRNA.

Figure 3:
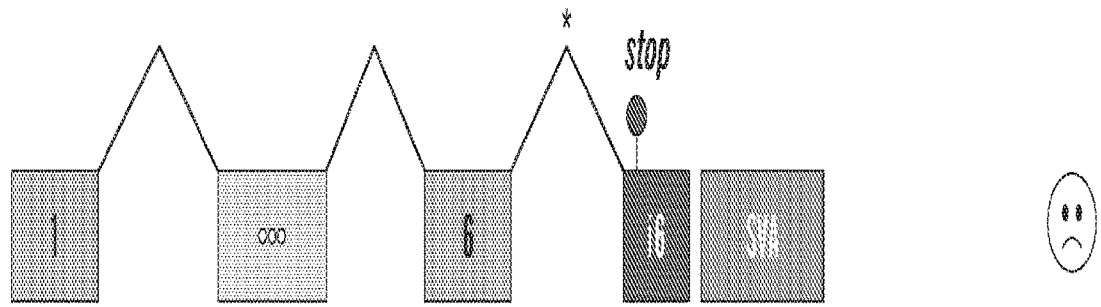
FIG. 3 is a schematic diagram showing the strategy for use of an exon skipping drug to block a splice acceptor site and restore normal gene splicing.
Figure 3:
Figure 3:
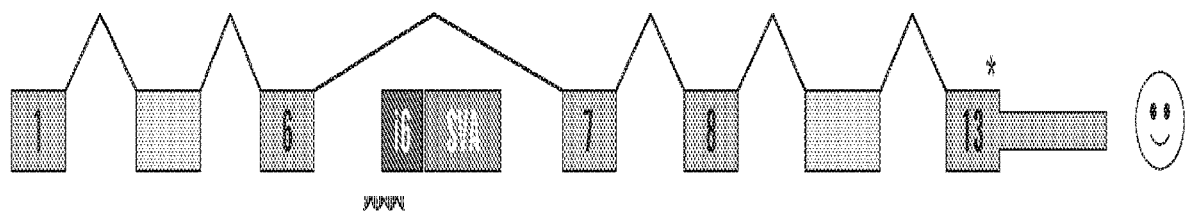
Figure 4:
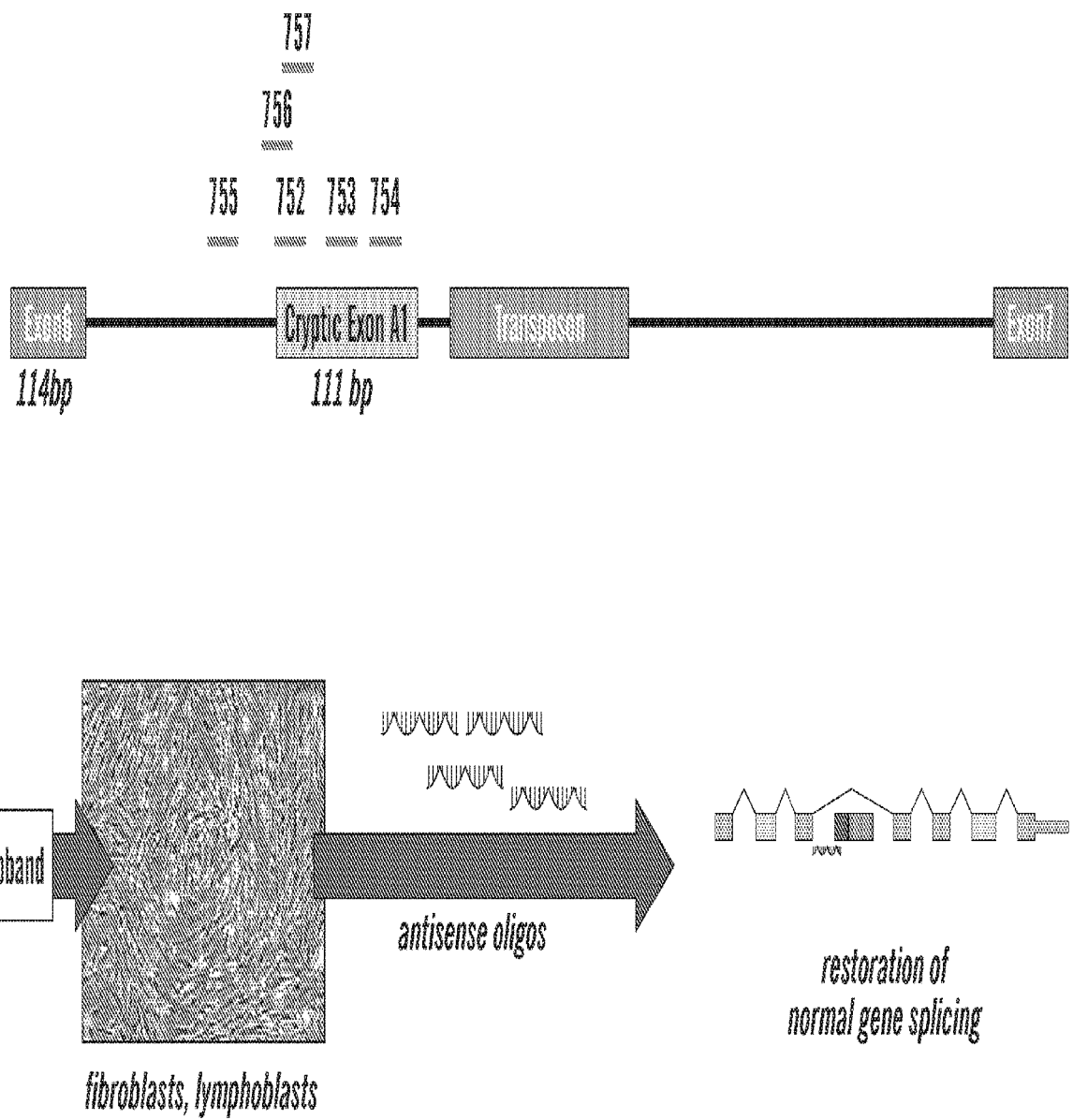
FIG. 4 is a schematic diagram showing the strategy for use of antisense oligonucleotides to restore normal gene splicing in the proband's MFSD8 gene.

The genetic disorder present in the affected child could be ameliorated if the stop codon produced by the intron could be skipped allowing restoration of the normal reading frame (FIG. 3, FIG. 4).

Exon skipping, or splice modulation in general, can be treated by antisense oligonucleotide therapy. Exon skipping is achieved using antisense oligonucleotides, which have the ability to hybridize to a sense target sequence, modulating splicing patterns of the target molecule. Antisense-mediated exon skipping has been shown to be useful for the restoration of a normal reading frame in genes impaired by mutations that alter undesirable gene splicing. This approach can be effective when the skipped exon is not critical for protein function, or when a non-productive exon is brought into play by a patient mutation. Exon skipping has been used to treat Duchenne's Muscular Dystrophy, where partial protein function is maintained despite the absence of the skipped exons, as well as spinal muscular atrophy, where full protein function is restored by restoring normal splicing patterns to a functionally substitutable pseudogene.

To determine whether steric blockade via an antisense oligonucleotide could be utilized to rescue CLN7/MFSD8 exon trapping induced by subject's SVA, a series of antisense oligonucleotides, complementary to the i6.SA cryptic splice acceptor site and nearby computationally predicted splice enhancers (RESCUE-ESE (Fairbrother et al., 2004) and ESEfinder (Smith et al., 2006) (FIG. 6A) were designed and synthesized.

Antisense oligonucleotides were generated to target the splice acceptor site and predicted splice enhancer sequences flanking it. Exemplary antisense oligonucleotides that were generated and tested are shown at the following Table 2A.

TABLE 2A

| Antisense Oligonucleotides Targeting Splice Enhancer Sequences | |
|---|---|
| Name | Sequence |
| TY790 (TY777A) | TTAGTGCTTGTTGAGGGC |
| TY791 (TY777B) | GTTAGTGCTTGTTGAGGG |
| TY792 (TY777C) | TGTTAGTGCTTGTTGAGG |
| TY793 (TY777D) | ATGTTAGTGCTTGTTGAG |
| TY777-MFSD8ASO-2MOE | AATGTTAGTGCTTGTTGAGGGC |

Additional sequences of the antisense oligonucleotides used in these studies, designed to be complementary to computationally predicted splice enhancers surrounding the i6.SA splice site, are shown in following Table 2B (SEQ ID NOS: 2578-2585, respectively, in order of appearance).

Milasen/TY777 was investigated using (1) qRT-PCR experiments to study dose-response relationships and (2) RNA-seq to confirm its splice correction effect. First, when electroporated into patient fibroblasts at a range of doses (0, 1, 10, 20, 50, 100, 200, 500 nM), milasen/TY777 demon-

| ASO name | Sequence | Modifications | Manufacturer |
|---|---|---|---|
| TY765-MFSD8-ASO-1 | AGCUUUUCAGGCUUACAUUUACUCAUCU | PS 2'-OMe | IDT |
| TY766-MFSD8-ASO | AAUGUUAGUGCUUGUUGAGGGC | PS 2'-OMe | IDT |
| TY767-5MFSD8-ASO- | CUAGCAUACAGUAAGCACACA | PS 2'-OMe | IDT |
| TY768-MFSD8-ASO- | CUUUAAAAUGCUUUUAAGGUGGUA | PS 2'-OMe | IDT |
| TY769-MFSD8-ASO-1A | CAGGCUUACAUUUACUCAUCU | PS 2'-OMe | IDT |
| TY770-MFSD8-ASO-1B | GUCAUCGAAGCUUUUCAGG | PS 2'-OMe | IDT |
| TY777-MFSD8ASO-2MOE | AAUGUUAGUGCUUGUUGAGGGC | PS 2'-OMe, 5Me-C, 5Me-U | IDT |
| TY772_22 nt | CGCGACTATACGCGCAATATGC | PS 2'-OMe | IDT |

Fibroblasts of the patient were isolated and cultured to study lysosomal activity and function. Fibroblasts and LCL were transiently transfected with ASOs using Lipofectamine™ 3000 (ThermoFisher) according to the manufacturer's instructions. ASOs were used at 100 nM. Transfected cells were harvested at 24 hours. For dose-response experiments, fibroblasts were transfected by electroporation (Neon Transfection System, ThermoFisher) according to the manufacturer's instructions. ASO were used at concentrations ranging from 1-1000 nM as indicated.

Figure 6A:
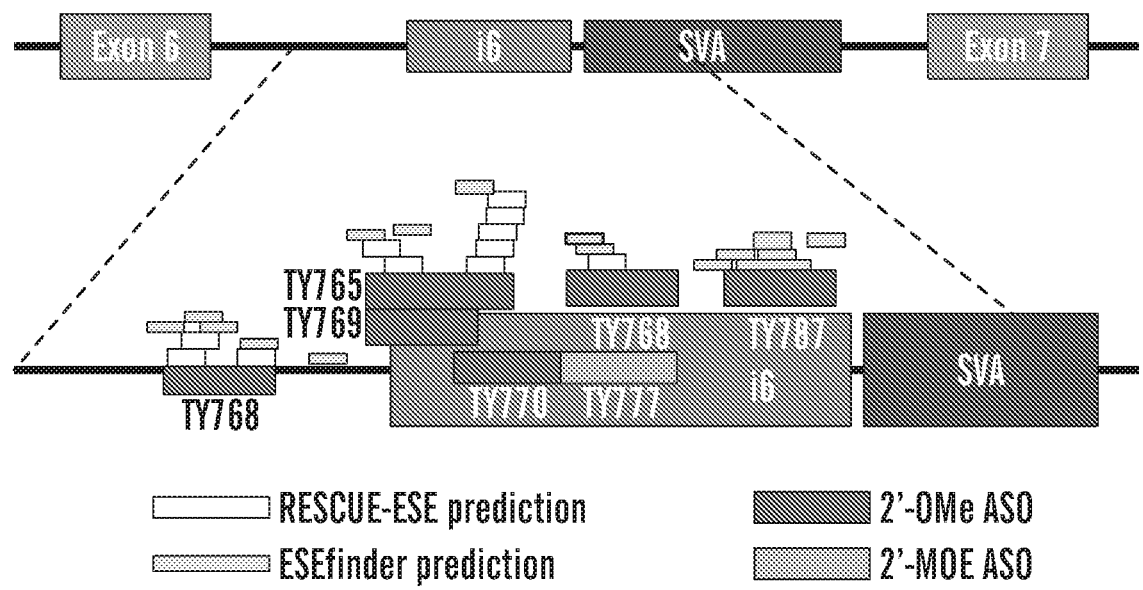
FIG. 6A-6C shows that antisense oligonucleotide screening identified TY777, which effectively rescues exon trapping.
Figure 6B:
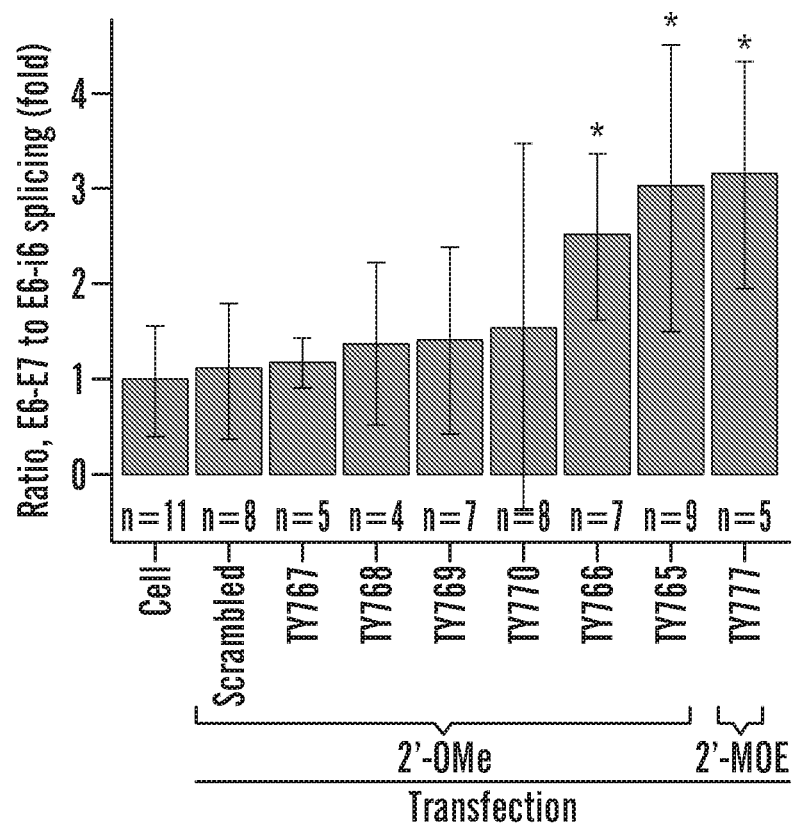
Figure 6C:
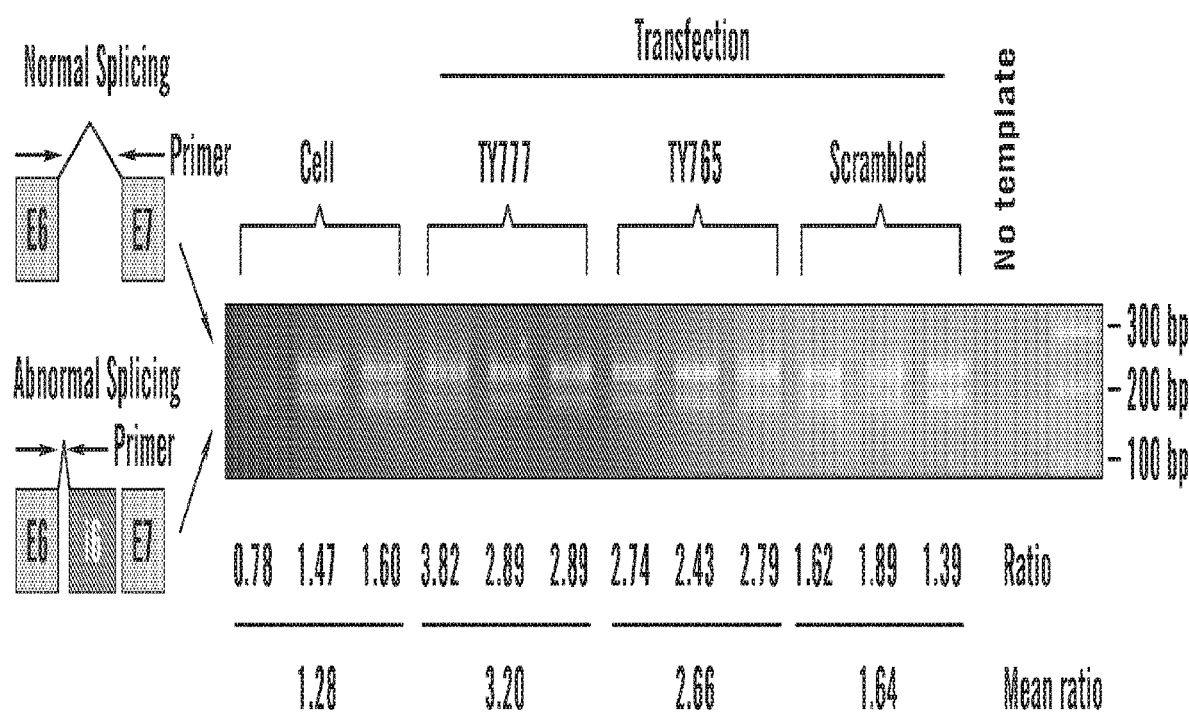
Figure 7:
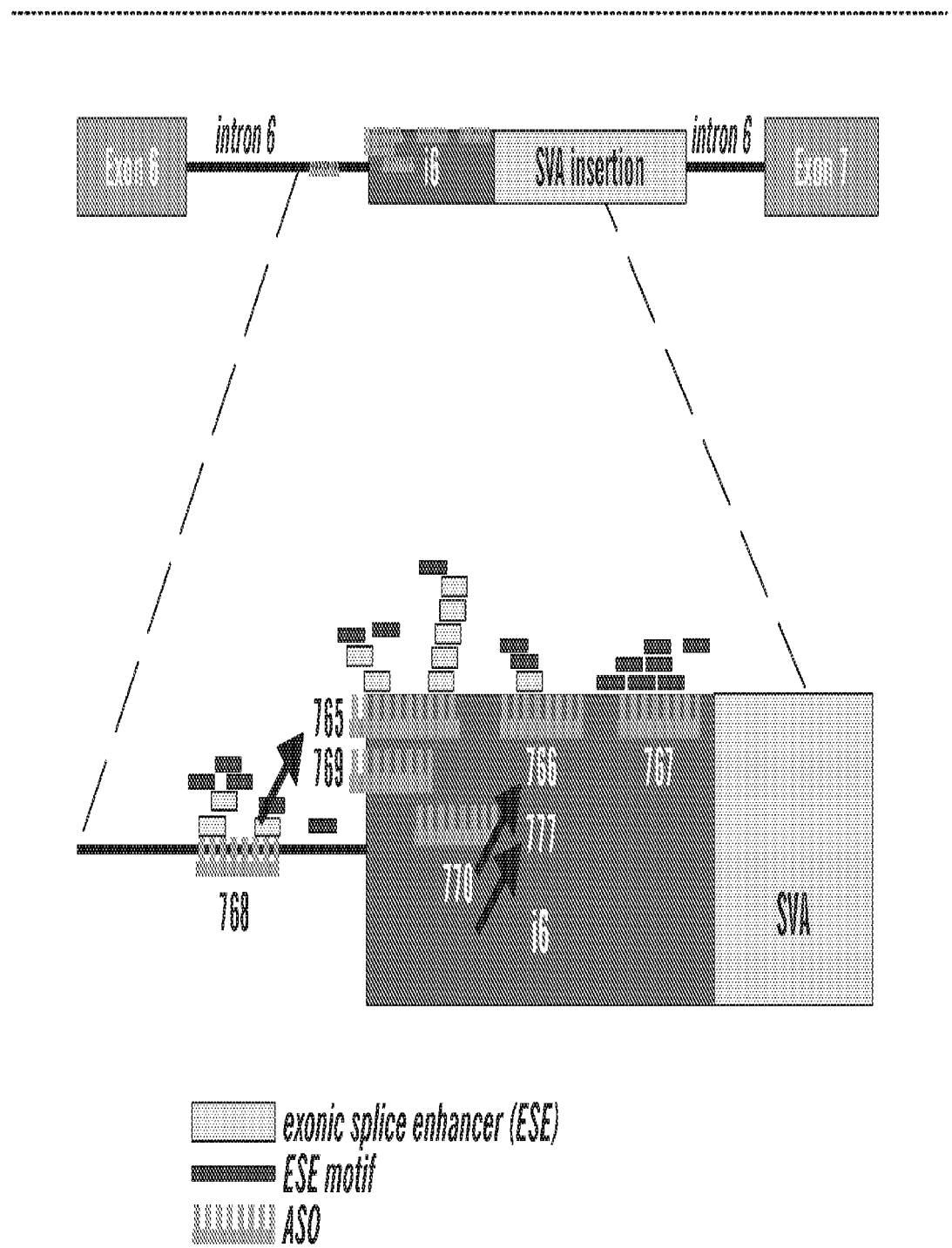
FIG. 7 is a schematic showing the locations where antisense oligonucleotides target the splice acceptor and a downstream site.

After 24 hours, RNA was isolated, and RT-PCR was utilized to assess levels of normal exon 6 to exon 7 vs. abnormal mutant splice product (FIG. 6A). In untransfected cells or cells transfected with a scrambled oligonucleotide control (TY772), the ratio of normal to mutant splice forms ranged around 1:1 (FIGS. 6B and C). An initial screen was conducted using fully phosphorothioated, 2'-OMe-modified oligonucleotides. From this initial screen, two candidates, TY765 and TY766, emerged that significantly increased the ratio of normal:mutant splice ratio by 2.5- to 3-fold in patient fibroblasts (FIG. 6B). TY765 is a 28-nucleotide oligonucleotide that is complementary to a cluster of predicted splice enhancer motifs directly overlying the i6. SA splice acceptor site, while TY766 is a 22-nucleotide oligonucleotide that targets a cluster of predicted splice enhancer motifs 48 bp downstream of the i6.SA site (FIG. 6A). The latter was selected as our lead candidate because its shorter length may help with biodistribution and cellular uptake in vivo. In order to match the chemistry with that of nusinersen—an FDA-approved 18-nucleotide oligonucleotide for spinal muscular atrophy that has shown minimal toxicity—TY777, a fully phosphorothioated, 2'-O-methoxyethyl (PS 2'-MOE) version of the same sequence as TY766 was generated. Similar to TY766, TY777 resulted in 3-fold increase in the ratio of normal to mutant CLN7/MFSD8 splicing (FIGS. 6B, and C).

Figure 8A:
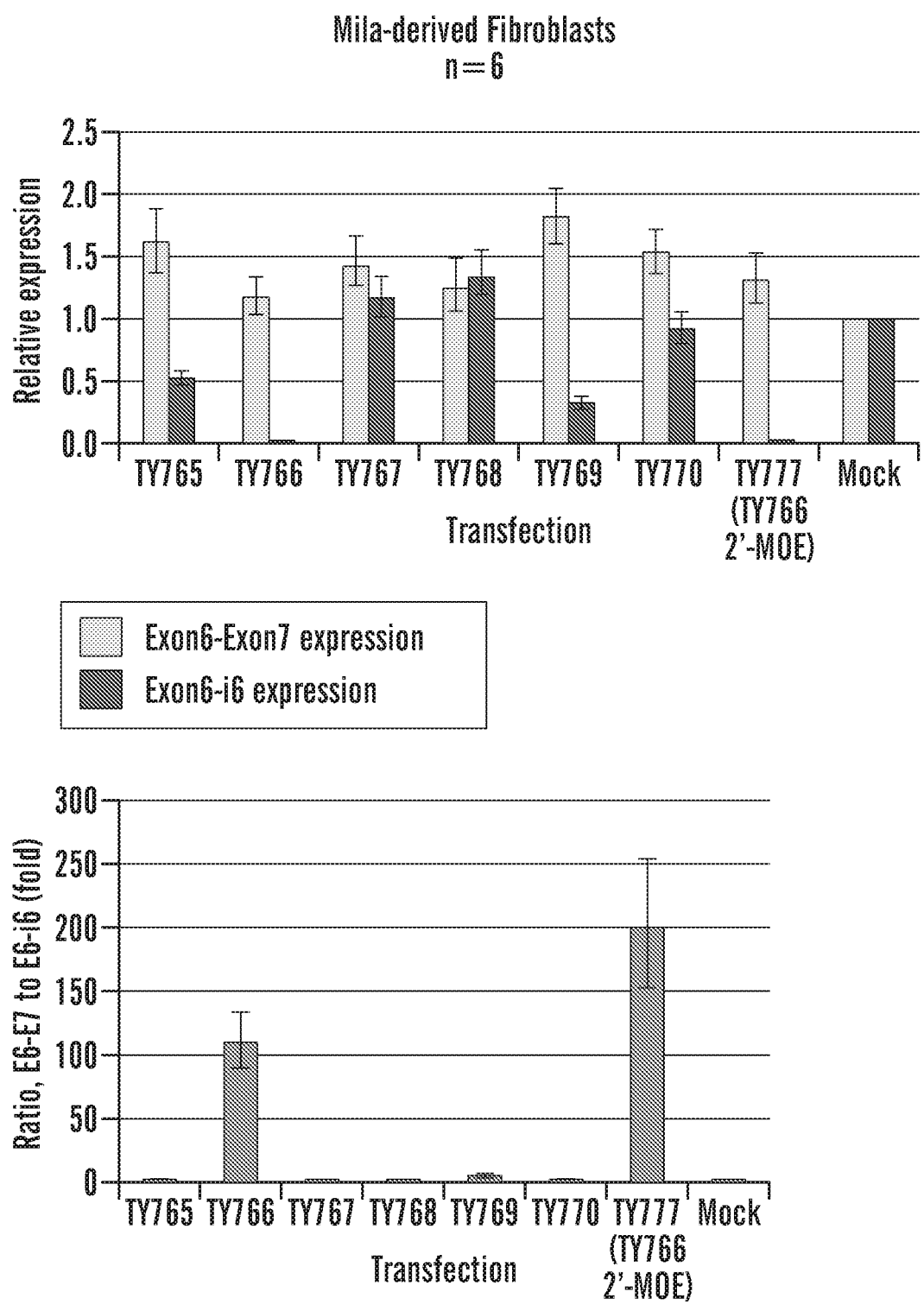
FIGS. 8A and 8B provide graphs depicting the results of a blind experiment conducted by an independent GLP-like laboratory, which confirmed the efficacy of TY777.
Figure 8B:
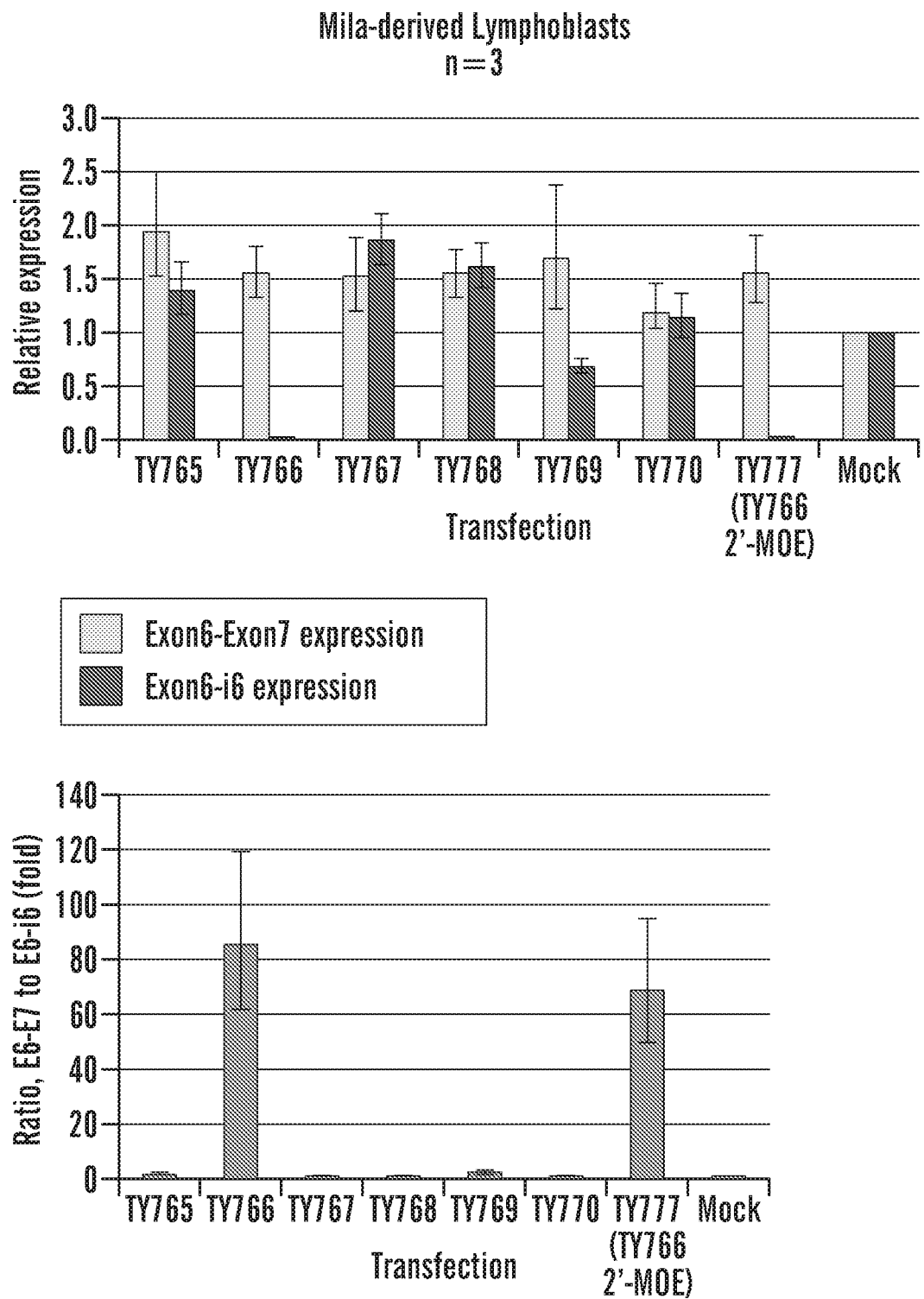
Figure 9:
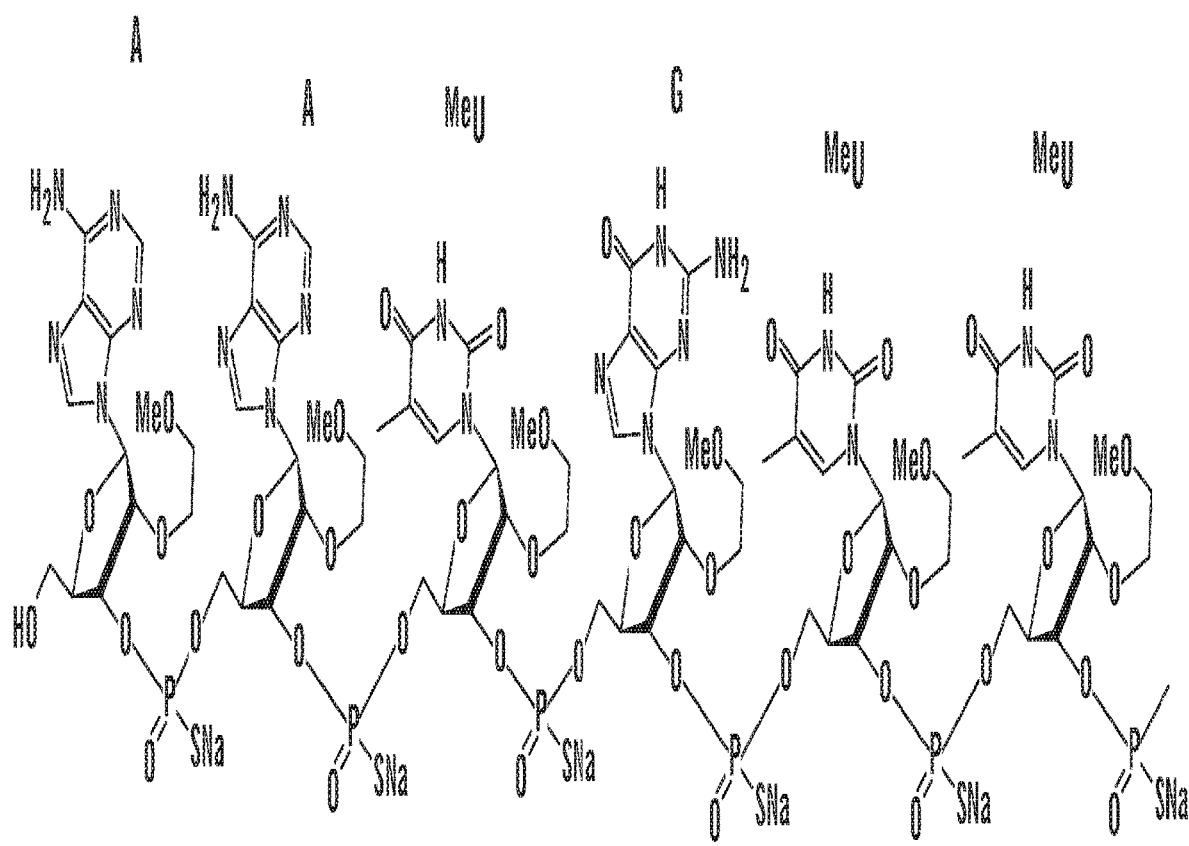
FIG. 9 shows the structural formula of the drug, which is a 22 nucleotide 2'-O-methoxyethyl modified antisense oligonucleotide with complete phosphorothioate backbone (SEQ ID NOS: 2610 and 2610, respectively, in order of appearance).
Figure 9:
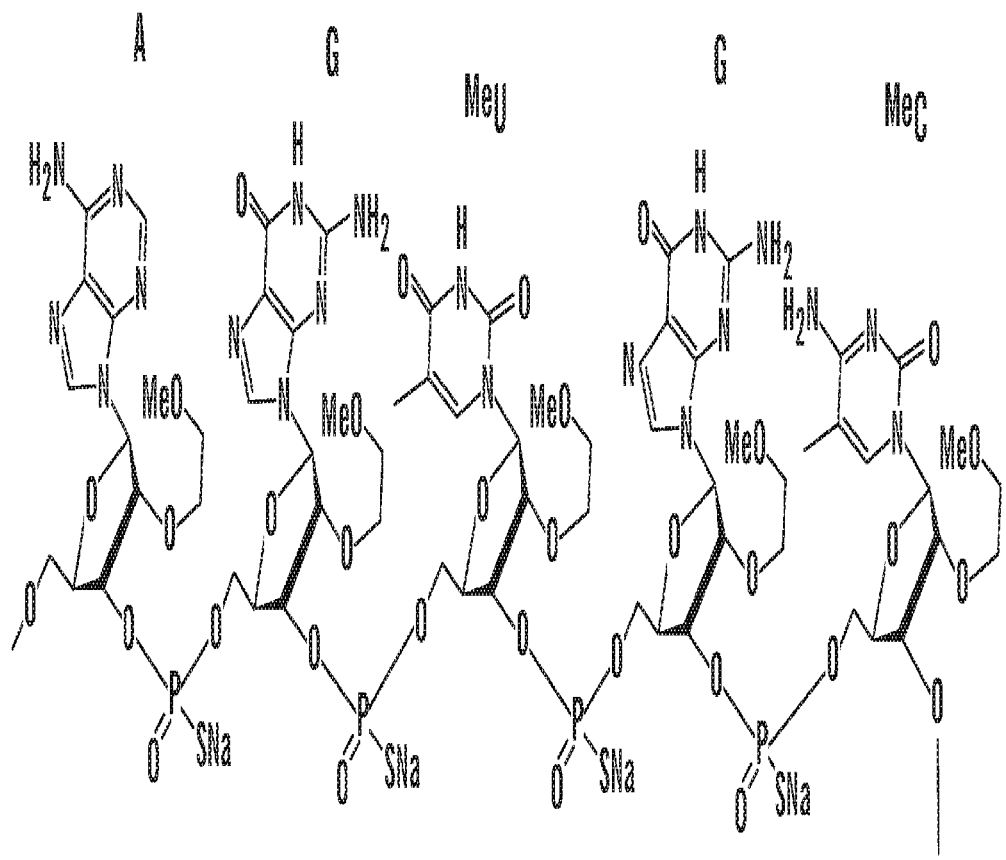
Figure 9:
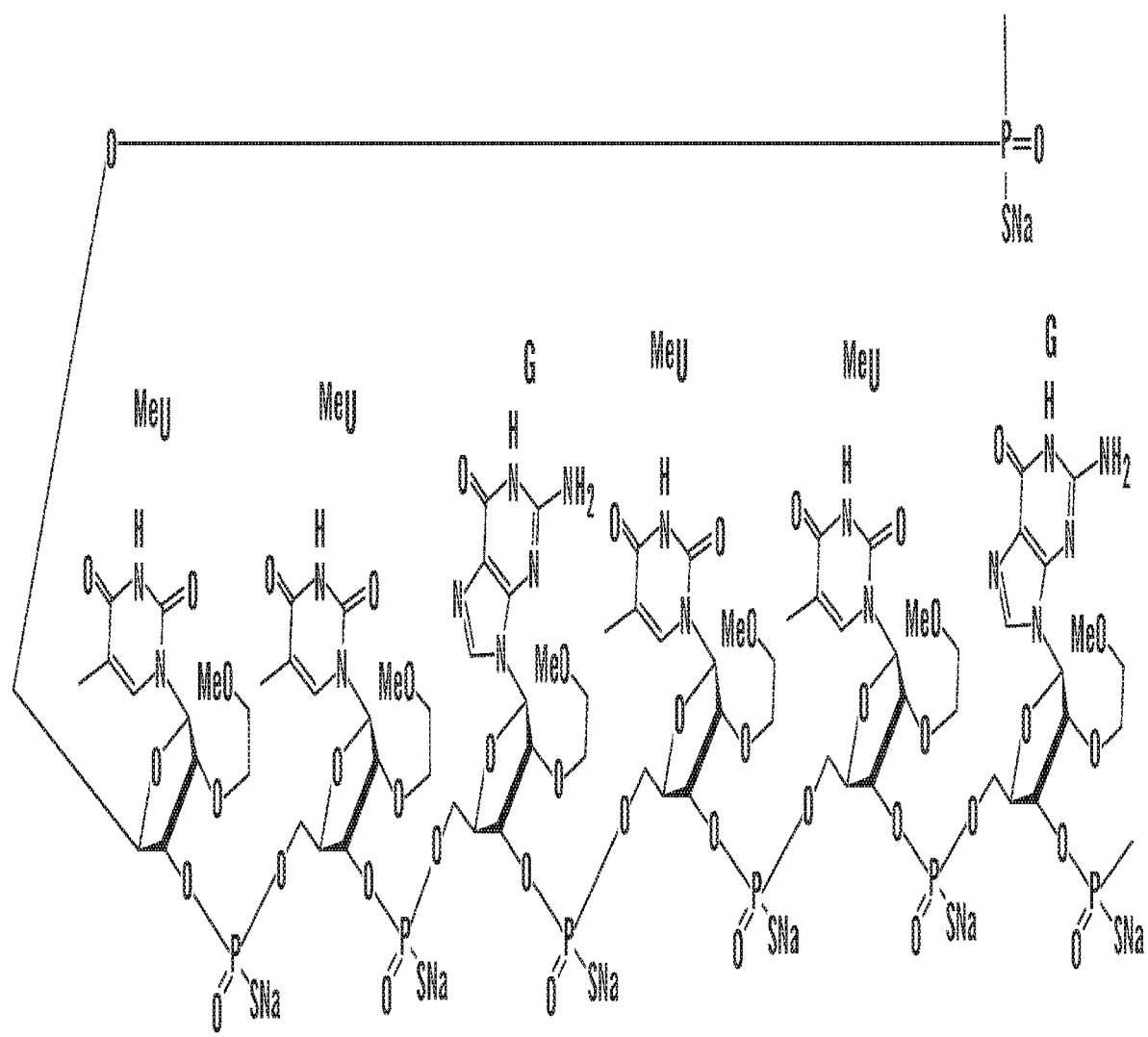
Figure 9:
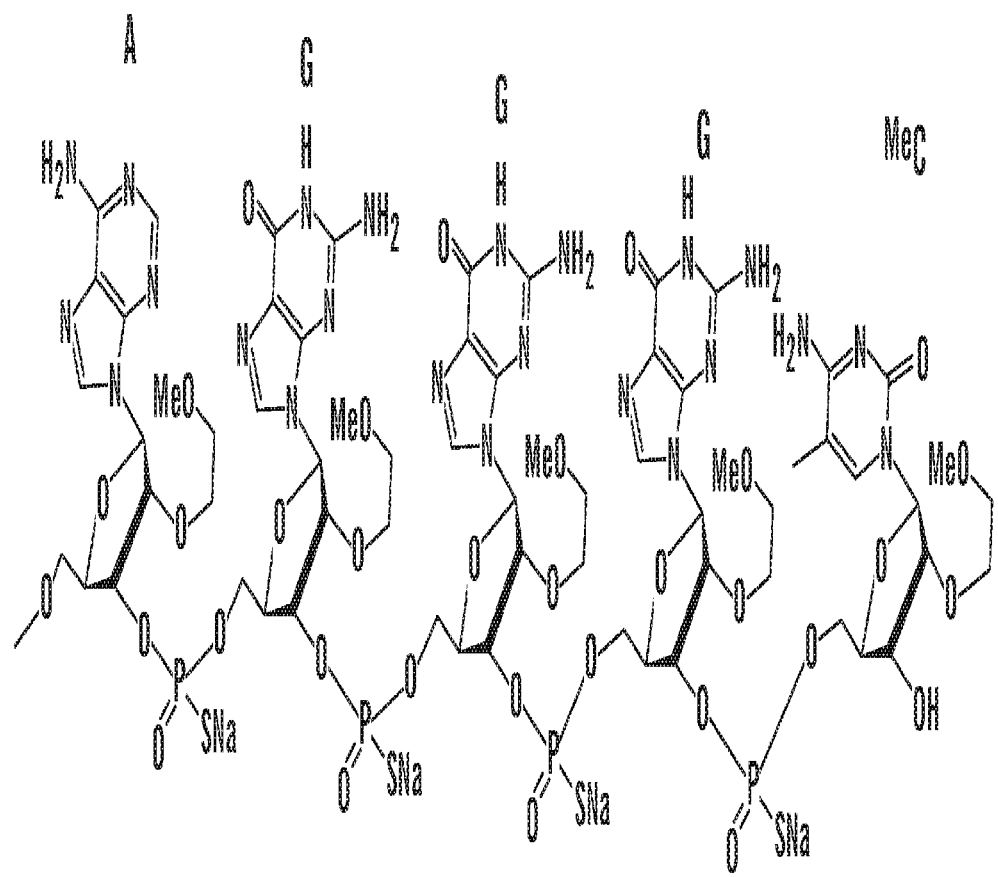
Figure 10:
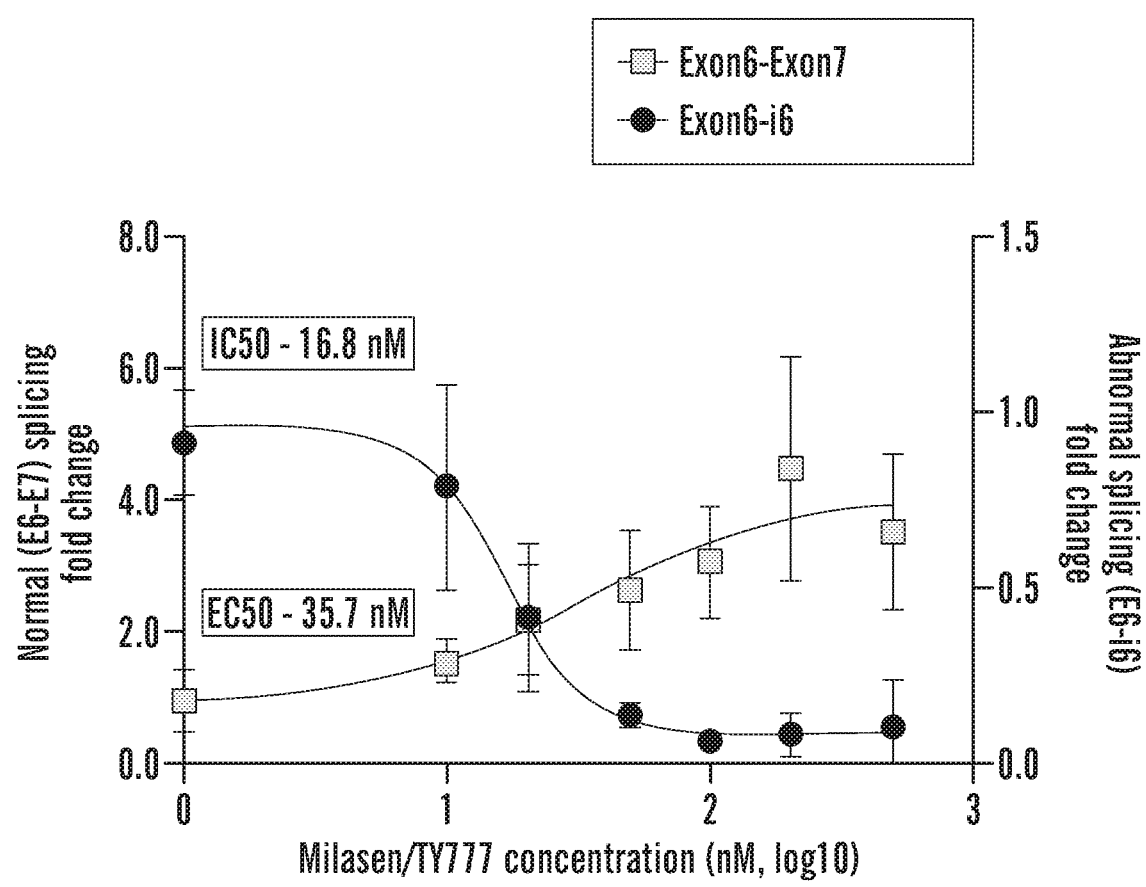
FIG. 10 is a graph depicting results of a quantitative RT-PCR experiments showing milasen/TY777 is effective at nanomolar concentration.

To validate these initial findings, patient cell lines and oligonucleotide reagents were provided to the BCH TransLab. Their blinded experiments replicated the initial findings, not only in patient fibroblasts, but in patient lymphoblasts as well (FIG. 8A, 8B). Consistent with these results, TY766 and TY777 showed the most consistent and largest magnitude level of splice correction. TY777 became the lead candidate for compassionate use for the patient. It was renamed it milasen/TY777.

strated a half-maximal inhibitory effect (IC50) on abnormal exon 6 to i6.SA splicing at ~17.4 nM, and a half-maximal effective concentration (EC50) of ~36.9 nM in terms of activation of normal exon 6 to exon 7 splicing (FIG. 10). These values are similar to those obtained in early proof of concept studies with antisense oligonucleotides targeting SMN2. These data also indicate that the potency of milacin/TY777 meets previously suggested criterion (EC50 less than 100 nM in a cellular assay) for preclinical antisense oligonucleotide candidates.

Figure 11:
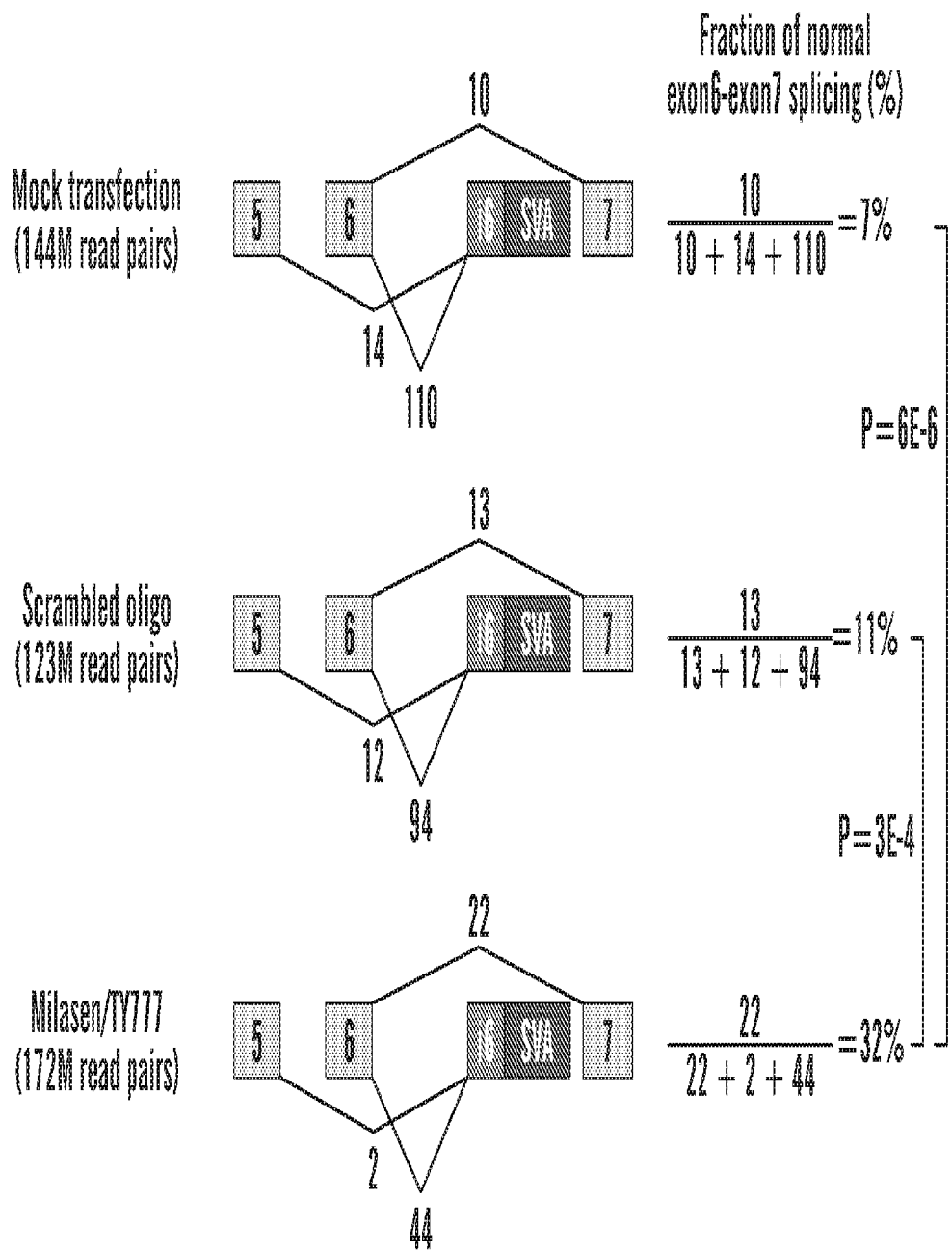
FIG. 11 is a diagram showing that RNA-seq analysis confirms the splice-correcting effect of milasen/TY777. Chi-Square Test of Independence was used for assessing statistical significance.

As additional confirmation, RNA-seq was carried out of polyA+ RNA isolated from untransfected, mock-transfected, and milasen/TY777-transfected patient fibroblasts (FIG. 11). Transfection with milasen/TY777 at 100 nM concentration boosted normal exon 6 to exon 7 splicing to 32% of local splice junctions, compared to 7-11% from mock-transfected patient fibroblasts or those transfected with a scrambled oligonucleotide (p<0.001 for both comparisons, Chi-Square Test) (FIG. 11).

In silico sequence analysis of Milasen/TY777 demonstrated absence of predicted off-target binding sites. Since off-target binding of an oligonucleotide can lead to side effects and toxicity, potential off-target binding sites of milasen/TY777 in the human genome were examined. To simulate binding of end-degraded oligonucleotide products or partial binding of an intact oligonucleotide with a few nucleotide mismatches at either end, BLAST was used to map progressively smaller subsequences of milasen/TY777 to the human reference sequence (GRCh38/hg38; FIG. 12).

Milasen/TY777 did not have any off-target matches to the genome until it is trimmed down by 6 nucleotides (down to a 16-mer), whereas nusinersen, an FDA approved drug with minimal side effect or toxicity, started to have off-target matches when trimmed down by only 1 nucleotide (down to 17mer). This analysis illustrates that milasen/TY777 is likely to have a comparable or smaller off-target binding footprint on the human genome.

Figure 13A:
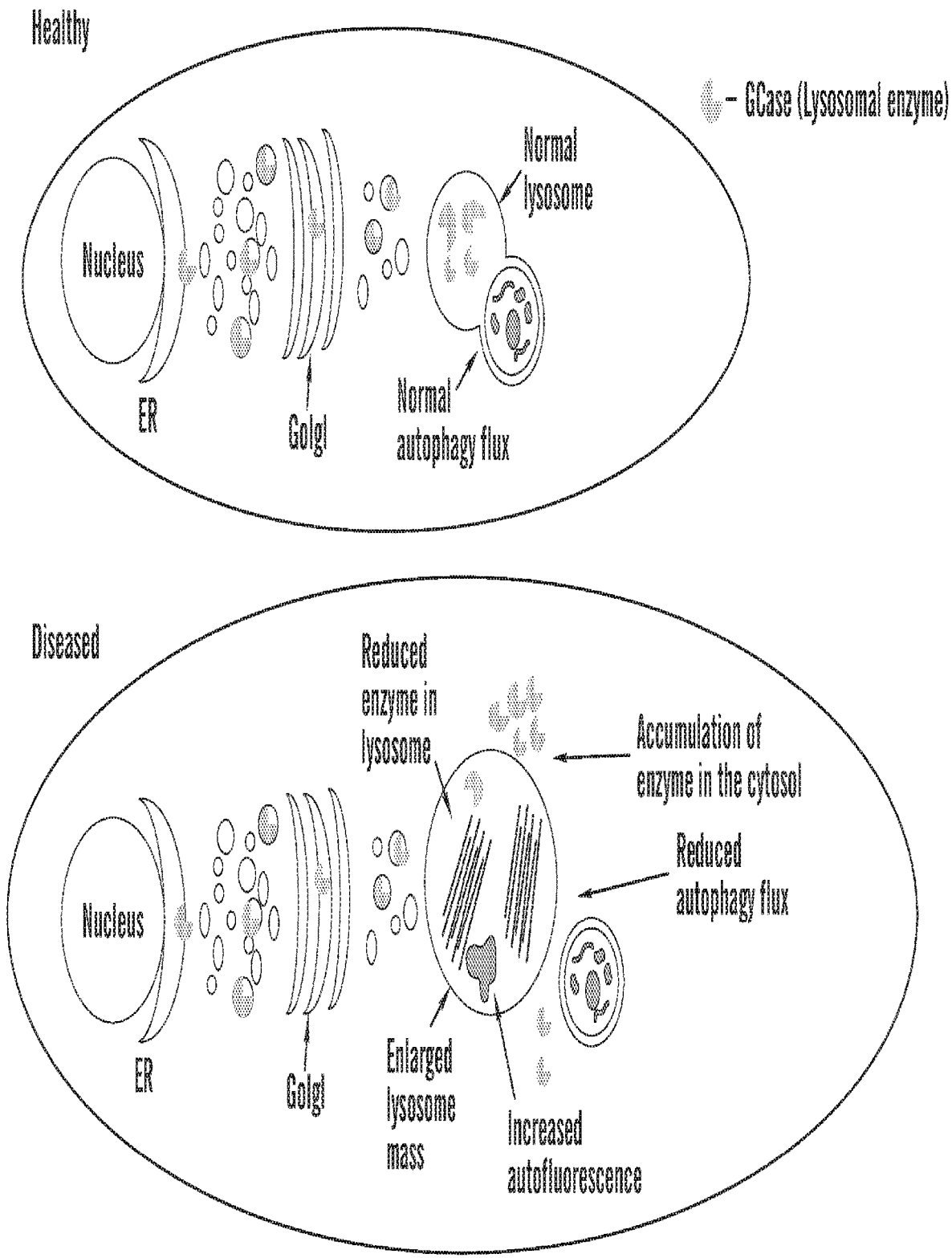
FIG. 13A provides readouts of lysosomal function assays, reflecting healthy (top) and diseased (bottom) cellular states.
Figure 13B:
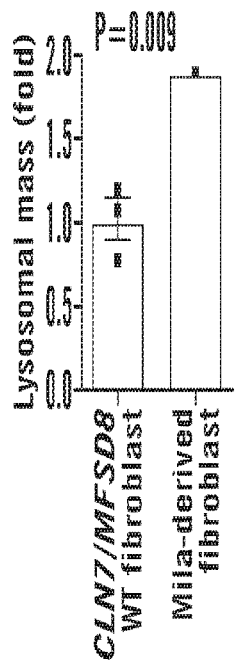
FIGS. 13B, FIG. 13C, FIG. 13D, FIG. 13E, and FIG. 13F are graphs showing differences in lysosomal function between the subject-derived fibroblast and CLN7/MFSD8 wild type fibroblast cells (BJ1). P values were calculated using one-sided Student's T test.
Figure 13C:
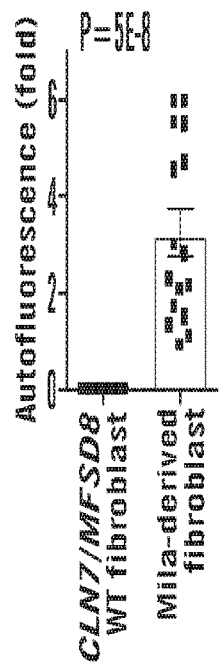
Figure 13D:
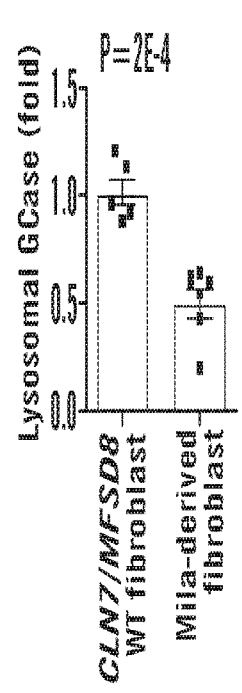
Figure 13E:
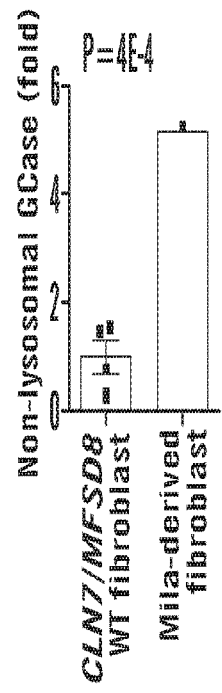
Figure 13F:
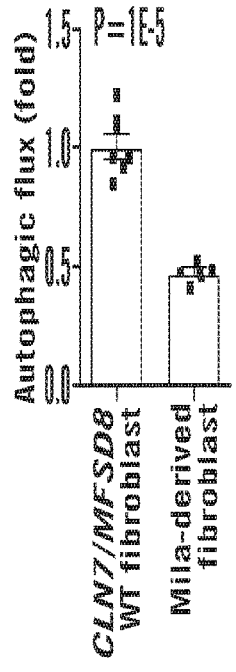
Figure 13G:
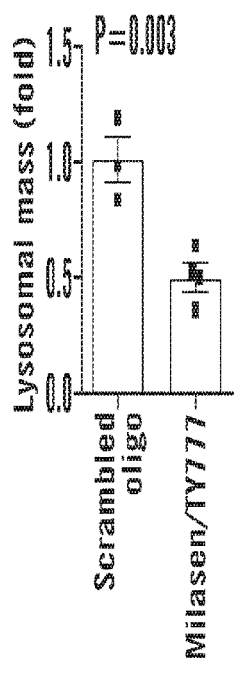
FIG. 13G, FIG. 13H, FIG. 13I, FIG. 13J, and FIG. 13K graphically illustrate the differences in lysosomal function between the subject-derived fibroblasts treated with scrambled oligonucleotide (TY772) and with milasen/TY777.
Figure 13H:
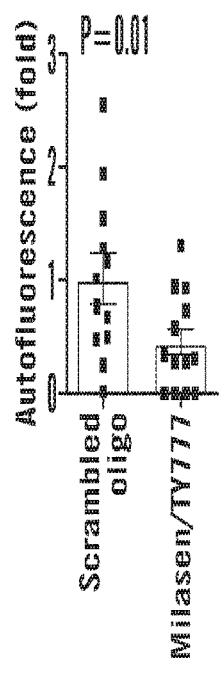
Figure 13I:
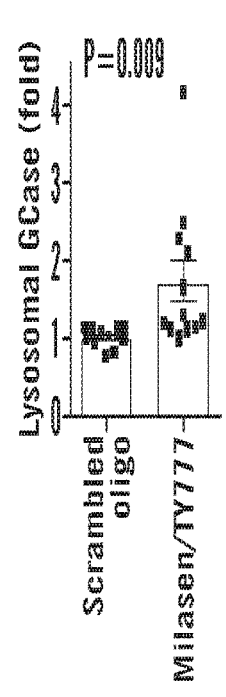
Figure 13J:
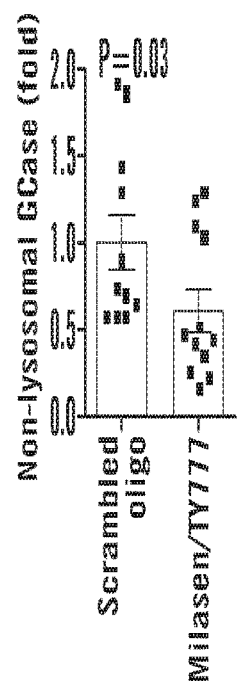

Example 2: Antisense Oligonucleotides Improved Lysosomal Function in a Fibroblast NCL Model The subject's fibroblasts exhibited several cellular phenotypes (FIG. 13A-K) characteristic of lysosomal dysfunction. Subject's fibroblasts showed double the typical lysosomal mass relative to controls (FIG. 13B), consistent with the increase in lysosomal number and size seen in many lysosomal storage disease states. the subject's fibroblasts also demonstrated a strong autofluorescence signal not seen in controls (FIG. 13C), a well-documented observation in neuronal ceroid lipofuscinosis that is associated with functional backup of lysosomes leading to accumulation of lipid and protein aggregates. Finally, the subject's fibroblasts possessed a 40% reduction in enzymatic hydrolase activity within lysosomes (FIG. 13D), but a 5× increase in hydrolase activity within the cytosol (i.e. outside of lysosomes; FIG. 13E), demonstrating a breakdown in proper compartmentalization of lysosomal hydrolases. Lastly, the subject's fibroblasts showed reduced autophagic flux, consistent with lysosomal dysfunction (FIG. 13F).

Figure 13K:
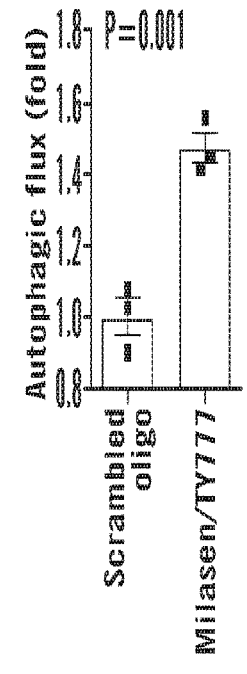
Figure 14A:
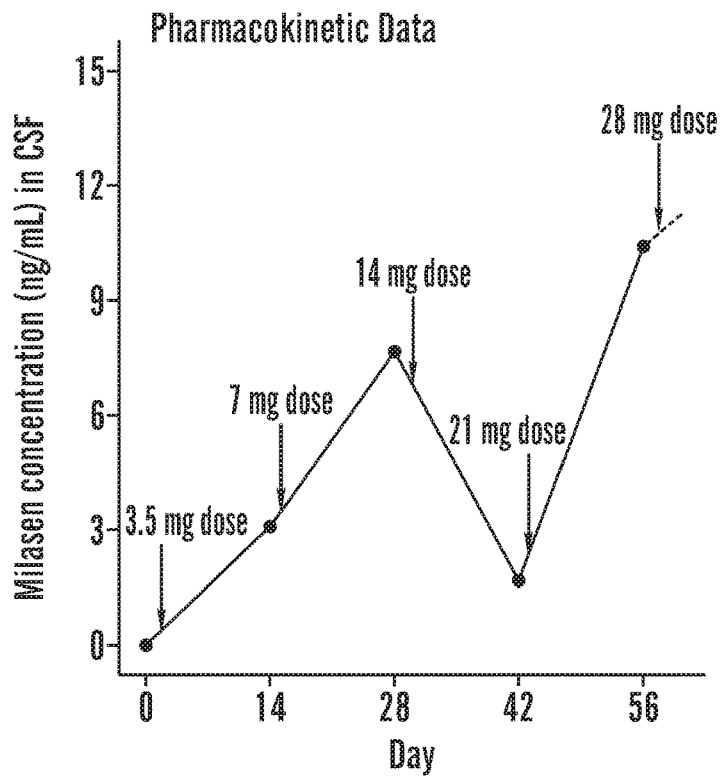
FIG. 14A and FIG. 14B show Milasen concentration in cerebrospinal fluid (CSF) and plasma, respectively, at various time points.
Figure 14B:
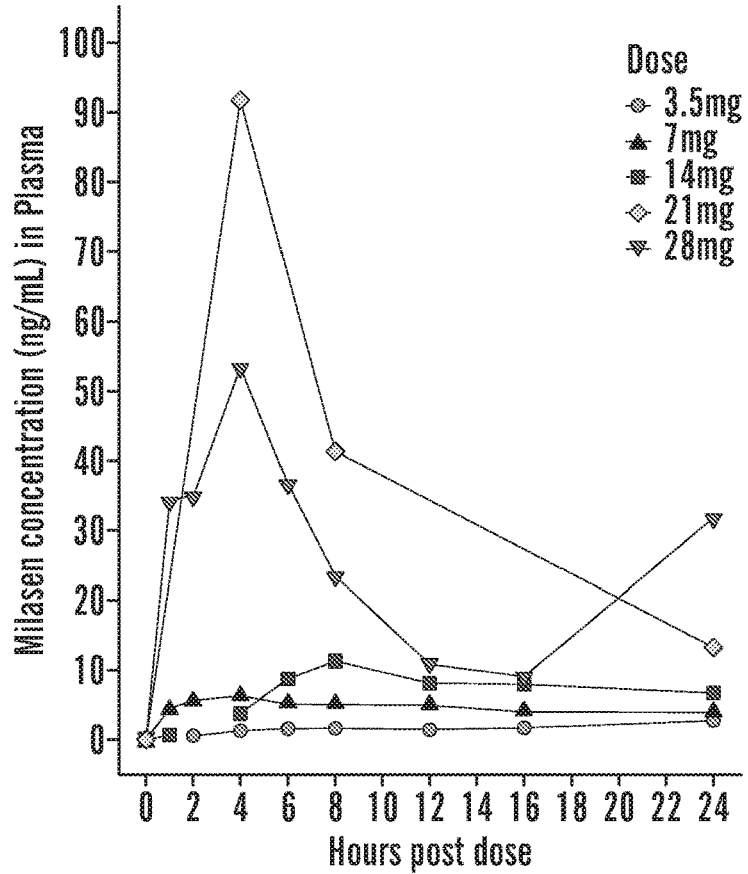
Figure 15:
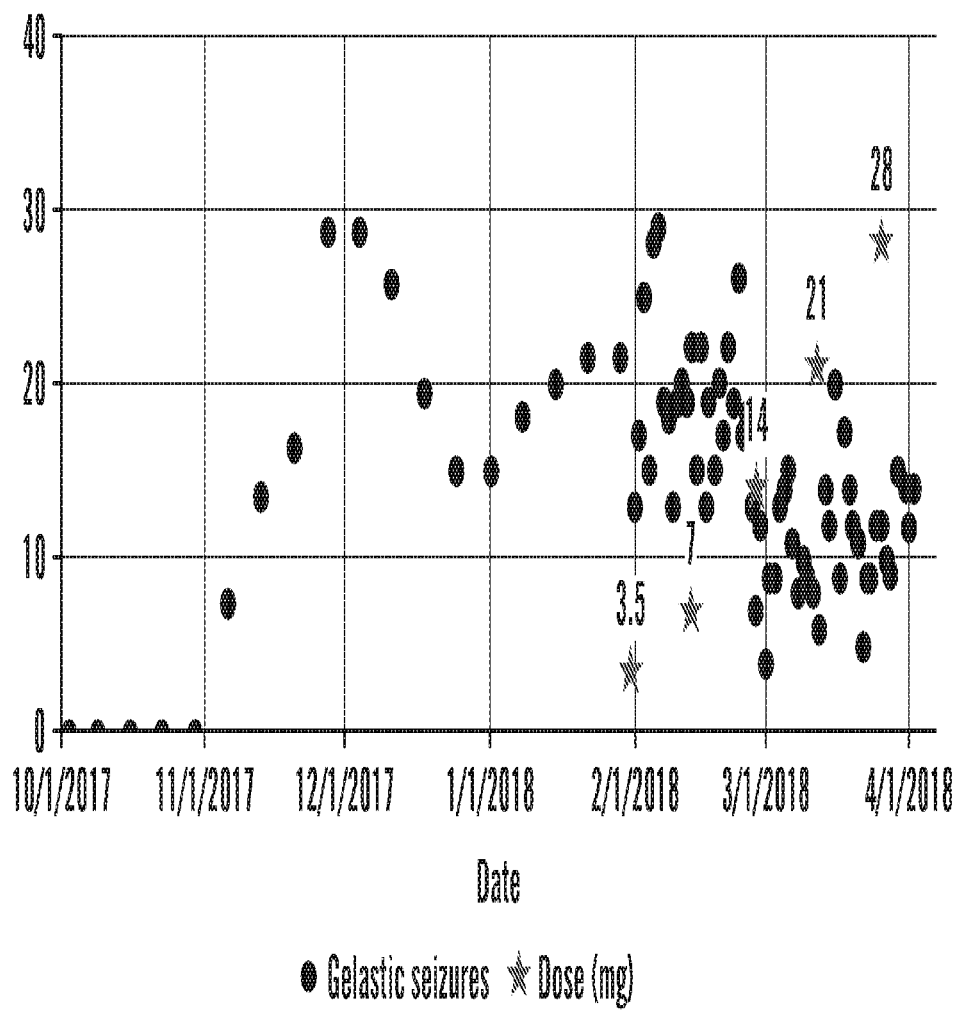
FIG. 15 shows changes in daily seizure frequency in the subject over time.
Figure 16:
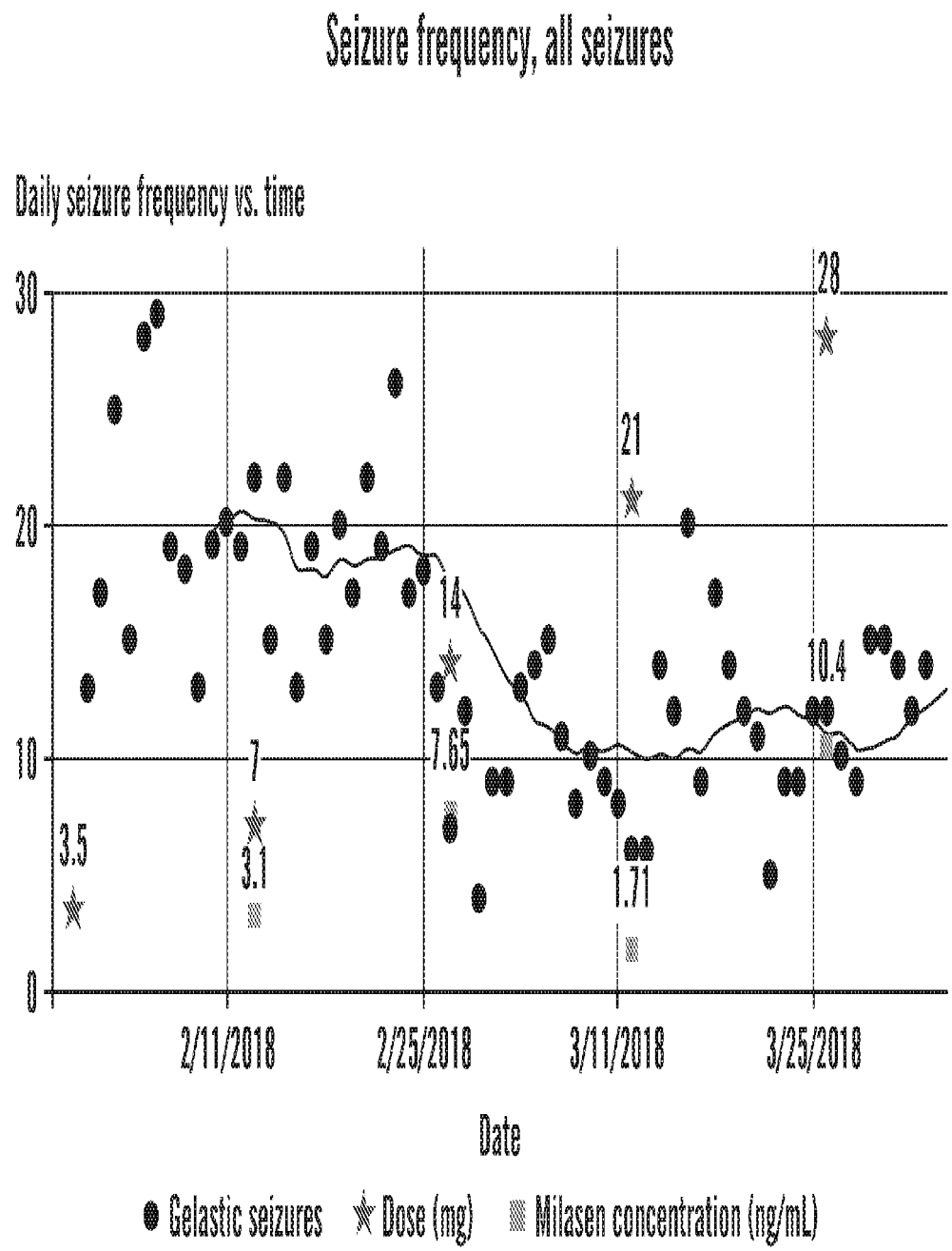
FIG. 16 shows changes in seizure frequency over time.
Figure 17:
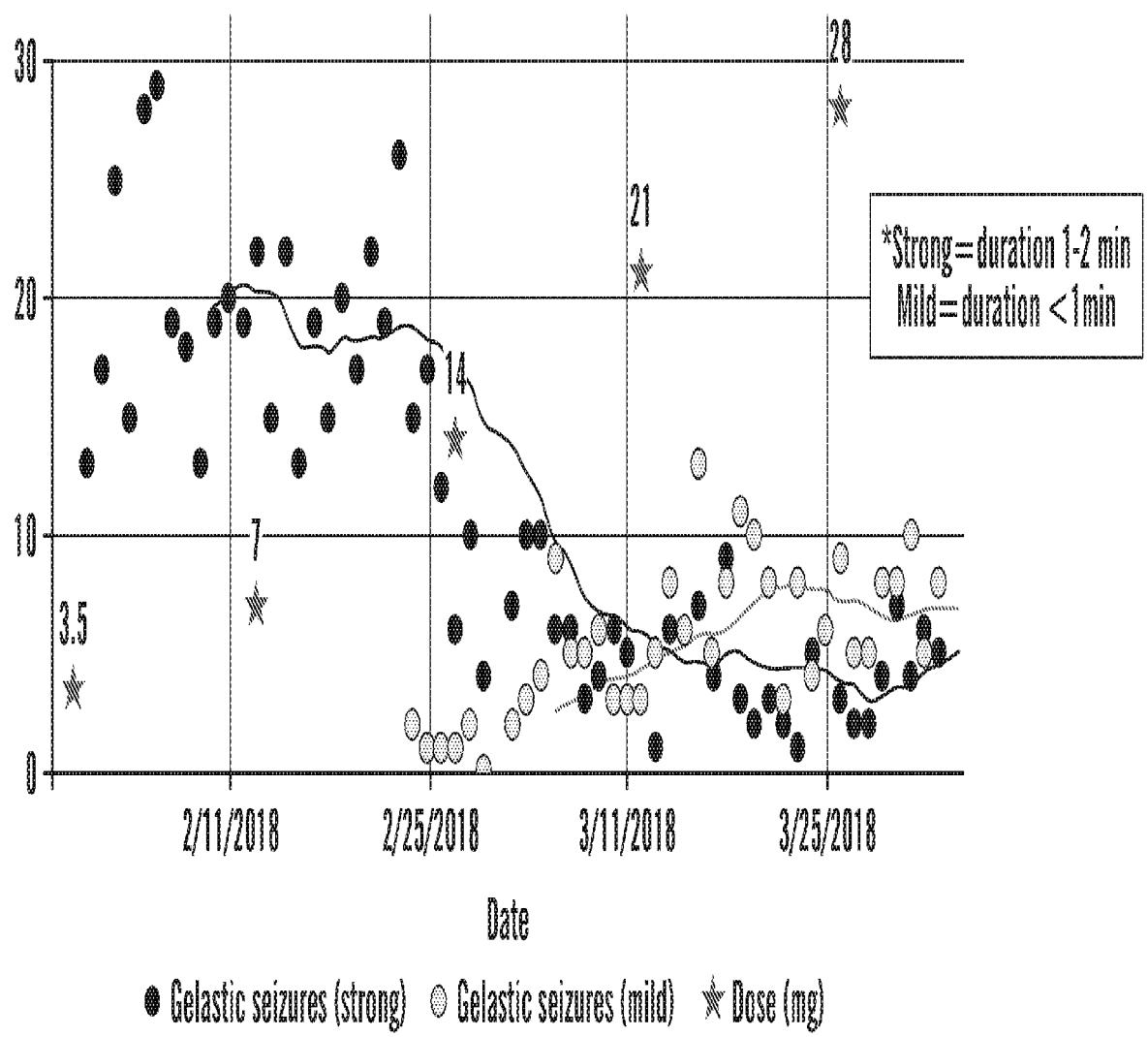
FIG. 17 shows changes in the frequency of strong and mild seizures over time.

Transfection of fibroblasts with milasen/TY777 resulted in significant reduction of lysosomal mass (FIG. 13G), significant reduction of accumulation of autofluorescence pigment (FIG. 13H), significant increases in hydrolase activity within lysosomes (FIG. 13I), and a trend, albeit not reaching significance, towards reduction in hydrolase activity outside of lysosomes (FIG. 13J), and significant restoration of autophagic flux (FIG. 13K). Together, these results provided evidence that oligonucleotide treatment of the subject's cells would not only improve normal splicing but also restore cellular lysosomal function.

Together, these results demonstrate that the subject harbors an intronic SVA retrotransposon insertion that causes abnormal splicing and exon trapping of CLN7/MFSD8, and provides encouraging evidence that antisense oligonucleotide treatment with TY777/milasen can not only restore normal splicing but also restore cellular lysosomal function.

Example 3: Toxicology

Toxicology was assessed in Sprague-Dawley rats, which are commonly used for intrathecal dosing and tolerate implanted catheters for redosing on longer term studies with few catheter failures or infections. They are sensitive to non-sequence related oligonucleotide toxicity and have been extensively used in oligonucleotide toxicity studies; therefore, they are considered sensitive and relevant. Because milasen is designed to suppress an abnormal splice product caused by the subject's unique gene mutation, there are no applicable target mRNA sequences found in any species, so toxicities seen from milasen in any animal species will be non-target mediated in nature, so there would be no added benefit to risk assessment gained from studying milasen in other species. Similar reasoning (of limiting toxicity to only rodents) is used in cases where specifically designed monoclonals target viruses and no target is present in any healthy animals.

The rat high dose of 1 mg delivered by intrathecal delivery was considered a No Observed Adverse Effect Level (NOAEL) This was based on the clinical observations (transient hind limb limitations for 24 h), neurological exams (subtler neurobehavioral effects on hind limbs were present at 24 h, but were resolved fully by 5 d, and 8 d as well), and histopathology (no neuronal toxicity was seen in spinal cord or brain). There were no adverse effects evident from hematology or clinical chemistry assessment panels. Notably, class-related effects seen with intravenously delivered oligos did not occur (such as thrombocytopenia, anticoagulant, or nephrotoxicity); this dovetails with the biodistribution data showing limited systemic exposure as assessed by plasma. The only milasen-associated histopathologic findings were minimal to mild vacuolated inflammatory cells that may contain test article or be responding to a combined inflammatory effect from recent surgery (local tissues are disrupted by catheter implant) and lumbar infusion of a foreign, charged substance into a confined area. The presence of inflammatory cells is considered non-adverse since they are seen at day 8 post dosing (necropsy date), when all hind limb effects had resolved. The hind limb effects alone, were carefully examined at multiple time points and fully resolved, and were not associated with any histopathologic evidence of neuronal degeneration. Hind limb weakness was also reported in monkeys following intrathecal dosing with nusinersen, but these also resolved. Therefore, the weight of evidence suggests these transient hind limb effects are nonadverse; taken together, evidence supports using 1 mg in rat as the basis for covering the safe dose ranges in the human subject.

The rat to human (compartmental) scaling factor was based on estimating the ratio of the highest theoretic concentration at time zero (C0) in the rat and human CSF. C0 (the highest possible concentration immediately post dosing) can be estimated by dividing the delivered mass of drug by the theoretic compartment volume: the highest rat dose (NOAEL) was 1 mg (1000 μg) and dividing by the rat CSF volume (0.300 ml) yields a C0 of 3333 μg/ml. The theoretic C0 instead of the measured CSF value in rats was used because the biodistribution study was very limited in design (due to limited availability of research grade test article) and did not include an immediately-post-dose sacrifice group for obtaining an approximate Cmax. Comparing C0 with the far lower levels seen at 4 hours (3333 vs. 189.1 μg/ml), it seems evident (and consistent with polyphasic pattern of disposition observed with related oligonucleotides) that by 4 hrs, the earliest sacrifice time point, extensive distribution had already occurred primarily into the CNS and cord; very little was distributed to plasma (0.07% was found in plasma at 4 hrs and none thereafter). Therefore, the best basis for rat and human dose comparison is the C0 ratio in CSF for rat and the human subject. To obtain the right scaling factor for the rat and human CSF compartments, the subject's CSF volume was estimated to be 150 ml (a typical volume for her height, weight and age) and rat CSF volume to be 300 μl; rat weights ranged from ~280 to ~320 g so this is a reasonable rat compartment volume estimate. This represents a human/rat CSF volume ratio of 500×. In order to provide a conservative safety margin, and considering that there is no animal model of the subject's unique mutation and Batten Disease/NCL, an estimated starting dose in human was used that offers room for dose escalation and the opportunity to monitor the subject's reactions to drug before escalation. The subject's starting dose was 3.5 mg (several fold lower than nusinersen) which will yield an estimated C0 (3500 μg/150 ml), or 23 μg/ml. Compared to 3333 μg/ml at the NOAEL in rats, this is a safety margin (rat/human CSF; C0 concentration ratio) of 142×. Subsequent doses (7 mg and 14 mg) are planned at two week intervals to provide time for gathering safety and efficacy data because the target site of action for the subject is in the brain, and not directly in the spinal cord as in the case for nusinersen and SMA.

TABLE 3

| Rat | Human | Estimated C0 |
|---|---|---|
| 0.007 mg | 3.5 mg | 23 μg/mL |
| 0.014 mg | 7 mg | 47 μg/mL |
| 0.028 mg | 14 mg | 93 μg/mL |
| 0.06 mg * | 30 mg | 200 μg/mL |
| 0.25 mg * | 125 mg | 833 μg/mL |
| 1.0 mg *† | 500 mg | 3333 μg/mL |

* tested; see section 7.1.1. Study No. 5500241 and Section 7.3.1. Study No. 5500230
† rat intrathecal NOAEL Dose escalation over time allows for the possibility to explore saving the subject from further decline, possibly reversing some of the more recent losses in function, and giving her only treatment option the best opportunity to work. Further doses escalations are planned if the subject tolerates the drug, but beyond the dose series of 3 doses over 6 weeks.

Example 4: Therapeutic Administration of Antisense Oligonucleotides Shows Efficacy in Human Subject Additional primers (see below) were designed against sequences within CLN7/MFSD8 and the SVA transposon insertion and used to detect normal and abnormal CLN7/MFSD8 splice products (35 cycles, 98° C. for 5 s, 60° C. for 15 s, and 72° C. for 15 s) using 1 μL of cDNA prepared from patient and family member samples. GAPDH and 18S RNA were used as loading controls. For quantification experiments, primers TY715, TY758, and TY759 were used in competitive multiplex PCR.

TY715/TY759 amplify a 233 bp band representing wild-type splicing between exons 6 and 7, whereas TY715/TY759 amplify a 190 bp band representing abnormal splicing between exon 6 and cryptic exon i6. Relative quantities of wild-type and abnormally spliced products were calculated using 2% agarose gel electrophoresis, staining, and densitometry analysis (ImageJ). The primers and probes used in RT-PCR assays are shown in the following table:

TABLE 4

| Primer name | Sequence |
|---|---|
| TY714-MFSD8-RT-F2 | TCTCAGCAGTGTAGGGTTTTCT |
| TY715-MFSD8-RT-F3 | TGGAGGAGGAAATGTAGCAGTT |
| TY734-MFSD8-Exon7-R1 | TCACATCCCATGTCACACCT |
| TY743-18S-RNA-RT-F1 | CATTCGAACGTCTGCCCTAT |
| TY744-18S-RNA-HT-R1 | CAATTACAGGGCCTCGAAAG |
| TY747-GAPDH-RT-F1 | GAGTCAACGGATTTGGTCGT |
| TN748-GAPDH-RT-R1 | TTGATTTTGGAGGGATCTCG |
| TY758-MFSD8-I6-R | TGTTAGTGCTTGTTGAGGGCT |
| TY759-MFSD8-E7-R | ATTCCCAGGAAGGCGCTAAG |

Quantitative RT PCT

RNA samples were analyzed by RT-qPCR (Comparative Cτ (ΔΔCτ) assay). Two assays (primers/probe sets) were used to amplify abnormal E6-i6 and normal E6-E7 exon junctions. GAPDH was used as an internal control. Untransfected cell samples were used as a reference samples for final ΔΔCτ calculations. Primers and probes used in the TaqMan™ assays are shown in the table below:

TABLE 5

| Primer name | Sequence | Probe label | Amplicon size (bp) |
|---|---|---|---|
| MFSD8-E6-i6-fwd | AGCATGTGTCAAGCATTAGGT | FAM | 101 |
| MFSD8-E6-i6 rev | AGTGCTTGTTGAGGGCTTATT | | |
| MFSD8-E6-i6 probe | AGGTCCAGATGAGTAAATGTAAGCCTGA | | |
| MFSD8-E6-E7 fwd | ACATAAGCATGTGTCAAGCATTAG | FAM | 150 |
| MFSD8-E6-E7 rev | CCAGGAAGGCGCTAAGTAAA | | |
| MFSD8-E6-E7 probe | AGGTGTGACATGGGATGTGATTAAACTGC | | |
| GAPDH fwd | GGTGTGAACCATGAGAAGTATGA | VIC | 123 |
| GAPDH rev | GAGTCCTTCCACGATACCAAAG | | |
| GAPDH probe | AGATCATCAGCAATGCCTCCTGCA | | |

The present invention provides one or more antisense oligonucleotides that are useful to induce skipping of a deleterious exon associated with the insertion of a retrotransposon into a gene. In particular embodiments, an antisense oligonucleotide targets SVA or a fragment thereof. Antisense oligonucleotides targeting the retrotransposon or a mutation introduced by the retrotransposon are useful for the treatment of diseases or disorders associated with the presence of a deleterious mutation at one allele of a gene and a retrotransposon insertion that disrupts the corresponding allele.

Example 5: Therapeutic Effects of Anti-Sense Oligonucleotide Therapy

In November 2016, the subject, a seven year old girl, was diagnosed with a form of Batten disease. Within a year of being diagnosed, she went from playing independently to walking with assistance. Her language has deteriorated, and in September 2017, she had a G-tube placed to maintain her nutritional status in the face of increasing difficulty swallowing. Her seizure frequency has also increased. In an effort to preserve her intelligence and personality, anti-sense oligonucleotide development was undertaken to determine whether blockade of splicing from exon 6 to i6.SA with an antisense oligonucleotide could restore normal CLN7/MFSD8 RNA processing and improve lysosomal functioning.

Milasen consists of a 22 nucleotide oligonucleotide with 2'-O-methoxyethyl modified bases and a full phosphorothioate. It utilizes the same chemistry as the recently approved oligo, nusinersen, a well-tolerated and highly similar oligo that is injected directly into spinal fluid of infants and children with SMA. Milasen only differs in sequence and slightly in length (22 nucleotides for milasen vs 18 for nusinersen). This is the common length for oligo drugs because the length is sufficient to ensure avid and specific binding to only one site in the subject's genome. These synthetic oligo agents do not integrate into, or otherwise directly alter, the subject's DNA itself—they interact with the CLN7/MSD8 nuclear RNA transcript, only at the RNA site where her splice defect is exhibited. Because her genome was sequenced, it was determined that there are no other sites which can bind Milasen. Thus, milasen is a selective agent that can correct SVA transposon-induced splicing defect. Substantial oligonucleotide drug levels in brain can be achieved by lumbar intrathecal administration (Finkel et al., Lancet 388, 3017-3026, 2016).

Milasen will be supplied as a 2 mL vial containing 8.46 mg/mL milasen. Prior to injection, milasen will be diluted with Elliott's B to the indicated dosage level to an injection volume of 5 mL per dose administered intrathecally.

Milasen is being administered using a dose escalation period followed by a loading phase and a maintenance phase. Doses of 3.5 mg, 7 mg, and 14 mg, each spaced two weeks apart, were used initially. The subject undergoes 48 hours of inpatient observation after each dose. During this phase, blood and CSF samples have been drawn for pharmacokinetic (PK) assessments. CSF samples were withdrawn immediately prior to each dose administration, with samples collected on Day 0, Day 14, Day 28, and Day 42. Also, at each dosage level, blood samples were drawn pre-dosing, immediately post dose, and at 1, 2, 4, 6, 8, 12, 16, and 24 hours post-dosing.

The subject is showing improvement in response to treatment. Prior to treatment, the subject has between 15-25 seizures per day. Daily seizure activity and overall frequency is trending downward following initiation of therapy. Seizure severity is also trending downward. Following the $4^{th}$ dose of Milasen, the subject was having about 10 seizures per day.

Four months after initiation of treatment, the subject had her first seizure free day.

The results described herein were obtained using the following methods and materials.

Skin Fibroblast Derivation, Lymphoblastoid Cell Line (LCL) Generation, and Maintenance Fibroblasts Patient skin fibroblasts were derived from 3 mm skin punch biopsy by explant culture. Fibroblasts were maintained and passaged in media containing Alpha MEM (Irvine Scientific), Chang Medium B (Irvine Scientific), and supplemented with Chang C Supplement (Irvine Scientific), GlutaMAX™ (Life Technologies) and 10% fetal bovine serum (FBS) (Life Technologies). Fibroblasts used in experiments were under passage 20.

Lymphoblastoid Cell Lines (LCL)

5 ml peripheral blood from each donor (Proband, Mother, Father and Brother) were drawn into a heparinized blood tube. Mononuclear cells (MNC) were isolated by density gradient centrifugation using Ficoll Histoplaque®-1077 (Sigma-Aldrich). LCL were established by infecting MNC with Epstein-Barr Virus (EBV). LCL were established in 2-4 weeks and maintained in RPMI 1640 (Caisson Lab) supplemented with 10% FBS (Life Technologies).

Transfection

Fibroblasts and LCL were transiently transfected with ASOs using Lipofectamine™ 3000 (ThermoFisher) according to the manufacturer's instructions. ASOs were used at 100 nM. Transfected cells were harvested at 24 hours. For dose-response experiments, fibroblasts were transfected by electroporation (Neon Transfection System, ThermoFisher) according to the manufacturer's instructions. ASO were used at concentrations ranging from 1-1000 nM as indicated. Transfected cells were harvested at 24 hours.

RNA Extraction and cDNA Synthesis

Two methods were used for RNA isolation and cDNA synthesis: Total RNA was isolated using Pure Link™ RNA mini kits (Life Technologies) according to the manufacturer's instructions. cDNA synthesis using oligo-dT was performed with the Super Script II reverse transcriptase kit (Invitrogen) according to the manufacturer's instructions.

Alternatively, total RNA was purified using RNeasy® Plus Mini Kit (Qiagen) according to the manufacturer's instructions. cDNA synthesis was performed in concert with RT-qPCR using gene-specific primers and gScript™ XLT One-Step RT-qPCR ToughMix®, Low ROX™ kits (VWR Quanta Biosciences™).

RT-PCR

Primers (see below) were designed against sequences within CLN7/MFSD8 and the SVA transposon insertion and used to detect normal and abnormal CLN7/MFSD8 splice products (35 cycles, 98° C. for 5 s, 60° C. for 15 s, and 72° C. for 15 s) using 1 μL of cDNA prepared from patient and family member samples. GAPDH and 18S RNA were used as loading controls. For quantification experiments, primers TY715, TY758, and TY759 were used in competitive multiplex PCR. TY715/TY759 amplify a 233 bp band representing wildtype splicing between exons 6 and 7, whereas TY715/TY759 amplify a 190 bp band representing abnormal splicing between exon 6 and cryptic exon i6. Relative quantities of wildtype and abnormally spliced products were calculated using 2% agarose gel electrophoresis, staining, and densitometry analysis (ImageJ).

Dose Response Curve

Dose-response curves, EC50, and IC50 values were calculated and plotted with Prism software (Graphpad).

RNA-Seq

RNA-seq libraries were prepared using WaferGen PrepX kit (WaferGen Biosystems). Sequencing was performed on an Illumina NextSeq machine using 2×150 bp paired-end reads. Library preparation and sequencing was repeated four more times using alternative kits, KAPA Hyper Prep kit (KAPA Biosystems; for library preparation) and HiSeq 2500 (for sequencing). As the replicates showed consistent results, we aggregated the data from all five runs and used it for the analysis in this report. For quality control of sequencing reads, Cutadapt (version 1.11) and Trimmomatic (version 0.36) was used to trim adapter sequences and low quality bases at the ends—reads that were trimmed to be shorter than 30 nts were removed. Reads that contain a region of consecutive low quality bases in the middle were also removed. For alignment, HISAT2 (version 2.1.0) was used to map reads on human genome (hg19) in the paired-end, two-pass mode, generating alignments in SAM format. Using Samtools, the SAM files were converted to BAM format and subsequently sorted and indexed by chromosomal coordinate. Gene annotation was not provided to the alignment program in order to avoid any biased alignment favoring annotated splice junctions. The sorted BAM files were indexed using Samtools. IGV was used to draw Sashimi plots, which showed the number of reads supporting splice junctions in the genomic region containing CLN7/MFSD8 exon 5 through 7.

Lysosomal Function Assessment

Lysosomal and cytosolic activity of lysosomal beta-Glucocerebrosidase (GCase) was measured in living cultures of patient and control fibroblasts using the artificial GCase substrate, PFB-FD-Gluc. Activity was normalized to lysosomal mass, quantified by cascade blue dextran, and analyzed as previously described (Mazzulli et al., Proc. Natl. Acad. Sci. 113, 1931-1936, 2016). Autofluorescent pigment was measured by assaying fluorescence of living cells in a microplate reader cultured in phenol red-free media (excitation=485 nm, emission at 530 nm). Values are presented as mean+/−SEM and p-values are presented using Student's t-test. For autophagic flux assays, fibroblasts were treated with either DMSO (vehicle control), or bafilomycin A1 (Baf A1) to autophagic lysosomal fusion. Cells were extracted in 1% Triton X-100 buffer and response to bafA1 was analyzed by western blot analysis for LC3 levels. alpha-Tubulin (a-Tub) or GAPDH were used as loading controls.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

SEQUENCE LISTING

The patent contains a lengthy sequence listing. A copy of the sequence listing is available in electronic form from the USPTO web site (https://seqdata.uspto.gov/?pageRequest=docDetail&DocID=US11999953B2). An electronic copy of the sequence listing will also be available from the USPTO upon request and payment of the fee set forth in 37 CFR 1.19(b)(3).

What is claimed is:

1. One or more antisense oligonucleotides complementary to an intronic sequence within a genome, wherein the one or more antisense oligonucleotides comprises a modified backbone, wherein the modified backbone comprises a 2' methoxy ethyl modification or a 2' O-methyl modification, wherein the one or more antisense oligonucleotides binds a splice acceptor site activated by a transposable element or a predicted splice enhancer sequence flanking the splice acceptor site, wherein the one or more antisense oligonucleotides induces exon skipping of an exon, and wherein the one or more antisense oligonucleotides have at least 85% sequence identity to the entire length of the nucleotide sequence AGCUUUUCAGGCUUACAUUUACUCAUCU (SEO ID NO. 2578) or the nucleotide sequence AAUGUUAGUGCUUGUUGAGGGC (SEO ID NO. 2579).

2. The antisense oligonucleotide of claim 1, further comprising at least one modified nucleobase.

3. A set of antisense oligonucleotides comprising 2 or more of the antisense oligonucleotides of claim 1.

4. A pharmaceutical composition comprising of the antisense oligonucleotide of claim 1 in a pharmaceutically acceptable excipient.

5. The one or more antisense oligonucleotides of claim 1, wherein the antisense oligonucleotides further comprise a 5-methyl cytosine and/or a 5-methyl uracil.

* * * * *